United States Patent [19]
Bookstein et al.

[11] Patent Number: 6,043,088
[45] Date of Patent: Mar. 28, 2000

[54] PROSTATE/COLON TUMOR SUPPRESSOR GENE LOCATED ON HUMAN CHROMOSOME 8

[75] Inventors: Robert Bookstein, La Jolla, Calif.; William B. Isaacs, Glyndon, Md.

[73] Assignees: Canji, Inc., San Diego, Calif.; Johns Hopkins University, Baltimore, Md.

[21] Appl. No.: 08/445,515

[22] Filed: May 22, 1995

Related U.S. Application Data

[63] Continuation-in-part of application No. 08/246,604, May 20, 1994, abandoned.
[51] Int. Cl.$^7$ .............................. C12N 5/08; C12N 1/00; C12N 15/63; C07H 21/04
[52] U.S. Cl. ...................... 435/366; 435/243; 435/320.1; 435/325; 536/23.5; 536/24.31
[58] Field of Search .............................. 435/69.1, 320.1, 435/243, 325, 366; 536/235, 24.31

[56] References Cited

PUBLICATIONS

Coghlan (1995) New Scientist 145:14–15. Nov. 25, 1995.
Adams et al., "Sequence Identification of 2,375 Human Brain Genes"; *Nature* 355:632–634 (1992).
Albertsen et al., "Construction and Characterization of a Yeast Artificial Chromosome Library Containing Seven Haploid Human Genome Equivalents"; *Proc. Natl. Acad. Sci. USA* 87:4256–4260 (1990).
Atkin and Baker, "Chromosome Study of Five Cancers of the Prostate"; *Human Genetics* 70:359–364 (1985).
Bergerheim et al., "Deletion Mapping of Chromosomes 8, 10, and 16 in Human Prostatic Carcinoma"; *Genes, Chromosomes & Cancer* 3:215–220 (1991).
Bookstein et al., "Human Retinoblastoma Gene: Long–Range Mapping and Analysis of Its Deletion in a Breast Cancer Cell Line"; *Molecular and Cellular Biology* 9(4):1628–1634 (1989).
Bos et al., "Prevalence of ras Gene Mutations in Human Colorectal Cancers"; *Nature* 327:293–297 (1987).
Bova et al. "Homozygous Deletion and Frequent Allelic Loss of Chromosome 8p22 Loci in Human Prostate Cancer"; *Cancer Research* 53:3869–3873 (1993).
Boulianne et al., "Production of Functional Chimaeric Mouse/Human Antibody"; *Nature* 312:643–646 (1984).
Carter et al., "Allelic Loss of Chromosomes 16q and 10q in Human Prostate Cancer"; *Proc. Natl. Acad. Sci. USA* 87:8751–8755 (1990).
Coffey, Donald, "Prostate Cancer"; *Cancer* 71:880–886 (1993).
Cohen et al., "A First–Generation Physical Map of the Human Genome"; *Nature* 366:698–701 (1993).
Cox et al., "Radiation Hybrid Mapping: A Somatic Cell Genetic Method for Constructing High–Resolution Maps of Mammalian Chromosomes"; *Science* 250:245–250 (1990).
Cunningham et al., "Deletion Mapping in Colorectal Cancer of a Putative Tumour Suppressor Gene in 8p22–p21.3"; *Oncogene* 8:1391–1396 (1993).

Emi et al., "Allelic Loss at Chromosome Band 8p21.3–p22 is Associated with Progression of Hepatocellular Carcinoma"; *Genes, Chromosomes & Cancer* 7:152–157 (1993).
Emi et al., "Frequent Loss of Heterozygosity for Loci on Chromosome 8p in Hepatocellular Carcinoma, Colorectal Cancer, and Lung Cancer"; *Cancer Research* 52:5368–5372 (1992).
Emi et al., "Structure, Organization, and Chromosomal Mapping of the Human Macrophage Scavenger Receptor Gene"; *The Journal of Biological Chemistry* 268:2120–2125 (1993).
Emi et al., "A Primary Genetic Linkage Map of 14 Polymorphic Loci for the Short Arm of Human Chromosome 8"; *Genomics* 15:530–534 (1993).
Fearon and Vogelstein, "A Genetic Model for Colorectal Tumorigenesis"; *Cell* 61:759–767 (1990).
Fujiwara et al., "Evidence for the Presence of Two Tumor Suppressor Genes on Chromosome 8p for Colorectal Carcinoma"; *Cancer Research* 53:1172–1174 (1993).
Gibas et al., "Chromosome Rearrangements in a Metastic Adenocarcinoma of the Prostate", *Cancer Genetics and Cytogenetics* 16:301–304 (1985).
Gnirke et al., "Microinjection of Intact 200–to 500–kb Fragments of YAC DNA into Mammalian Cells", *Genomics* 15:659–667 (1993).
Gnirke et al., "Cloning and in vivo Expression of the Human GART Gene Using Yeast Artificial Chromosomes"; *The EMBO Journal* 10(7):1629–1634 (1991).
Gnirke and Huxley, "Transfer of the Human HPRT and GART Genes from Yeast to Mammalian Cells by Microinjection of YAC DNA"; *Som. Cell Mol. Genetics* 17:573–580 (1991).
Green and Olson, "Systematic Screening of Yeast Artificial–Chromosome Libraries by use of the Polymerase Chain Reaction"; *Proc. Natl. Acad. Sci. USA* 87:1213–1217 (1990).
Gumerlock et al., "Activated ras Alleles in Human Carcinoma of the Prostate are Rare"; *Cancer Research* 51:1632–1637 (1991).
Hermanson et al., "Rescue of End Fragments of Yeast Artificial Chromosomes by Homologous Recombination in Yeast"; *Nucleic Acids Research*; 19(18):4943–4948 (1991).

(List continued on next page.)

*Primary Examiner*—George C. Elliott
*Assistant Examiner*—Robert Schwartzman
*Attorney, Agent, or Firm*—Townsend & Townsend & Crew LLP

[57] ABSTRACT

This invention provides a novel nucleic acid molecule encoding a prostate/colon tumor suppressor gene product. The means and methods for detecting mutations and/or loss of prostate/colon tumor suppressor gene are provided. Also included within the scope of this invention are methods of suppressing the neoplastic phenotype of cancer cells having a defect in the prostate/colon tumor suppressor gene product. The invention also includes the means and methods for treating the cancer by administering the prostate/colon tumor suppressor gene.

27 Claims, 23 Drawing Sheets

OTHER PUBLICATIONS

Hsieh et al., "A TaqI DNA Polymorphism in the Human Cathepsin B Gene (CTSB)"; *Nucleic Acids Research* 18(11):3430 (1990).

Hudson et al., "Isolation and Chromosomal Assignment of 100 Highly Informative Human Simple Sequence Repeat Polymorphisms"; *Genomics* 13:622–629 (1992).

Huxley et al., "The Human HPRT Gene on a Yeast Artificial Chromosome is Functional When Transferred to Mouse Cells by Cell Fusion"; *Genomics* 9:742–750 (1991).

Joslyn et al., "Identification of Deletion Mutations and Three New Genes at the Familial Polyposis Locus"; *Cell* 66:601–613 (1991).

Kern et al., "Allelic Loss in Colorectal Carcinoma"; *J. Amer. Med. Assoc.* 261:3099–3103 (1989).

Knowles et al., "Deletion Mapping of Chromosome 8 in Cancers of the Urinary Bladder Using Restriction Fragment Length Polymorphisms and Microsatellite Polymorphisms"; *Oncogene* 8:1357–1364 (1993).

Kodama et al., "Purification and Characterization of a Bovine Acetyl Low Density Lipoprotein Receptor"; *Proc. Natl. Acad. Sci. USA* 85:9238–9242 (1988).

Kunimi et al., "Allelotyping of Human Prostatic Adenocarcinoma"; *Genomics* 11:530–536 (1991).

Lacoste–Royal et al., "RFLP for TaqI at the Human Neurofilament (NF–L) Gene Locus"; *Nucleic Acids Research* 16:4184 (1988).

Levine, Arnold J., "The Tumor Suppressor Genes"; *Ann. Rev. Biochem.* 62:623–651 (1993).

Lundgren et al., "Cytogenetic Analysis of 57 Primary Prostatic Adenocarcinomas"; *Genes, Chromosomes & Cancer* 4:16–24 (1992).

Mattei et al., "Assignment of the Human Lipoprotein Lipase (LPL) Gene to Chromosome Band 8p22"; *Cytogenet. Cell Genet.* 63:45–46 (1993).

Matsumoto et al., "Human Macrophage Scavenger Receptors: Primary Structure, Expression, and Localization in Atherosclerotic Lesions"; *Proc. Natl. Acad. Sci. USA* 87:9133–9137 (1990).

Mellinger et al., "The Histology and Prognosis of Prostatic Cancer"; *The Journal of Urology* 97:331–337 (1967).

Meltzer et al., "Reduction to Homozygosity Involving p53 in Esophageal Cancers Demonstrated by the Polymerase Chain Reaction"; *Proc. Natl. Acad. Sci. USA* 88:4976–4980 (1991).

Morgan et al., "The Selective Isolation of Novel cDNAs Encoded by the Regions Surrounding the Human Interleukin 4 and 5 Genes"; *Nucleic Acids Research* 20(19):5173–5179 (1992).

Morrison et al., "Chimeric Human Antibody Molecules: Mouse Antigen–Binding Domains with Human Constant Region Domains"; *Proc. Natl. Acad. Sci. USA* 81:6851–6855 (1984).

Neuberger et al., "A Hapten–Specific Chimaeric IgE Antibody with Human Physiological Effector Function"; *Nature* 314:268–270 (1985).

Nowell, Peter C., "The Clonal Evolution of Tumor Cell Populations"; *Science* 194:23–28 (1976).

Polymeropoulos et al., "Dinucleotide Repeat Polymorphism at the Human Ankyrin Gene (ANK1)"; *Nucleic Acids Research* 19(4):969 (1991).

Shaw et al., "Characterization of a Mouse/Human Chimeric Monoclonal Antibody (17–1A) to a Colon Cancer Tumor–Associated Antigen"; *The Journal of Immunology* 138(12):4534–4538 (1987).

Schroder et al., "The TNM Classification of Prostate Cancer"; *The Prostate Supplement* 4:129–138 (1992).

Silverman et al., "Genetic Transfer and Expression of Reconstructed Yeast and Artificial Chromosomes Containing Normal and Translocated BCL2 Proto–Oncogenes"; *Molecular and Cellular Biology*; 13(9):5469–5478 (1993).

Strauss and Jaenisch, "Molecular Complementation of a Collagen Mutation in Mammalian Cells Using Yeast Artificial Chromosomes"; *The EMBO Journal* 11(2):417–422 (1992).

Sun et al., "Chimeric Antibody with Human Constant Regions and Mouse Variable Regions Directed Against Carcinoma–Associated Antigen 17–1A"; *Proc. Natl. Acad. Sci. USA* 84:214–218 (1987).

Tomfohrde et al. "Human Chromosome 8 Linkage Map Based on Short Tandem Repeat Polymorphisms: Effect of Genotyping Errors"; *Genomics* 14:144–152 (1992).

Tsui et al., "Report of the Committee on the Genetic Constitution of Chromosomes 7 and 8"; *Cytogenet. Cell Genet.* 51:166–201 (1989).

Vogelstein et al., "Allelotype of Colorectal Carcinomas"; *Science* 244:207–211 (1989).

Wagner et al., "A Hybrid Cell Mapping Panel for Regional Localization of Probes to Human Chromosome 8"; *Genomics* 10:114–125 (1991).

Weber and May, "Dinucleotide Repeat Polymorphism at the PENK Locus" and "Dinucleotide Repeat Polymorphism at the D2S72 Locus"; *Nucleic Acids Research* 18:2200 (1990).

Weber and May, "Abundant Class of Human DNA Polymorphisms Which Can Be Typed Using the Polymerase Chain Reaction"; *Am. J. Hum. Genet.* 44:388–396 (1989).

Weber et al., "Dinucleotide Repeat Polymorphisms at the D8S85, D8S87, and D8S88 Loci"; *Nucleic Acids Research* 18(13):4038 (1990).

Weissenbach et al., "A Second–Generation Linkage Map of the Human Genome"; *Nature* 359:794–801 (1992).

Weinberg, Robert, "Oncogenes, Antioncogens, and the Molecular Bases of Multistep Carcinogenesis"; *Cancer Research* 49:3713–3721 (1989).

Wood et al., "A DNA Marker for Human Chromosome 8 that Detects Alleles of Differing Sizes"; *Cytogenet. Cell Genet.* 42:113–118 (1986).

Wood and Schertzer, "Linkage Mapping of the D8S133 Locus to Chromosome 8p Using a Highly Informative, Polymorphic, Complex Dinucleotide Repeat"; *Genomics* 13:232 (1992).

Zuliani and Hobbs, "Tetranucleotide Repeat Polymorphism in the LPL Gene"; *Nucleic Acids Research* 18(16):4958 (1990).

Linkage maps
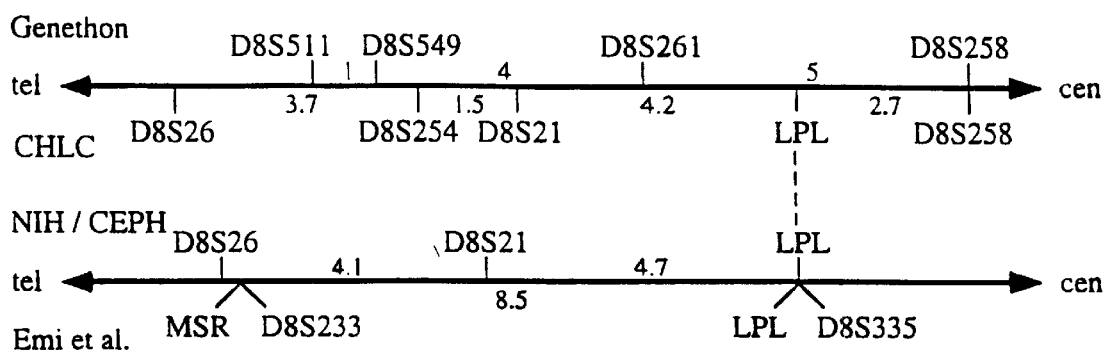
Physical maps
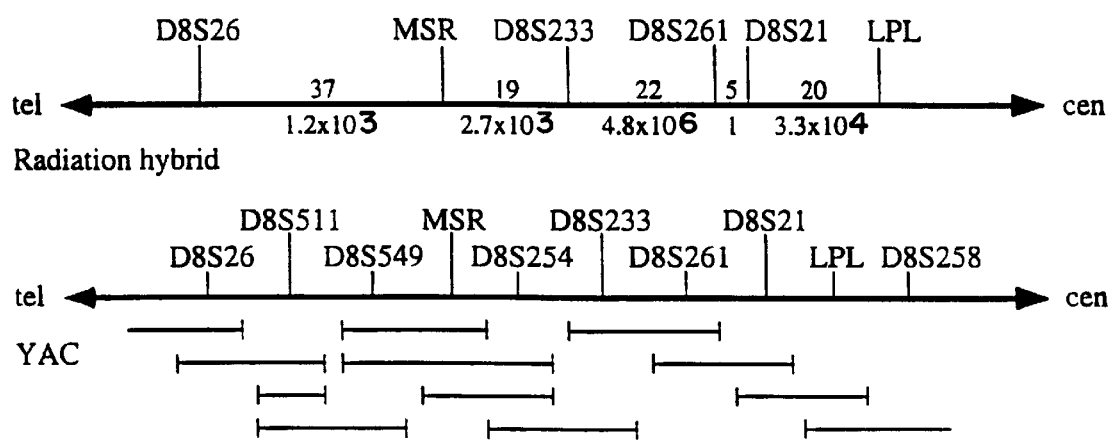
FIG. 5

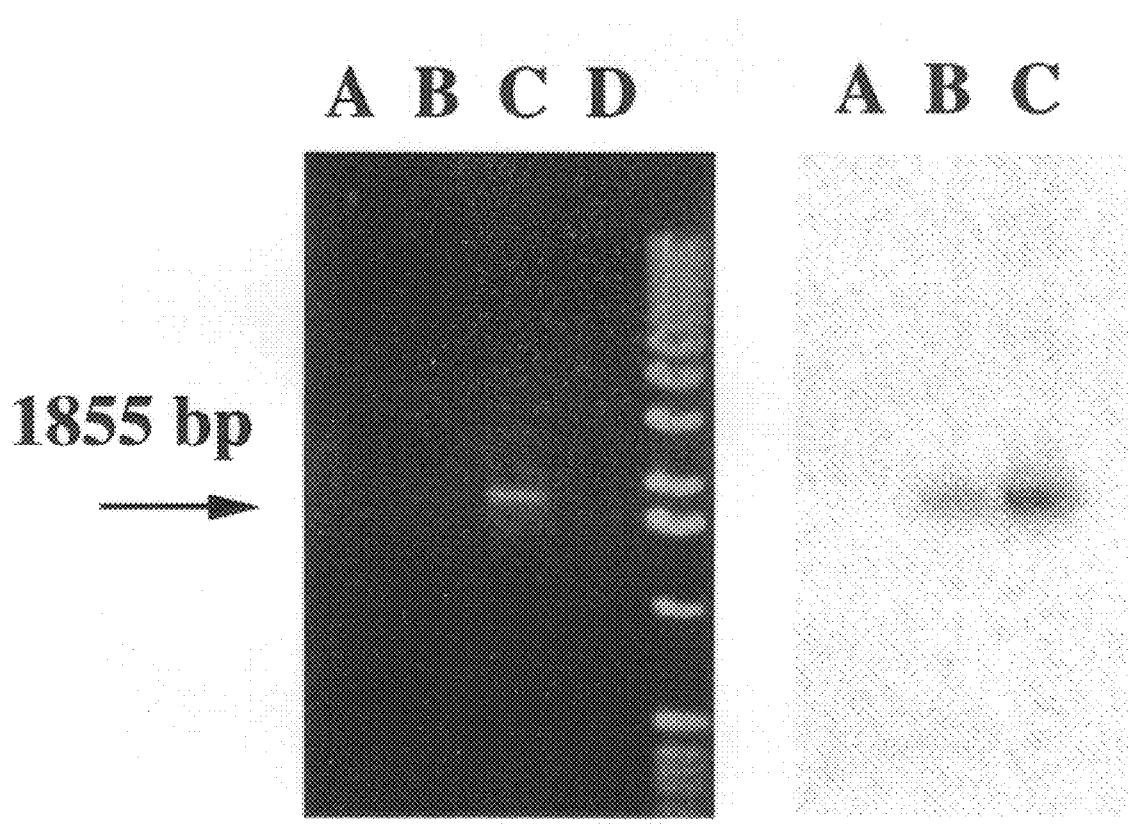

```
          10         20         30         40         50         60
5' GAATTCGGGCGGCCGCGGCCCGGGTCCCTCGCAAAGCCGCTGCCATCCCGGAGGGCCCAG
   ^          ^      ^^^ ^                              ^         ^
   EcoRI    NotI   XmaIAvaII                           MspI     ApaI
                   SmaI
                   AvaI
                   MspI 70         80         90        100        110        120
   CCAGCGGGCTCCCGGAGGCTGGCCGGGCAGGCGTGGTGCGCGGTAGGAGCTGGGCGCGCA
          ^              ^                               ^
         MspI          MspI                            BssHII 130        140        150        160        170        180
   CGGCTACCGCGCGTGGAGGAGACACTGCCCTGCCGCGATGGGGGCCCGGGGCGCTCCTTC
                                                ^^^
                                               ApaI
                                               XmaI
                                                SmaI
                                                AvaI
                                                MspI 190        200        210        220        230        240
   ACGCCGTAGGCAAGCGGGGCGGCGGCTGCGGTACCTGCCCACCGGGAGCTTTCCCTTCCT
                             ^ ^ ^          ^
                           BanIKpnI        MspI
                            RsaI 250        260        270        280        290        300
   TCTCCTGCTGCTGCTCTGCATCCAGCTCGGGGGAGGACAGAAGAAAAAGGAGAATCT
                              ^
                            AvaI 310        320        330        340        350        360
   TTTAGCTGAAAAAGTAGAGCAGCTGATGGAATGGAGTTCCAGACGCTCAATCTTCCGAAT
                         ^
                        PvuII 370        380        390        400        410        420
   GAATGGTGATAAATTCCGAAAATTTATAAAGGCACCACCTCGAAACTATTCCATGATTGT
                                       ^            ^
                                      BanI         TaqI 430        440        450        460        470        480
   TATGTTCACTGCTCTTCAGCCTCAGCGGCAGTGTTCTGTGTGCAGGCAAGCTAATGAAGA 490        500        510        520        530        540
   ATATCAAATACTGGCGAACTCCTGGCGCTATTCATCTGCTTTTTGTAACAAGCTCTTCTT 550        560        570        580        590        600
```

FIG.9A

CAGTATGGTGGACTATGATGAGGGGACAGACGTTTTTCAGCAGCTCAACATGAACTCTGC

```
       610       620       630       640       650       660
TCCTACATTCATGCATTTTCCTCCAAAAGGCAGACCTAAGAGAGCTGATACTTTTGACCT
              ^
            AvaIII 670       680       690       700       710       720
CCAAAGAATTGGATTTGCAGCTGAGCAACTAGCAAAGTGGATTGCTGACAGAACGGATGT
                    ^
                  PvuII 730       740       750       760       770       780
TCATATTCGGGTTTTCAGACCACCCAACTACTCTGGTACCATTGCTTTGGCCCTGTTAGT
                                    ^ ^ ^
                                   BanIKpnI
                                     RsaI 790       800       810       820       830       840
GTCGCTTGTTGGAGGTTTGCTTTATTTGAGAAGGAACAACTTGGAGTTCATCTATAACAA 850       860       870       880       890       900
GACTGGTTGGGCCATGGTGTCTCTGTGTATAGTCTTTGCTATGACTTCTGGCCAGATGTG
             ^
           StyI 910       920       930       940       950       960
GAACCATATCCGTGGACCTCCATATGCTCATAAGAACCCACACAATGGACAAGTGAGCTA
         ^
        AvaII 970       980       990      1000      1010      1020
CATTCATGGGAGCAGCCAGGCTCAGTTTGTGGCAGAATCACACATTATTCTGGTACTGAA
                                                           ^
                                                         RsaI
      1030      1040      1050      1060      1070      1080
TGCCGCTATCACCATGGGGATGGTTCTTCTAAATGAAGCAGCAACTTCGAAAGGCGATGT
              ^                                  ^
            StyI                                TaqI
      1090      1100      1110      1120      1130      1140
TGGAAAAAGACGGATAATTTGCCTAGTGGGATTGGGCCTGGTGGTCTTCTTCTTCAGTTT 1150      1160      1170      1180      1190      1200
TCTACTTTCAATATTTCGTTCCAAGTACCACGGCTATCCTTATAGTGATCTGGACTTTGA
                                   ^
                                 RsaI
      1210      1220      1230      1240      1250      1260
```

FIG. 9B

```
GTGAGAAGATGTGATTTGGACCATGGCACTTAAAAACTCTATAACCTCAGCCTTTTAATT
                    ^   ^
                    AvaII
                      StyI 1270      1280      1290      1300      1310      1320

AAATGAAGCCAAGTGGGATTTGCATAAAGTGAATGTTTACCATGAAGATAAACTGTTCCT 1330      1340

GACTTTATACTATTTTGAATTC

EcoRI
```

FIG.9C

```
                              N33GCR-f
       10         20         30  |      40         50         60
GAATTCGGGC GGCCGCGGCC CGGGTCCCTC GCAAAGCCGC TGCCATCCCG GAGGGCCCAG
CTTAAGCCCG CCGGCGCCGG GCCCAGGGAG CGTTTCGGCG ACGGTAGGGC CTCCCGGGTC 70         80         90        100        110        120
CCAGCGGGCT CCCGGAGGCT GGCCGGGCAG GCGTGGTGCG CGGTAGGAGC TGGGCGCGCA
GGTCGCCCGA GGGCCTCCGA CCGGCCCGTC CGCACCACGC GCCATCCTCG ACCCGCGCGT 130        140        150        160        170        180
CGGCTACCGC GCGTGGAGGA GACACTGCCC TGCCGCGATG GGGGCCCGGG GCGCTCCTTC
GCCGATGGCG CGCACCTCCT CTGTGACGGG ACGGCGCTAC CCCCGGGCCC CGCGAGGAAG
                                        START 190        200        210        220        230        240
ACGCCGTAGG CAAGCGGGGC GGCGGCTGCG GTACCTGCCC ACCGGGAGCT TTCCCTTCCT
TGCGGCATCC GTTCGCCCCG CCGCCGACGC CATGGACGGG TGGCCCTCGA AAGGGAAGGA 250        260        270        280        290        300
TCTCCTGCTG CTGCTGCTCT GCATCCAGCT CGGGGGAGGA CAGAAGAAAA AGGAGAATCT
AGAGGACGAC GACGACGAGA CGTAGGTCGA GCCCCCTCCT GTCTTCTTTT TCCTCTTAGA
           N33GEX-f
      310   |     320        330        340        350        360
TTTAGCTGAA AAAGTAGAGC AGCTGATGGA ATGGAGTTCC AGACGCTCAA TCTTCCGAAT
AAATCGACTT TTTCATCTCG TCGACTACCT TACCTCAAGG TCTGCGAGTT AGAAGGCTTA 370        380        390        400        410        420
GAATGGTGAT AAATTCCGAA AATTTATAAA GGCACCACCT CGAAACTATT CCATGATTGT
CTTACCACTA TTTAAGGCTT TTAAATATTT CCGTGGTGGA GCTTTGATAA GGTACTAACA
                                                         N33GCR-r
      430        440        450        460        470        480
TATGTTCACT GCTCTTCAGC CTCAGCGGCA GTGTTCTGTG TGCAGGCAAG CTAATGAAGA
ATACAAGTGA CGAGAAGTCG GAGTCGCCGT CACAAGACAC ACGTCCGTTC GATTACTTCT 490        500        510        520        530        540
ATATCAAATA CTGGCGAACT CCTGGCGCTA TTCATCTGCT TTTTGTAACA AGCTCTTCTT
TATAGTTTAT GACCGCTTGA GGACCGCGAT AAGTAGACGA AAAACATTGT TCGAGAAGAA
                                        N33BP5-f
      550        560        570        580 |      590        600
CAGTATGGTG GACTATGATG AGGGACAGA CGTTTTTCAG CAGCTCAACA TGAACTCTGC
GTCATACCAC CTGATACTAC TCCCCTGTCT GCAAAAGTC GTCGAGTTGT ACTTGAGACG 610        620        630        640        650        660
TCCTACATTC ATGCATTTTC CTCCAAAAGG CAGACCTAAG AGAGCTGATA CTTTTGACCT
AGGATGTAAG TACGTAAAAG GAGGTTTTCC GTCTGGATTC TCTCGACTAT GAAAACTGGA 670        680        690        700        710        720
CCAAAGAATT GGATTTGCAG CTGAGCAACT AGCAAAGTGG ATTGCTGACA GAACGGATGT
GGTTTCTTAA CCTAAACGTC GACTCGTTGA TCGTTTCACC TAACGACTGT CTTGCCTACA 730        740        750        760        770        780
TCATATTCGG GTTTTCAGAC CACCCAACTA CTCTGGTACC ATTGCTTTGG CCCTGTTAGT
AGTATAAGCC CAAAAGTCTG GTGGGTTGAT GAGACCATGG TAACGAAACC GGGACAATCA
N33BP7-f
    |  790        800        810        820        830        840
GTCGCTTGTT GGAGGTTTGC TTTATTTGAG AAGGAACAAC TTGGAGTTCA TCTATAACAA
CAGCGAACAA CCTCCAAACG AAATAAACTC TTCCTTGTTG AACCTCAAGT AGATATTGTT 850        860        870        880        890        900
GACTGGTTGG GCCATGGTGT CTCTGTGTAT AGTCTTTGCT ATGACTTCTG GCCAGATGTG
CTGACCAACC CGGTACCACA GAGACACATA TCAGAAACGA TACTGAAGAC CGGTCTACAC
         N33-f
      910  |      920        930        940        950        960
GAACCATATC CGTGGACCTC CATATGCTCA TAAGAACCCA CACAATGGAC AAGTGAGCTA
CTTGGTATAG GCACCTGGAG GTATACGAGT ATTCTTGGGT GTGTTACCTG TTCACTCGAT
```

FIG.IOA

```
            970            980            990           1000           1010           1020
CATTCATGGG AGCAGCCAGG CTCAGTTTGT GGCAGAATCA CACATTATTC TGGTACTGAA
GTAAGTACCC TCGTCGGTCC GAGTCAAACA CCGTCTTAGT GTGTAATAAG ACCATGACTT 1030           1040           1050           1060           1070           1080
TGCCGCTATC ACCATGGGGA TGGTCTCTCT AAATGAAGCA GCAACTTCGA AAGGCGATGT
ACGGCGATAG TGGTACCCCT ACCAAGAGAA TTTACTTCGT CGTTGAAGCT TTCCGCTACA 1090           1100           1110           1120           1130           1140
TGGAAAAAGA CGGATAATTT GCCTAGTGGG ATTGGGCCTG GTGGTCTTCT TCTTCAGTTT
ACCTTTTTCT GCCTATTAAA CGGATCACCC TAACCCGGAC CACCAGAAGA AGAAGTCAAA 1150           1160           1170           1180           1190           1200
TCTACTTTCA ATATTTCGTT CCAAGTACCA CGGCTATCCT TATAGTGATC TGGACTTTGA
AGATGAAAGT TATAAAGCAA GGTTCATGGT GCCGATAGGA ATATCACTAG ACCTGAAACT

STEP 1     1210           1220           1230           1240           1250           1260
GTGAAGAT GTGATTTGGA CCATGGCACT TAAAAACTCT ATAACCCTCAG CTTTTAATT  ─ 65-bp SEQUENCE
CACTCTTCTA CACTAAACCT GGTACCGTGA ATTTTTGAGA TATTGGAGTC GAAAATTAA    ABSENT IN SHORTER
STEP 2                                                              mRNA FORM 2
           1270           1280           1290           1300           1310           1320
AATGAAGCC AAGTGGGATT TGCATAAAGT GAATGTTTAC CATGAAGATA AACTGTCCT   C IN N33C(7)
TTTACTTCGG TTCACCCTAA ACGTATTTCA CTTACAAATG GTACTTCTAT TTGACAAGGA G 1330           1340           1350           1360           1370           1380
GACTTTGAAT TATTTTGAAT TC........
CTGAAACTTA ATAAAACTTA AG........

FIG.10B
```

|    | 1 Frame |       | 2 Frame |       | 3 Frame |       |
|----|---------|-------|---------|-------|---------|-------|
|    | Init.   | Term. | Init.   | Term. | Init.   | Term. |
| 1  | 5'      | 187   | 5'      | 104   | 5'      | 303   |
| 2  | 5'      | 307   | 158     | 1202  | 5'      | 315   |
| 3  | 331     | 367   | 326     | 1202  | 5'      | 324   |
| 4  | 331     | 370   | 359     | 1202  | 5'      | 360   |
| 5  | 331'    | 472   | 413     | 1202  | 363     | 387   |
| 6  | 331     | 475   | 422     | 1202  | 363     | 414   |
| 7  | 331     | 526   | 545     | 1202  | 474     | 591   |
| 8  | 331     | 556   | 590     | 1202  | 555     | 591   |
| 9  | 331     | 559   | 611     | 1202  | 558     | 591   |
| 10 | 331     | 637   | 854     | 1202  | 558     | 690   |
| 11 | 331     | 646   | 881     | 1202  | 717     | 777   |
| 12 | 331     | 655   | 896     | 1202  | 717     | 807   |
| 13 | 331     | 682   | 1034    | 1202  | 717     | 870   |
| 14 | 331     | 706   | 1040    | 1202  | 717     | 882   |
| 15 | 331     | 835   | 1223    | 1256  | 924     | 954   |
| 16 | 331     | 931   | 1223    | 3'    | 945     | 954   |
| 17 | 331     | 1054  |         |       | 966     | 1017  |
| 18 | 331     | 1183  |         |       | 1020    | 1050  |
| 19 | 331     | 1186  |         |       | 1053    | 1095  |
| 20 | 331     | 1198  |         |       | 1077    | 1095  |
| 21 | 331     | 1231  |         |       | 1077    | 1104  |
| 22 | 331     | 1264  |         |       | 1209    | 1212  |
| 23 | 331     | 1285  |         |       | 1209    | 1242  |
| 24 | 331     | 1303  |         |       | 1209    | 1260  |
| 25 | 331     | 1309  |         |       | 1263    | 1290  |
| 26 | 331     | 1336  |         |       | 1293    | 1320  |
| 27 | 331     | 3'    |         |       | 1302    | 1320  |
| 28 |         |       |         |       | 1302    | 3'    |

FIG. 11

```
                166             175             184             193             202             211
5' ATG GGG GCC CGG GGC GCT CCT TCA CGC CGT AGG CAA GCG GGG CGG CGG CTG CGG
   --- --- --- --- --- --- --- --- --- --- --- --- --- --- --- --- --- ---
   Met Gly Ala Arg Gly Ala Pro Ser Arg Arg Arg Gln Ala Gly Arg Arg Leu Arg 220             229             238             247             256             265
   TAC CTG CCC ACC GGG AGC TTT CCC TTC CTT CTC CTG CTG CTG CTG CTC TGC ATC
   --- --- --- --- --- --- --- --- --- --- --- --- --- --- --- --- --- ---
   Tyr Leu Pro Thr Gly Ser Phe Pro Phe Leu Leu Leu Leu Leu Leu Leu Cys Ile 274             283             292             301             310             319
   CAG CTC GGG GGA GGA CAG AAG AAA AAG GAG AAT CTT TTA GCT GAA AAA GTA GAG
   --- --- --- --- --- --- --- --- --- --- --- --- --- --- --- --- --- ---
   Gln Leu Gly Gly Gly Gln Lys Lys Lys Glu Asn Leu Leu Ala Glu Lys Val Glu 328             337             346             355             364             373
   CAG CTG ATG GAA TGG AGT TCC AGA CGC TCA ATC TTC CGA ATG AAT GGT GAT AAA
   --- --- --- --- --- --- --- --- --- --- --- --- --- --- --- --- --- ---
   Gln Leu Met Glu Trp Ser Ser Arg Arg Ser Ile Phe Arg Met Asn Gly Asp Lys 382             391             400             409             418             427
   TTC CGA AAA TTT ATA AAG GCA CCA CCT CGA AAC TAT TCC ATG ATT GTT ATG TTC
   --- --- --- --- --- --- --- --- --- --- --- --- --- --- --- --- --- ---
   Phe Arg Lys Phe Ile Lys Ala Pro Pro Arg Asn Tyr Ser Met Ile Val Met Phe 436             445             454             463             472             481
   ACT GCT CTT CAG CCT CAG CGG CAG TGT TCT GTG TGC AGG CAA GCT AAT GAA GAA
   --- --- --- --- --- --- --- --- --- --- --- --- --- --- --- --- --- ---
   Thr Ala Leu Gln Pro Gln Arg Gln Cys Ser Val Cys Arg Gln Ala Asn Glu Glu 490             499             508             517             526             535
   TAT CAA ATA CTG GCG AAC TCC TGG CGC TAT TCA TCT GCT TTT TGT AAC AAG CTC
   --- --- --- --- --- --- --- --- --- --- --- --- --- --- --- --- --- ---
   Tyr Gln Ile Leu Ala Asn Ser Trp Arg Tyr Ser Ser Ala Phe Cys Asn Lys Leu 544             553             562             571             580             589
   TTC TTC AGT ATG GTG GAC TAT GAT GAG GGG ACA GAC GTT TTT CAG CAG CTC AAC
   --- --- --- --- --- --- --- --- --- --- --- --- --- --- --- --- --- ---
   Phe Phe Ser Met Val Asp Tyr Asp Glu Gly Thr Asp Val Phe Gln Gln Leu Asn 598             607             616             625             634             643
   ATG AAC TCT GCT CCT ACA TTC ATG CAT TTT CCT CCA AAA GGC AGA CCT AAG AGA
   --- --- --- --- --- --- --- --- --- --- --- --- --- --- --- --- --- ---
   Met Asn Ser Ala Pro Thr Phe Met His Phe Pro Pro Lys Gly Arg Pro Lys Arg 652             661             670             679             688             697
   GCT GAT ACT TTT GAC CTC CAA AGA ATT GGA TTT GCA GCT GAG CAA CTA GCA AAG
   --- --- --- --- --- --- --- --- --- --- --- --- --- --- --- --- --- ---
   Ala Asp Thr Phe Asp Leu Gln Arg Ile Gly Phe Ala Ala Glu Gln Leu Ala Lys 706             715             724             733             742             751
   TGG ATT GCT GAC AGA ACG GAT GTT CAT ATT CGG GTT TTC AGA CCA CCC AAC TAC
   --- --- --- --- --- --- --- --- --- --- --- --- --- --- --- --- --- ---
   Trp Ile Ala Asp Arg Thr Asp Val His Ile Arg Val Phe Arg Pro Pro Asn Tyr 760             769             778             787             796             805
   TCT GGT ACC ATT GCT TTG GCC CTG TTA GTG TCG CTT GTT GGA GGT TTG CTT TAT
   --- --- --- --- --- --- --- --- --- --- --- --- --- --- --- --- --- ---
   Ser Gly Thr Ile Ala Leu Ala Leu Leu Val Ser Leu Val Gly Gly Leu Leu Tyr
```

FIG. 12A

```
        814         823         832         841         850         859
TTG AGA AGG AAC AAC TTG GAG TTC ATC TAT AAC AAG ACT GGT TGG GCC ATG GTG
--- --- --- --- --- --- --- --- --- --- --- --- --- --- --- --- --- ---
Leu Arg Arg Asn Asn Leu Glu Phe Ile Tyr Asn Lys Thr Gly Trp Ala Met Val 868         877         886         895         904         913
TCT CTG TGT ATA GTC TTT GCT ATG ACT TCT GGC CAG ATG TGG AAC CAT ATC CGT
--- --- --- --- --- --- --- --- --- --- --- --- --- --- --- --- --- ---
Ser Leu Cys Ile Val Phe Ala Met Thr Ser Gly Gln Met Trp Asn His Ile Arg 922         931         940         949         958         967
GGA CCT CCA TAT GCT CAT AAG AAC CCA CAC AAT GGA CAA GTG AGC TAC ATT CAT
--- --- --- --- --- --- --- --- --- --- --- --- --- --- --- --- --- ---
Gly Pro Pro Tyr Ala His Lys Asn Pro His Asn Gly Gln Val Ser Tyr Ile His 976         985         994        1003        1012        1021
GGG AGC AGC CAG GCT CAG TTT GTG GCA GAA TCA CAC ATT ATT CTG GTA CTG AAT
--- --- --- --- --- --- --- --- --- --- --- --- --- --- --- --- --- ---
Gly Ser Ser Gln Ala Gln Phe Val Ala Glu Ser His Ile Ile Leu Val Leu Asn 1030        1039        1048        1057        1066        1075
GCC GCT ATC ACC ATG GGG ATG GTT CTT CTA AAT GAA GCA GCA ACT TCG AAA GGC
--- --- --- --- --- --- --- --- --- --- --- --- --- --- --- --- --- ---
Ala Ala Ile Thr Met Gly Met Val Leu Leu Asn Glu Ala Ala Thr Ser Lys Gly 1084        1093        1102        1111        1120        1129
GAT GTT GGA AAA AGA CGG ATA ATT TGC CTA GTG GGA TTG GGC CTG GTG GTC TTC
--- --- --- --- --- --- --- --- --- --- --- --- --- --- --- --- --- ---
Asp Val Gly Lys Arg Arg Ile Ile Cys Leu Val Gly Leu Gly Leu Val Val Phe 1138        1147        1156        1165        1174        1183
TTC TTC AGT TTT CTA CTT TCA ATA TTT CGT TCC AAG TAC CAC GGC TAT CCT TAT
--- --- --- --- --- --- --- --- --- --- --- --- --- --- --- --- --- ---
Phe Phe Ser Phe Leu Leu Ser Ile Phe Arg Ser Lys Tyr His Gly Tyr Pro Tyr 1192        1201
AGT GAT CTG GAC TTT GAG TGA 3'
--- --- --- --- --- --- ---
Ser Asp Leu Asp Phe Glu ***
```

FIG. 12B

|     | 1 Frame |       | 2 Frame |       | 3 Frame |       |
|-----|---------|-------|---------|-------|---------|-------|
|     | Init.   | Term. | Init.   | Term. | Init.   | Term. |
| 1   | 5'      | 187   | 5'      | 104   | 5'      | 303   |
| 2   | 5'      | 307   | 158     | 1199  | 5'      | 315   |
| 3   | 331     | 367   | 326     | 1199  | 5'      | 324   |
| 4   | 331     | 370   | 359     | 1199  | 5'      | 360   |
| 5   | 331'    | 472   | 413     | 1199  | 363     | 387   |
| 6   | 331     | 475   | 422     | 1199  | 363     | 414   |
| 7   | 331     | 526   | 545     | 1199  | 474     | 591   |
| 8   | 331     | 556   | 590     | 1199  | 555     | 591   |
| 9   | 331     | 559   | 611     | 1199  | 558     | 591   |
| 10  | 331     | 637   | 854     | 1199  | 558     | 690   |
| 11  | 331     | 646   | 881     | 1199  | 717     | 777   |
| 12  | 331     | 655   | 896     | 1199  | 717     | 807   |
| 13  | 331     | 682   | 1034    | 1199  | 717     | 870   |
| 14  | 331     | 706   | 1040    | 1199  | 717     | 882   |
| 15  | 331     | 835   | 1040    | 1220  | 924     | 954   |
| 16  | 331     | 931   | 1040    | 1238  | 945     | 954   |
| 17  | 331     | 1054  | 1040    | 1244  | 966     | 1017  |
| 18  | 331     | 1183  | 1040    | 1271  | 1020    | 1050  |
| 19  | 331     | 1195  | 1040    | 3'    | 1053    | 1095  |
| 20  | 1198    | 1225  |         |       | 1077    | 1095  |
| 21  | 1228    | 1255  |         |       | 1077    | 1104  |
| 22  | 1237    | 1255  |         |       | 1077    | 1191  |
| 23  | 1237    | 3'    |         |       | 1077    | 3'    |

FIG. 13

```
            166             175             184             193             202             211
5' ATG GGG GCC CGG GGC GCT CCT TCA CGC CGT AGG CAA GCG GGG CGG CGG CTG CGG
   Met Gly Ala Arg Gly Ala Pro Ser Arg Arg Arg Gln Ala Gly Arg Arg Leu Arg 220             229             238             247             256             265
   TAC CTG CCC ACC GGG AGC TTT CCC TTC CTT CTC CTG CTG CTG CTC TGC ATC
   Tyr Leu Pro Thr Gly Ser Phe Pro Phe Leu Leu Leu Leu Leu Leu Cys Ile 274             283             292             301             310             319
   CAG CTC GGG GGA GGA CAG AAG AAA AAG GAG AAT CTT TTA GCT GAA AAA GTA GAG
   Gln Leu Gly Gly Gly Gln Lys Lys Lys Glu Asn Leu Leu Ala Glu Lys Val Glu 328             337             346             355             364             373
   CAG CTG ATG GAA TGG AGT TCC AGA CGC TCA ATC TTC CGA ATG AAT GGT GAT AAA
   Gln Leu Met Glu Trp Ser Ser Arg Arg Ser Ile Phe Arg Met Asn Gly Asp Lys 382             391             400             409             418             427
   TTC CGA AAA TTT ATA AAG GCA CCA CCT CGA AAC TAT TCC ATG ATT GTT ATG TTC
   Phe Arg Lys Phe Ile Lys Ala Pro Pro Arg Asn Tyr Ser Met Ile Val Met Phe 436             445             454             463             472             481
   ACT GCT CTT CAG CCT CAG CGG CAG TGT TCT GTG TGC AGG CAA GCT AAT GAA GAA
   Thr Ala Leu Gln Pro Gln Arg Gln Cys Ser Val Cys Arg Gln Ala Asn Glu Glu 490             499             508             517             526             535
   TAT CAA ATA CTG GCG AAC TCC TGG CGC TAT TCA TCT GCT TTT TGT AAC AAG CTC
   Tyr Gln Ile Leu Ala Asn Ser Trp Arg Tyr Ser Ser Ala Phe Cys Asn Lys Leu 544             553             562             571             580             589
   TTC TTC AGT ATG GTG GAC TAT GAT GAG GGG ACA GAC GTT TTT CAG CAG CTC AAC
   Phe Phe Ser Met Val Asp Tyr Asp Glu Gly Thr Asp Val Phe Gln Gln Leu Asn 598             607             616             625             634             643
   ATG AAC TCT GCT CCT ACA TTC ATG CAT TTT CCT CCA AAA GGC AGA CCT AAG AGA
   Met Asn Ser Ala Pro Thr Phe Met His Phe Pro Pro Lys Gly Arg Pro Lys Arg 652             661             670             679             688             697
   GCT GAT ACT TTT GAC CTC CAA AGA ATT GGA TTT GCA GCT GAG CAA CTA GCA AAG
   Ala Asp Thr Phe Asp Leu Gln Arg Ile Gly Phe Ala Ala Glu Gln Leu Ala Lys 706             715             724             733             742             751
   TGG ATT GCT GAC AGA ACG GAT GTT CAT ATT CGG GTT TTC AGA CCA CCC AAC TAC
   Trp Ile Ala Asp Arg Thr Asp Val His Ile Arg Val Phe Arg Pro Pro Asn Tyr 760             769             778             787             796             805
   TCT GGT ACC ATT GCT TTG GCC CTG TTA GTG TCG CTT GTT GGA GGT TTG CTT TAT
   Ser Gly Thr Ile Ala Leu Ala Leu Leu Val Ser Leu Val Gly Gly Leu Leu Tyr
```

FIG. 14A

```
          814         823         832         841         850         859
TTG AGA AGG AAC AAC TTG GAG TTC ATC TAT AAC AAG ACT GGT TGG GCC ATG GTG
--- --- --- --- --- --- --- --- --- --- --- --- --- --- --- --- --- ---
Leu Arg Arg Asn Asn Leu Glu Phe Ile Tyr Asn Lys Thr Gly Trp Ala Met Val 868         877         886         895         904         913
TCT CTG TGT ATA GTC TTT GCT ATG ACT TCT GGC CAG ATG TGG AAC CAT ATC CGT
--- --- --- --- --- --- --- --- --- --- --- --- --- --- --- --- --- ---
Ser Leu Cys Ile Val Phe Ala Met Thr Ser Gly Gln Met Trp Asn His Ile Arg 922         931         940         949         958         967
GGA CCT CCA TAT GCT CAT AAG AAC CCA CAC AAT GGA CAA GTG AGC TAC ATT CAT
--- --- --- --- --- --- --- --- --- --- --- --- --- --- --- --- --- ---
Gly Pro Pro Tyr Ala His Lys Asn Pro His Asn Gly Gln Val Ser Tyr Ile His 976         985         994        1003        1012        1021
GGG AGC AGC CAG GCT CAG TTT GTG GCA GAA TCA CAC ATT ATT CTG GTA CTG AAT
--- --- --- --- --- --- --- --- --- --- --- --- --- --- --- --- --- ---
Gly Ser Ser Gln Ala Gln Phe Val Ala Glu Ser His Ile Ile Leu Val Leu Asn 1030        1039        1048        1057        1066        1075
GCC GCT ATC ACC ATG GGG ATG GTT CTT CTA AAT GAA GCA GCA ACT TCG AAA GGC
--- --- --- --- --- --- --- --- --- --- --- --- --- --- --- --- --- ---
Ala Ala Ile Thr Met Gly Met Val Leu Leu Asn Glu Ala Ala Thr Ser Lys Gly 1084        1093        1102        1111        1120        1129
GAT GTT GGA AAA AGA CGG ATA ATT TGC CTA GTG GGA TTG GGC CTG GTG GTC TTC
--- --- --- --- --- --- --- --- --- --- --- --- --- --- --- --- --- ---
Asp Val Gly Lys Arg Arg Ile Ile Cys Leu Val Gly Leu Gly Leu Val Val Phe 1138        1147        1156        1165        1174        1183
TTC TTC AGT TTT CTA CTT TCA ATA TTT CGT TCC AAG TAC CAC GGC TAT CCT TAT
--- --- --- --- --- --- --- --- --- --- --- --- --- --- --- --- --- ---
Phe Phe Ser Phe Leu Leu Ser Ile Phe Arg Ser Lys Tyr His Gly Tyr Pro Tyr 1192        1201
AGC TTT TTA ATT AAA TGA 3'
--- --- --- --- --- ---
Ser Phe Leu Ile Lys ***
```

FIG. 14B

```
                                10         20         30         40         50
N33 Form 1        1    MGARGAPSRR RQAGRRLRYL PTGSFPFLLL LLLLCIQLGG GQKKKENLLA     50
N33 Form 2        1    MGARGAPSRR RQAGRRLRYL PTGSFPFLLL LLLLCIQLGG GQKKKENLLA     50
ZK686.3 cDNA      1    ---------- ---------- ---------- ----MLLAV  YESAQQQTLE    50

60         70         80         90        100
N33 Form 1       51    EKVEQLMEWS SRRSIFRMNG DKFRKFIKAP PRNYSMIVMF TALQPQRQCS    100
N33 Form 2       51    EKVEQLMEWS SRRSIFRMNG DKFRKFIKAP PRNYSMIVMF TALQPQRQCS    100
ZK686.3 cDNA     51    DKVQNLVDLT SRQSIVKFNM DKWKTLVRMQ PRNYSMIVMF TALSPGVQCP    100

110        120        130        140        150
N33 Form 1      101    VCRQANEEYQ ILANSWRY-S SAFCN-KLFF SMVDYDEGTD VFQQLNMNSA    150
N33 Form 2      101    VCRQANEEYQ ILANSWRY-S SAFCN-KLFF SMVDYDEGTD VFQQLNMNSA    150
ZK686.3 cDNA    101    ICKPAYDEFM IVANSHRYTS SEGDRRKVFF GIVDYEDAPQ IFQQMNLNTA    150

160        170        180        190        200
N33 Form 1      151    PTFMHFPPK- GRPKRADTFD LQRIGFAAEQ LAKWIADRTD VHIRVFRPPN    200
N33 Form 2      151    PTFMHFPPK- GRPKRADTFD LQRIGFAAEQ LAKWIADRTD VHIRVFRPPN    200
ZK686.3 cDNA    151    PILYHFGPKL GAKKRPEQMD FQRQGFDADA IGRFVADQTE VHVRVIRPPN    200

210        220        230        240        250
N33 Form 1      201    YSGTIALALL VSLVGGLLYL RRNNLEFIYN KTGWAMVSLC IVFAMTSGQM    250
N33 Form 2      201    YSGTIALALL VSLVGGLLYL RRNNLEFIYN KTGWAMVSLC IVFAMTSGQM    250
ZK686.3 cDNA    201    YTAPVVIALF VALLGMLYM  KRNSLDFLFN RTVWGFVCLA ITFIFMSGQM    250

260        270        280        290        300
N33 Form 1      251    WNHIRGPPYA HKNPHNGQVS YIHGSSQAQF VAESHIILVL NAAITMGMVL    300
N33 Form 2      251    WNHIRGPPYA HKNPHNGQVS YIHGSSQAQF VAESHIILVL NAAITMGMVL    300
ZK686.3 cDNA    251    WNHIRGPPFM ITNPNTKEPS FIHGSTQFQL IAETYIVGLL YALIAIGFIC    300

310        320        330        340        350
N33 Form 1      301    LNEAATSKGD VGKRRII--- ---------- ---CLVGLGL VVFFFSFLLS    350
N33 Form 2      301    LNEAATSKGD VGKRRII--- ---------- ---CLVGLGL VVFFFSFLLS    350
ZK686.3 cDNA    301    VNEAADQSNS KDRKNAGKKL NPLSLLINIPT NTLAIAGLVC ICVFFSFLLS    350

360        370        380        390        400
N33 Form 1      351    IFRSKYHGYP YSDLDFE*.. .......... .......... ..........    400
N33 Form 2      351    IFRSKYHGYP YSFLIK*... .......... .......... ..........    400
ZK686.3 cDNA    351    VFRSKYRGYP YSFLFA*... .......... .......... ..........    400
```

FIG.15

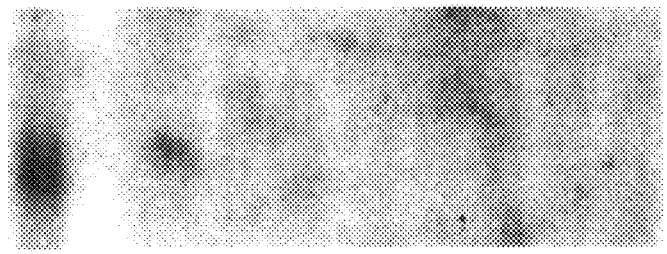
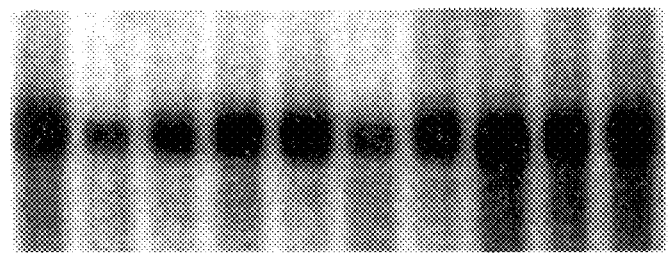
FIG.17B
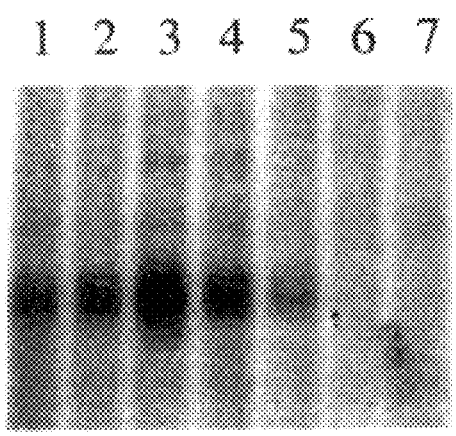
FIG.18

```
       10         20         30         40         50         60
MGARGAPSRR RQAGRRLRYL PTGSFPFLLL LLLLCIQLGG GQKKKENLLA ERVEQLMEWS 70         80         90        100        110        120
SRRSIFRMNG DKFRKFIKAP PRNYSMTVMF TALQPQRQCS VCRQANEEYQ ILANSWRYSS 130        140        150        160        170        180
AFCNKLFFSM VDYDEGTDVF QQLNNNSAPT FMHFPPKGRP KRADTFDLQR IGFAAEQLAK 190        200        210        220        230        240
WIADRTDVHI RVFRPPNYSG TIALALLVSL VGGLLYLRRN NLEPIYNKTG WAMVSLCIVF 250        260        270        280        290        300
AMTSGQMANH IRGPPYAHKN PHNGQVSYIH GSSQAQFVAE SHIILVINAA ITMGMVLLNE 310        320        330        340        350        360
AATSKGDVGK RRIICLVGLG LVVFFFSFLL SIFRSKYHGY PYSDLDFE*. ..........
```

FIG.20

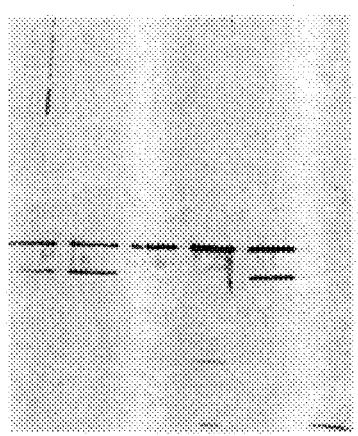

FIG.21

PROSTATE/COLON TUMOR SUPPRESSOR GENE LOCATED ON HUMAN CHROMOSOME 8

This invention is a continuation-in-part of U.S. application Ser. No. 08/246,604, filed May 20, 1994 now abandoned.

This invention was made in part with Government support under Grant Nos. CA 60358 awarded from Department of Health and Human Services and Grant Nos. CA 58236 and CA 55231, awarded from the National Cancer Institute. The government has certain rights in this invention.

Throughout this application, publications are referred to by first author name and date of publication in parenthesis. The disclosures of these publications are hereby incorporated by reference into the present application to more fully describe the state of the art to which this invention pertains.

BACKGROUND OF THE INVENTION

This invention is in the field of tumor suppressor genes (anti-oncogenes) and relates in general to products and methods for practicing broad-spectrum tumor suppressor gene therapy of various human cancers. In particular, the invention relates to methods for treating tumor cells by: (1) administering vectors comprising a nucleic acid sequence coding for the novel proteins referred to herein as prostate tumor suppressor gene products (PTSG products); or, (2) administering an effective amount of a protein coded for by the nucleic acid sequence. The invention also relates to diagnosis of certain cancers such as prostate and colon cancer using the cloned nucleic acids of this invention.

Cancers and tumors are the second most prevalent cause of death in the United States, causing 547,000 deaths per year. One in three Americans will develop cancer, and one in five will die of cancer (Scientific American Medicine, part 12, I, 1, section dated 1987). While substantial progress has been made in identifying some of the likely environmental and hereditary causes of cancer, the statistics for the cancer death rate indicate a need for substantial improvement in the therapy for cancer and related diseases and disorders.

A number of so-called cancer genes, i.e., genes that have been implicated in the etiology of cancer, have been identified in connection with hereditary forms of cancer and in a large number of well-studied tumor cells. Study of cancer genes has helped provide some understanding of the process of tumorigenesis. While a great deal more remains to be learned about cancer genes, the known cancer genes serve as useful models for understanding tumorigenesis.

Cancer genes are broadly classified into "oncogenes" which, when activated, promote tumorigenesis, and "tumor suppressor genes" which, when damaged, fail to suppress tumorigenesis. While these classifications provide a useful method for conceptualizing tumorigenesis, it is also possible that a particular gene may play differing roles depending upon the particular allelic form of that gene, its regulatory elements, the genetic background and the tissue environment in which it is operating.

One widely considered working hypothesis of cancer is as follows: (1) Most of all human cancers are genetic diseases and (2) they result from the expression and/or failure of expression of specific genes (i.e. mutant versions of normal cellular growth regulatory genes or viral or other foreign genes in mammalian cells that cause inappropriate, untimely, or ectopic expression of other classes of vital growth-regulatory genes.

A simplistic view of the biologic basis for neoplasia is that there are two major classes of cancer genes. The first class consists of mutated or otherwise aberrant alleles of normal cellular genes that are involved in the control of cellular growth or replication. These genes are the cellular protooncogenes. When mutated, they can encode new cellular functions that disrupt normal cellular growth and replication. The consequence of these changes is the production of dominantly expressed tumor phenotypes. In this model of dominantly expressed oncogenes, a view that has predominated since the emergence of the concept of the genetic and mutational basis for neoplasia, it is imagined that the persistence of a single wild-type allele is not sufficient to prevent neoplastic changes in the developmental program or the growth properties of the cell. The genetic events responsible for the activation of these oncogenes therefore might be envisioned as "single-hit" events. The activation of tumorigenic activities of the myc oncogene in Burkitt lymphoma, the expression of bcr-abl chimeric gene product in patients with chronic myelogenous leukemia, the activation of the H-ras and K-ras oncogenes in other tumors represent some of the evidence for the involvement of such transforming oncogenes in clinical human cancer. An approach to genetic-based therapy for dominantly expressed neoplastic disease presumably would require specific shutdown or inactivation of expression of the responsible gene.

Tumor suppressor genes

A more recently discovered family of cancer-related genes are the so-called tumor-suppressor genes, sometimes referred to as antioncogenes, growth-suppressor, or cancer-suppressor genes. Recent research suggests strongly that it is loss-of-function mutations in this class of genes that is likely to be involved in the development of a high percentage of human cancers; more than a dozen good candidate human tumor-suppressor genes have been identified in several human cancers. The tumor suppressor genes involved in the pathogenesis of retinoblastoma (RB), breast, and other carcinomas (p53), Wilm's tumors (wt 1, 2) and colonic carcinoma (DCC) have been identified and cloned. Some aspects of their role in human tumorigenesis have been elucidated.

The retinoblastoma gene (RB) is the prototype tumor suppressor. The RB gene encodes a nuclear protein which is phosphorylated on both serine and threonine residues in a cell cycle dependent manner (Lee et al., *Nature*, 329:642–645 (1987); Buchkovich et al., *Cell*, 58:1097–105 (1989); Chen et al., *Cell*, 58:1193–1198 (1989); DeCaprio et al., *Cell*, 58:1085–1095 (1989)). The molecular mechanisms by which RB participates in these cellular activities has not been completely elucidated. A current model holds that RB interacts with many different cellular proteins and may execute its functions through these complexes. If the function of RB protein is to maintain cells at G0/G1 stage, RB must "corral" and inactivate other proteins which are active and essential for entering G1 progression (Lee et al., *CSHSOB, LVI*:211–217 (1991)). This "corral" hypothesis is consistent with recent observations that an important growth-enhancing transcriptional factor, E2F-1, is tightly regulated by Rb in a negative fashion (Helin et al., *Cell*, 70:337–350 (1992); Kaelin et al., *Cell*, 70:351–364 (1992); Shan et al., *Mol. Cell. Biol.*, 12:5620–5631 (1992); Helin et al., *Mol. Cell. Biol.*, 13:6501–6508 (1993); Shan et al., *Mol. Cell. Biol.*, 14:229–309 (1994)). The instantly disclosed protein, PTSG, binds to the Rb protein and thus participation in the regulation of mitosis.

The familial breast cancer gene, BRCA-1, has been mapped at chromosome 17 q21–22 by linkage analysis. It is not clear whether this gene will behave as a tumor suppressor or dominant oncogene. However, the gene involved in human familial cancer syndrome such as Li-Fraumeni syndrome, p53, apparently acts as the classical tumor suppressor; similarly, the loss of RB gene is associated with hereditary retinoblastoma (Knudson, 1993, supra).

Multiple Steps and Oncogenetic Cooperation

Between these two extreme pictures of transforming oncogenes and purely recessive tumor-suppressor genes lie a number of additional mechanisms apparently involved in the development of neoplastic changes characteristic of many human tumors. It has been assumed for many years that most human cancers are likely to result from multiple interactive genetic defects, none of which alone is sufficient but all of which are required for tumor development to occur. The true roles of both the cellular protooncogenes and the growth-regulating tumor-suppressor genes in neoplasia of mammalian cells are thought to represent a complex set of interactions between these two kinds of genes.

One current theory of carcinogenesis is that for some tumorous pathologies like adenocarcinoma of the prostate, oncogenesis occurs through the selection of several genetic changes, each modifying the expression or function of genes controlling cell growth or differentiation (Nowell, P. C., *Science* 194:23–28 (1976); Weinberg, R., *Cancer Res.* 49:3713–3721 (1989)). Even though adenocarcinoma of the prostate is ranked first in incidence and second in mortality among neoplasms in men (Coffey, D. S., *Cancer* 71:880–886 (1993)), little is known of the molecular basis of this common disease. For example, genetic alterations in colon cancer have been extensively studied and a model has been proposed in which the activation of oncogenes and loss of function of tumor suppressor genes is correlated with progressive clinical and histopathological changes observed during colorectal carcinogenesis (Fearon, E. R. and Vogelstein, B., *Cell* 61:759–767 (1990)). Indeed, a similar process of progressive genetic changes has been suggested to occur in prostate cancer (Isaacs, W. B. and Carter, B. S., *Cancer Surveys*, vol. 11, Cold Spring Harbor Laboratory, Cold Spring Harbor, N.Y., pp. 15–24 (1991)) but the exact location and mechanism of underlying genetic alteration remains unknown.

Known cancer genes have been shown not to be primarily responsible for prostate cancer. For example, mutations of cancer genes such as ras oncogenes or the tumor suppressor gene p53 have been found in only a small fraction (<10%) of early prostatic tumors (Carter et al., *Proc. Natl. Acad. Sci. U.S.A.*, 87:8751–8755 (1990); Gumerlock et al., *Cancer Res.* 51:1632–1637 (1991); Bookstein et al., *Cancer Res.* 53:3369–3373 (1993)); however, mutations of the latter have been detected in 20–25% of late-stage primary tumors, suggesting that the p53 gene can participate in one of several alternative pathways of prostate tumor progression (Bookstein et al., *Cancer Res.* 53:3369–3373 (1993)).

Karyotyping and allelotyping of tumor cells also has been used to try to find the genetic mechanisms responsible for prostate cancer. Cytogenetic studies of short-term cultures of primary prostatic cancers have disclosed several consistent chromosomal aberrations such as deletion of chromosomes 1p, 7q, or 10g (Atkin, N. B. and Baker, M. C., *Hum. Genet.*, 70:359–364 (1985); Gibas et al., *Cancer Genet. Cytogenet.* 16:301–304 (1985); Lundgren et al., *Genes Chrom. Cancer,* 4:16–24 (1992)), whereas studies of allelic loss have suggested a somewhat different set of frequently lost chromosomal regions. Carter et al., *Proc. Natl. Acad. Sci. U.S.A.* 87:8751–8755 (1990), first reported non-random losses of chromosomes 10g and 16q each in ~30% of 28 tumors, and Kunimi et al., *Genomics* 11:530–536 (1991), showed losses of these same regions as well as of the p arms of chromosomes 8 and 10 at rates exceeding 50% in their set of 18 tumors.

Allelic loss of chromosome 8p is detected in 65% of prostate carcinomas, the highest rate of any chromosome arm. These rates compare to those of allelic losses of Rb in retinoblastoma, 100% of which have Rb mutation, and suggest the inactivation of a tumor suppressor gene in 8p. Interestingly, karyotypic deletion of 8p has been noted in androgen-unresponsive sublines of cell line LNCaP. No previously cloned suppressor genes are located in 8p.

In the study of Bergerheim et al. (Bergerheim et al., *Genes Chromosom. Cancer* 3:215–220 (1991)), alleles of the NEFL locus on chromosome 8p12–p22 were lost from tumors in 7 out of 8 informative patients, and those of the lipoprotein lipase locus (8p22) were lost in 6 out of 7 patients. Alleles of the PLAT locus (8p12-q11) were retained in some tumors losing more distal 8p loci, implying that the putative suppressor locus is located on 8p distal to PLAT. The most distal marker, D8S7, was lost in 3 out of 6 tumors. The exceptionally high rates of allelic loss of LPL and NEFL, and the failure to observe allelic losses starting distal to these loci, further suggested that the suppressor locus may be relatively close to LPL or NEFL.

Thus, in order to effectively diagnose susceptibility to prostate cancer and related pathologies and other related cancers, and for treatment, the locale of a tumor suppressor gene responsible for these pathologies must be identified and located. This invention satisfies this need and provides related advantages as well.

SUMMARY OF THE INVENTION

This invention is based on the discovery of a nucleic acid molecule encoding a novel prostate/colon tumor suppressor gene product (PTSG protein) having tumor suppression capability. The nucleic acid molecule has been mapped to the p22 region of chromosome 8. The expression of PTSG product in normal prostate and colon tissue, and its loss from some cases of prostate and colon cancer, support its identification as a tumor suppressor gene. The newly disclosed full length cDNAs encode two novel 348 and 347 amino acid proteins. This invention establishes for the first time that inactivation of PTSG or PTSG product is responsible for prostate adenocarcinoma, colon cancer and other related cancerous pathologies, as provided herein.

Diagnostic methods using the nucleic acid and PTSG are disclosed. In one embodiment, oligonucleotide fragments capable of hybridizing with the PTSG gene, and assays utilizing such fragments, are provided. These oligonucleotides can contain as few as 5 nucleotides, while those consisting of about 20 to about 30 oligonucleotides being preferred. These oligonucleotides may optionally be labelled with radioisotopes (such as tritium, $^{32}$phosphorus and $^{35}$sulfur), enzymes (e.g., alkaline phosphatase and horse radish peroxidase), fluorescent compounds (for example, fluorescein, Ethidium, terbium chelate) or chemiluminsecent compounds (such as the acridinium esters, isoluminol, and the like). These and other labels, such as the ones discussed in "Non-isotopic DNA Probe Techniques", L. J. Kricka, Ed., Academic Press, New York, 1992, (herein incorporated by reference,) can be used with the instant oligonucleotides. They may be used in DNA probe assays in conventional formats, such as Southern and northern blotting. Descriptions of such conventional formats can be found, for example, in "Nucleic Acid Hybridization—A Practical Approach", B. D. Hames and S. J. Higgins, Eds., IRL Press, Washington, D.C., 1985, herein incorporated by reference. Preferably these probes capable of hybridizing with the PTSG gene under stringent conditions. The oligonucleotides can also be used as primers in polymerase chain reaction techniques, as techniques are described in, for example, "PCR Technology", H. A. Ehrlich, Ed., Stockton Press, New York, 1989, and similar references.

According to the diagnostic method of the present invention, loss of the wild-type PTSG is detected. The loss may be due to either deletional and/or point mutational events. The PTSG alleles which are not deleted can be screened for point mutations, such as missense, and frame-shift mutations. Both of these types of mutations would lead to non-functional PTSG products. In addition, point mutational events may occur in regulatory regions, such as in the promoter of the PTSG leading to loss or diminution of expression of the PTSG mRNA.

In order to detect the loss of the PTSG wild-type in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. If the tumor tissue is highly contaminated with normal cells, detection of mutations is more difficult.

Detection of point mutations may be accomplished by molecular cloning of the PTSG allele (or alleles) present in the tumor tissue and sequencing that allele(s) using techniques well known in the art. Alternatively, the polymerase chain reaction can be used to amplify PTSG sequences directly from a genomic DNA preparation from the tumor tissue. The DNA sequence of the amplified sequence can then be determined. The polymerase chain reaction itself is well known in the art. See e.g., Saiki et al., *Science*, 239:487 (1988); U.S. Pat. No. 4,683,203; and U.S. Pat. No. 4,683,195.

Specific deletions of PTSG can also be detected. For example, restriction fragment length polymorphism (RFLP) probes for the PTSG or surrounding marker genes can be used to score loss of PTSG allele. Other techniques for detecting deletions, as are known in the art can be used.

Loss of wild-type PTSG may also be detected on the basis of the loss of a wild-type expression product of the PTSG. Such expression products include both the mRNA as well as the PTSG protein product itself. Point mutations may be detected by sequencing the mRNA directly or via molecular cloning of cDNA made from the mRNA. The sequence of the cloned cDNA can be determined using DNA sequencing techniques which are well known in the art. The cDNA can also be sequenced via the polymerase chain reaction (PCR) which will be discussed in more detail below.

Alternatively, mismatch detection can be used to detect point mutations in the PTSG or its mRNA product. While these techniques are less sensitive than sequencing, they are simpler to perform on a large number of tumors. An example of a mismatch cleavage technique is the RNase protection method, which is described in detail in Winter et al., *Proc. Natl. Acad. Sci. USA*, 82:7575 (1985) and Meyers et al., *Science* 230:1242 (1985). In the practice of the present invention the method involves the use of a labeled RNA probe which is complementary to the human wild-type PTSG. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the PTSG mRNA or DNA. The riboprobe need not be the full length of the PTSG mRNA or gene but can be a segment of either. If the riboprobe comprises only a segment of the PTSG mRNA or gene it will be desirable to use a number of these probes to screen the whole mRNA sequence for mismatches.

In a similar fashion, DNA probes can be used to detect mismatches, through enzymatic or chemical cleavage. See, e.g., Cotton et al., *Proc. Natl. Acad. Sci. USA*, 85:4397 (1988); and Shenk et al., *Proc. Natl. Acad. Sci. USA*, 72:989 (1975). Alternatively, mismatches can be detected by shifts in the electrophoretic mobility of mismatched duplexes relative to matched duplexes. See, e.g., Cariello, *Human Genetics*, 42:726 (1988). With either riboprobes or DNA probes, the cellular mRNA or DNA which might contain a mutation can be amplified using PCR (see below) before hybridization.

DNA sequences of the PTSG from the tumor tissue which have been amplified by use of polymerase chain reaction may also be screened using allele-specific probes. These probes are nucleic acid oligomers, each of which contains a region of the PTSG sequence DNA sequence harboring a known mutation. For example, one oligomer may be about 30 nucleotides in length, corresponding to a portion of the PTSG DNA sequence. At the position coding for the 175th codon of the oligomer encodes an alanine, rather than the wild-type codon valine. By use of a battery of such allele-specific probes, the PCR amplification products can be screened to identify the presence of a previously identified mutation in the PTSG. Hybridization of allele-specific probes with amplified PTSG sequences can be performed, for example, on a nylon filter. Hybridization to a particular probe indicates the presence of the same mutation in the tumor tissue as in the allele-specific probe.

The kit of the present invention is useful for determination of the nucleotide sequence of the PTSG using the polymerase chain reaction. The kit comprises a set of pairs of single stranded DNA primers which can be annealed to sequences within or surrounding the PTSG in order to prime amplifying DNA synthesis of the PTSG itself. The complete set allows synthesis of all of the nucleotides of the PTSG coding sequences. The set of primers may or may not allow synthesis of both intron and exon sequences. However, it should allow synthesis of all exon sequences.

The present invention is also directed to the administration of wild-type PTSG tumor suppressor gene or protein to suppress, eradicate or reverse the neoplastic phenotype in established cancer cells having no endogenous wild-type PTSG protein. The wild-type PTSG gene can be used to suppress or reverse the neoplastic phenotype or properties of established human cancer cells lacking wild-type PTSG protein. This suppression of the neoplastic phenotype in turn suppressed or eradicated the abnormal mass of such cancer cells, i.e. tumors, which in turn can reduce the burden of such tumors on the animal which in turn can increase the survival of the treated animals. The neoplastic properties which are monitored and reversed included the morphology, growth, and most significantly, the tumorigenicity of cancer cells lacking the normal PTSG protein. Thus, the "reduction of the burden of tumor cells" in an animal is a consequence of the "suppression of the neoplastic phenotype" following the administration of wild-type PTSG product tumor suppressor gene. "Neoplastic phenotype" is understood to refer to the phenotypic changes in cellular characteristics such as morphology, growth rate (e.g., doubling time), saturation density, soft agar colony formation, and tumorigenicity.

Therefore, the invention provides PTSG encoding vectors and PTSG proteins for use in treatment of tumors or cancers, and methods of preparing PTSG proteins and vectors suitable for use in methods of treatment. The invention also provides methods for assaying for molecules which bind to and effect PTSG.

The invention also provides methods of treatment for mammals such as humans, as well as methods of treating abnormally proliferating cells, such as cancer, such as prostate tumors and colon cancer or other tumor cells or suppressing the neoplastic phenotype. Broadly, the invention contemplates treating abnormally proliferating cells, or mammals having a disease characterized by abnormally proliferating cells by any suitable method known to permit a host cells compatible-PTSG encoding vector or a PTSG protein derivative to enter the cells to be treated so that suppression of one or more characteristics of the neoplastic phenotype or suppression of proliferation is achieved.

In one embodiment, the invention comprises a method of treating a disease characterized by abnormally proliferating cells, in a mammal, by administering an expression vector coding for PTSG to the mammal having a disease characterized by abnormal proliferating cells, inserting the expression vector into the abnormally proliferating cells, and expressing PTSG in the abnormally proliferating cells in an amount effective to suppress proliferation of those cells. The expression vector is inserted into the abnormally proliferating cells by viral infection or transduction, liposome-mediated transfection, polybrene-mediated transfection, $CaPO_4$ mediated transfection and electroporation. The treatment is repeated as needed.

In another embodiment, the invention comprises a method of treating abnormally proliferating cells of a mammal by inserting a PTSG encoding expression vector into the abnormally proliferating cells and expressing PTSG product therein in amounts effective to suppress proliferation of those cells. The treatment is repeated as needed.

In another alternative embodiment, the invention provides a DNA molecule able to suppress growth of an abnormally proliferating cell. An example of a prostate/colon tumor suppressor protein is PTSG protein product having an amino acid sequence substantially according to SEQ ID NO. 56. In a more preferred embodiment, the DNA molecule has the DNA sequence of SEQ ID NO. 55, and is expressed by an expression vector. The expression vector may be any host cell-compatible vector. The vector is preferably selected from the group consisting of a retroviral vector, an adenoviral vector and a herpesviral vector. In another more preferred embodiment, the DNA molecule has the DNA sequence of SEQ. ID No. 57, and is expressed by an expression vector. The expression vector may be any host cell-compatible vector. The vector is preferably selected from the group consisting of a retroviral vector, an adenoviral vector and a herpes viral vector.

In another alternative embodiment, the invention provides a PTSG protein product having an amino acid sequence substantially according to SEQ ID NO. 2 and biologically active fragments thereof. In yet another alternative embodiment, the invention provides a PTSG protein having an amino acid sequence substantially according to SEQ. ID No. 4 and biologically active fragments thereof.

In another alterative embodiment, the invention provides a method of producing a PTSG protein product by the steps of: inserting a compatible expression vector comprising a PTSG encoding gene into a host cell and causing the host cell to express PTSG protein.

In another alternative embodiment, the invention comprises a method of treating abnormally proliferating cells of a mammal ex vivo by the steps of: removing a tissue sample in need of treatment from a mammal, the tissue sample comprising abnormally proliferating cells; contacting the tissue sample in need of treatment with an effective dose of an PTSG encoding expression vector; expressing the PTSG in the abnormally proliferating cells in amounts effective to suppress proliferation of the abnormally proliferating cells. The treatment is repeated as necessary; and the treated tissue sample is returned to the original or another mammal. Preferably, the tissue treated ex vivo is blood or bone marrow tissue.

In another alternative embodiment, the invention comprises a method of treating a disease characterized by abnormal cellular proliferation in a mammal by a process comprising the steps of administering PTSG protein to a mammal having a disease characterized by abnormally proliferating cells, such that the PTSG protein is inserted into the abnormally proliferating cells in amounts effective to suppress abnormal proliferation of the cells. In a preferred embodiment, the PTSG protein fragments or derivatives thereof is liposome encapsulated for insertion into cells to be treated. The treatment is repeated as necessary.

BRIEF DESCRIPTION OF FIGURES

FIG. 5. Yeast artificial chromosome and radiation hybrid map of loci in chromosome band 8p22, a common region of allelic loss in multiple human cancers. *Genomics* 24:317–323.

FIG. 6 shows homologous integration of the conversion vector, which results in amplification of a 1855 bp band.

FIG. 7 shows the Southern blot of yeast DNA with radiolabeled hygro-gene probe that confirms the presence of the hygro$^R$ gene in the YAC arm.

FIGS. 9A–C. Nucleotide sequence and selected restriction sites of the insert of plasmid pBS-N33C(7), derived by cloning into pBluescript the 1.3 kb EcoRI-EcoRI insert from lambda phage clone λN33C (SEQ ID NO. 52), which was obtained by screening a human placenta cDNA library with selected cDNA probe N33. Selected restriction sites are shown. The first ~20 bp of sequence containing the Not I site are presumably artificially introduced during cDNA library construction.

FIGS. 10A–B. Annotated double stranded sequence (SEQ ID NO. 53–54) of N33 cDNA deduced from sequencing phage clone N33C(7) and RT-PCR clones A4 and A5. A 65-bp segment from nt 1186 to 1250 of N33C(7) and A4 sequence is absent from the A5 clone, so N33C(7) and A4 clones represent the longer Form 1 whereas A5 represents the shorter Form 2 mRNA. The presumptive alternative splice results in the utilization of either of two translational stop sites as indicated. The predicted translational start site is also shown preceded by an in-frame stop codon (*).

FIG. 11. ORF map for clone N33C(7) representing mRNA form 1. The longest ORF is nt 158–1202.

FIGS. 12A–B. Translation of longest ORF from mRNA form 1 (SEQ ID NO. 55). The predicted 348 amino-acid polypeptide has MW 39674.13 daltons (SEQ ID NO. 56). The last 5 amino acids differ from the form 2 polypeptide.

FIG. 13. ORF map for deduced mRNA form 2. The longest ORF is nt 158–1199.

FIGS. 14A–B. Translation of longest ORF from mRNA form 2 (SEQ. ID NO 57). The predicted 347 amino-acid polypeptide has MW 39556.18 daltons (SEQ ID NO. 58). The last four amino acids diverge from the form 1 polypeptide.

FIG. 15. Alignment of N33 form 1 and 2 polypeptides (SEQ ID NOS: 56 and 58) with hypothetical 37.7 kD protein encoded by (SEQ ID NO. 59) ORF ZK686.3 from *C. elegans*. Four gaps were introduced into N33 to optimize alignment. 42% of residues were identical between human and *C. elegans* (underlined). The protein encoded by ORF ZK686.3 has MW 37.7 kD.

FIGS. 17A–B. Northern blot of mRNA from human tumor cell lines hybridized with selected cDNA probes N33, P10, J2 and P16. Actin was used as a control for mRNA loading. N33 expression was not detected in 13 out of 14 colorectal carcinoma cell lines (SW480, SW837, SW1417, HT-29, SW403, LS174T, DLD-1, CACO-2, EB, SK-CO-1, RKO, HCT116 and COLO-302).

FIG. 18. Northern blot of mRNA from tumor lines PPC-1, WI-38, H460, A549 (lanes 1–4), normal colonic mucosa (lane 5), and colon tumor lines SW837 and SW480 (lanes 6 and 7). N33 is expressed in mucosa dissected from colon.

FIG. 20. Predicted sequence of N33 form 1 polypeptide (SEQ ID NO: 56). The conserved C-terminal 16 amino acids (boxed) was coupled to KLH and used to generate a rabbit polyclonal antibody.

FIG. 21. Antibody recognition of an N33-glutathione-S-transferase fusion protein in *E. coli*. N33 RT-PCR products from placenta mRNA (primers N33GEX-f and -r) were cloned into pGEX-2T (Pharmacia). Clones A4 and A5 were isolated representing form 1 and form 2 mRNAs, respectively. Protein expression was induced by IPTG and cell lysates were separated by PAGE and transferred to membrane. The Western blot was incubated with affinity-purified polyclonal anti-N33 peptide antibody, and reactive bands were visualized by an alkaline-phosphatase conjugated secondary antibody and NBT/BCIP substrate. A fusion protein band of ~57 kD was detected in induced cells containing clone A4 but not A5 or other clones.

DETAILED DESCRIPTION OF THE INVENTION

Figure 1:
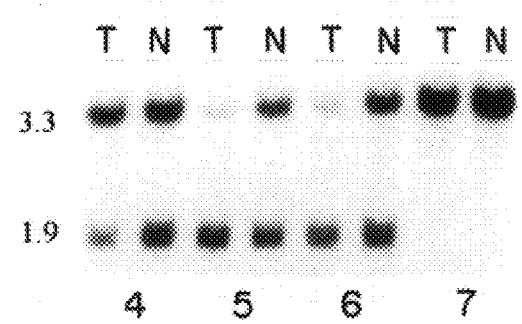
FIG. 1 shows KSR2 (8p22) Southern analysis in human prostate cancer. Paired purified prostate cancer DNA (T) and noncancerous DNA (N) from the same patients. The 1.9-kilobase allele is lost in the tumor tissue of patient 4, the 3.3-kilobase allele is lost in the tumor tissues of patients 5 and 6. Patient 7 is not informative at this locus.

This invention provides a novel gene encoding a protein referred to as PTSG protein. PTSG refers to two proteins: one composed of 348 amino acids and a second of 347 amino acids, each having a molecular weight of approximately 40 kD.

As used herein, "nucleic acid" shall mean single and double stranded genomic DNA, cDNA, mRNA and cRNA. "Isolated" when used to describe the state of the nucleic acids, denotes the nucleic acids free of at least a portion of the molecules associated with or occurring with the nucleic acid in its native environment.

Also provided by this invention is a recombinant expression vector or a recombinant replication vector comprising an isolated nucleic acid molecule corresponding to a tumor suppressor gene as well as host cells, e.g., bacterial cells, containing these vectors.

The treatment of human disease by gene transfer has now moved from the theoretical to the practical realm. The first human gene therapy trail was begun in September 1990 and involved transfer of the adenosine deaminase (ADA) gene into lymphocytes of a patient having an otherwise lethal defect in this enzyme, which produces immune deficiency. The results of this initial trial have been very encouraging and have helped to stimulate further clinical trials (Culver, K. W., Anderson, W. F., Blaese, R. M., *Hum. Gene. Ther.*, 2:107 (1991)).

So far most of the approved gene transfer trials in human rely on retroviral vectors for gene transduction. Retroviral vectors in this context are retroviruses from which all viral genes have been removed or altered so that no viral proteins are made in cells infected with the vector. Viral replication functions are provided by the use of retrovirus 'packaging' cells that produce all of the viral proteins but that do not produce infectious virus. Introduction of the retroviral vector DNA into packaging cells results in production of virions that carry vector RNA and can infect target cells, but no further virus spread occurs after infection. To distinguish this process from a natural virus infection. To distinguish this process from a natural virus infection where the virus continues to replicate and spread, the term transduction rather than infection is after used.

For the purpose of illustration only, a delivery system for insertion of a nucleic acid is a replication-incompetent retroviral vector. As used herein, the term "retroviral" includes, but is not limited to, a vector or delivery vehicle having the ability to selectively target and introduce the nucleic acid into dividing cells. As used herein, the terms "replication-incompetent" is defined as the inability to produce viral proteins, precluding spread of the vector in the infected host cell.

Another example of a replication-incompetent retroviral vector is LNL6 (Miller, A. D. et al., *BioTechniques* 7:980–990 (1989)), incorporated herein by reference. The methodology of using replication-incompetent retroviruses for retroviral-mediated gene transfer of gene markers is well established (Correll, P. H. et al., *Proc. Natl. Acad. Sci. U.S.A.* 86:8912 (1989); Bordignon, C. et al., *Proc. Natl. Acad. Sci. U.S.A.* 86:8912–8952 (1989); Culver, K. et al., *Proc. Natl. Acad. Sci. U.S.A.* 88:3155 (1991); Rill, D. R. et al., *Blood* 79(10):2694–2700 (1991)), each incorporated herein by reference. clinical investigations have shown that there are few or no adverse effects associated with the viral vectors (Anderson, *Science* 256:808–813 (1992)).

The major advantages of retroviral vectors for gene therapy are the high efficiency of gene transfer into replicating cells, the precise integration of the transferred genes into cellular DNA, and the lack of further spread of the sequences after gene transduction (Miller, A. D., *Nature*, 357:455–460 (1992)).

The potential for production of replication-competent (helper) virus during the production of retroviral vectors remains a concern, although for practical purposes this problem has been solved. So far, all FDA-approved retroviral vectors have been made by using PA317 amphotropic retrovirus packaging cells (Miller, A. D., and Buttimore, C., *Molec. Cell Biol.*, 6:2895–2902 (1986)). Use of vectors having little or no overlap with viral sequences in the PA317 cells eliminates helper virus production even by stringent assays that allow for amplification of such events (Lynch, C. M., and Miller, A. D., *J. Virol.*, 65:3887–3890 (1991)). Other packaging cell lines are available. For example, cell lines designed for separating different retroviral coding regions onto different plasmids should reduce the possibility of helper virus production by recombination. Vectors produced by such packaging cell lines may also provide an efficient system for human gene therapy (Miller, A. D., *Nature* 357:455–460 (1992)).

Non-retroviral vectors have been considered for use in genetic therapy. One such alternative is the adenovirus (Rosenfeld, M. A., et al., *Cell*, 68:143–155 (1992); Jaffe, H. A. et al., *Proc. Natl. Acad. Sci. USA*, 89:6482–6486 (1992)). Major advantages of adenovirus vectors are their potential to carry large segments of DNA (36 kb genome), a very high titre ($10^{11}$ ml$^{-1}$), ability to infecting tissues in situ, especially in the lung. The most striking use of this vector so far is to deliver a human cystic fibrosis transmembrane conductance regulator (CFTR) gene by intratracheal instillation to airway epithelium in cotton rats (Rosenfeld, M. A., et al., Cell, 63:143–155 (1992)). Similarly, herpes viruses may also prove valuable for human gene therapy (Wolfe, J. H., et al., *Nature Genetics* 1:379–384 (1992)). Of course, any other suitable viral vector may be used for genetic therapy with the present invention.

The other gene transfer method that has been approved by the FDA for use in humans is the transfer of plasmid DNA in liposomes directly to human cells in situ (Nabel, E. G., et al., *Science*, 249:1285–1288 (1990)). Plasmid DNA should be easy to certify for use in human gene therapy because, unlike retroviral vectors, it can be purified to homogeneity. In addition to liposome-mediated DNA transfer, several other physical DNA transfer methods such as those targeting the DNA to receptors on cells by complexing the plasmid DNA to proteins have shown promise in human gene therapy (Wu, G. Y., et al., *J. Biol. Chem.*, 266:14338–14342 (1991); Curiel, D. T., et al., *Proc. Natl. Acad, Sci. USA*, 88:8850–8854 (1991)).

The PTSG of the present invention may be placed by methods well know to the art into an expression vector such as a plasmid or viral expression vector. A plasmid expression vector may be introduced into a tumor cell by calcium phosphate transfection, liposome (for example, LIPOFECTIN)-mediated transfection, DEAE Dextran-mediated transfection, polybrene-mediated transfection, electroporation and any other method of introducing DNA into a cell.

A viral expression vector may be introduced into a target cell in an expressible form by infection or transduction. Such a viral vector includes, but is not limited to: a retrovirus, an adenovirus, a herpes virus and an avipox virus. When PTSG is expressed in any abnormally proliferating cell, the cell replication cycle is arrested, thereby resulting in senescence and cell death and ultimately, reduction in the mass of the abnormal tissue, i.e., the tumor or cancer. A vector able to introduce the gene construct into a target cell and able to express H-NUC therein in cell proliferation-suppressing amounts can be administered by any effective method.

For example, a physiologically appropriate solution containing an effective concentration of active vectors can be administered topically, intraocularly, parenterally, orally, intranasally, intravenously, intramuscularly, subcutaneously or by any other effective means. In particular, the vector may be directly injected into a target cancer or tumor tissue by a needle in amounts effective to treat the tumor cells of the target tissue.

Alternatively, a cancer or tumor present in a body cavity such as in the eyes, gastrointestinal tract, genitourinary tract (e.g., the urinary bladder), pulmonary and bronchial system and the like can receive a physiologically appropriate composition (e.g., a solution such as a saline or phosphate buffer, a suspension, or an emulsion, which is sterile except for the vector) containing an effective concentration of active vectors via direct injection with a needle or via a catheter or other delivery tube placed into the cancer or tumor afflicted hollow organ. Any effective imaging device such as X-ray, sonogram, or fiberoptic visualization system may be used to locate the target tissue and guide the needle or catheter tube.

In another alternative, a physiologically appropriate solution containing an effective concentration of active vectors can be administered systemically into the blood circulation to treat a cancer or tumor which cannot be directly reached or anatomically isolated.

In yet another alternative, target tumor or cancer cells can be treated by introducing PTSG protein into the cells by any known method. For example, liposomes are artificial membrane vesicles that are available to deliver drugs, proteins and plasmid vectors both in vitro or in vivo (Mannino, R. J., et al., *Biotechniques*, 6:682–690 (1988)) into target cells (Newton, A. C. and Huestis, W. H., *Biochemistry*, 27:4655–4659 (1988); Tanswell, A. K. et al., *Biochimica et Biophysica Acta* 1044:269–274 (1990)); and Ceccoll, J. et al., *Journal of Investigative Dermatology*, 93:190–194 (1989)). Thus, PTSG protein can be encapsulated at high efficiency with liposome vesicles and delivered into mammalian cells in vitro or in vivo.

Liposome-encapsulated PTSG protein may be administered topically, intraocularly, parenterally, intranasally, intratracheally, intrabronchially, means at a dose efficacious to treat the abnormally proliferating cells of the target tissue. The liposomes may be administered in any physiologically appropriate composition containing an effective concentration of encapsulated PTSG protein.

"Host-vector system" refers to host cells which have been transfected with vectors constructed using recombinant DNA techniques. Insertion of the vector or DNA can be accomplished by microcell transfer, retrovirus-mediated gene transfer, transfection, cell fusion, etc. The vectors and methods disclosed herein are suitable for use in host cells over a wide range of prokaryotic and eukaryotic organisms. Additionally, this invention provides a method of transforming a cell by contacting the cell with the vector or DNA of this invention, under suitable conditions.

Reference is made to standard textbooks of molecular biology that contain definitions and methods and means for carrying out basic techniques, encompassed by the present invention. See, for example, Maniatis et al., *Molecular Cloning: A Laboratory Manual,* Cold Spring Harbor Laboratory, New York (1989) and the various references cited therein. This reference and the cited publications are expressly incorporated by reference into this specification.

In addition, recombinant DNA methods currently used by those skilled in the art include the polymerase chain reaction (PCR) which, combined with the synthesis of oligonucleotides, allows easy reproduction of DNA sequences. A DNA segment of up to approximately 6000 base pairs in length can be amplified exponentially starting from as little as a single gene copy by means of PCR. In this technique, a denatured DNA sample is incubated with two oligonucleotide primers that direct the DNA polymerase-dependent synthesis of new complementary strands. Multiple cycles of synthesis each afford an approximate doubling of the amount of target sequence. Each cycle is controlled by varying the temperature to permit denaturation of the DNA strands, annealing the primers, and synthesizing new DNA strands. The use of a thermostable DNA polymerase eliminates the necessity of adding new enzyme for each cycle, thus permitting fully automated DNA amplification. Twenty-five amplification cycles increase the amount of target sequence by approximately $10^6$-fold. The PCR technology is the subject matter of U.S. Pat. Nos. 4,683,195, 4,800,159, 4,754,065, and 4,683,202.

It is understood that limited modifications can be made to the primary sequence of the tumor suppressor gene of this invention without destroying its biological function, and that only a portion of the entire primary structure may be required in order to effect activity. It is further understood that minor modifications of primary amino acid sequence may result in proteins which have substantially equivalent or enhanced function as compared to the molecule within the vector pBS-N33c(7). These modifications may be deliberate, as through site-directed mutagenesis, or may be accidental such as through mutation in hosts. All of these modifications are included as long as tumor suppressor function is retained. Other unique nucleic acid fragments of at least 10 nucleotides are useful as hybridization probes. The probes are useful to detect the predisposition to a cancer caused by the malfunction of this gene. The isolated nucleic acid fragments also are useful to generate novel peptides. These peptides, in turn, are useful as immunogens for the generation of polyclonal and monoclonal antibodies useful in diagnostic methods outlined below. Methods of preparing and using the probes and immunogens are well known in the art, and are briefly described below.

Also included within the scope of this invention are nucleic acid molecules that hybridize under stringent conditions to an isolated nucleic acid molecule encoding this tumor suppressor protein. Such hybridizing nucleic acid molecules or probes, can by prepared, for example, by random priming of this nucleic acid molecule. For methodology for the preparation of such fragments, see Sambrook et al. (Sambrook et al., "Molecular cloning: a laboratory manual." Cold Spring Harbor Laboratory, Cold Spring Harbor, N.Y. pp. 1.98–1.104 (1989).

Purified tumor suppressor polypeptide or protein also is provided by this invention. These polypeptides and/or proteins are useful to prepare antibodies, which in turn are useful for diagnosis. They can be produced by recombinantly expressing an isolated nucleic acid molecule of this invention using well known molecular biology techniques. "Purified", when used to describe the state of the protein, polypeptide, or antibody, denotes such protein free of a portion of the other proteins and molecules normally associated with or occurring with the tumor suppressor polypeptide, protein or antibody in its native environment. As used herein the term "native" refers to the form of a protein, polypeptide, antibody or a fragment of thereof that is isolated from nature or that which is without an intentional amino acid substitution.

As used herein, the term "antibody" or "immunoglobulin" refers to a protein that is produced in response to immunization with an antigen and specifically reacts with the antigen. This includes polyclonal as well as monoclonal antibodies. Human and mammalian, for example, mouse, rat, rabbit and goat, are intended to be included in this definition. The most predominant human antibody produced is of the IgG isotype, having two light and two heavy chains linked by disulfide bonds, which constitute about 80% of total serum antibodies.

Anti-tumor suppressor antibodies can be generated as follows. Fragments of the DNA insert in pBS-N33c(7) were fused with glutathiones S-transferase protein. The fusion proteins are then expressed in *E. coli*. Transfused *E. coli* cells are grown in LB medium plus ampicillin. The culture mixture was diluted from 1:10 to 1:150, preferably 1:100, with LB medium and ampicillin added. The procedure for recombinant plasmid construction is described in Sambrook et al. (Sambrook et al., "Molecular cloning: a laboratory manual." Cold Spring Harbor Laboratory, Cold Spring Harbor, N.Y. pp. 1.98–1.104 (1989)). The fusion of the fragments into vector frames at the site of restriction enzymes is described in *Proc. Natl. Acad. Sci.* 83:4685–4689 (1986).

Using the above described procedure for fusing GST with PTSG DNA fragment, quantities of the fusion protein were prepared and purified by preparative SDS polyacrylamide gel electrophoresis according to procedure described in Sambrook et al. (Sambrook et al., "Molecular cloning: a laboratory manual." Cold Spring Harbor Laboratory, Cold Spring Harbor, N.Y. pp. 1.98–1.104 (1989)) and Harlow and Lane (Harlow and Lane, *Antibodies, A Laboratory Manual,*

Cold Spring Harbor Laboratory, Cold Spring Harbor, N.Y. (1988)). The fusion protein is eluted by overnight extraction and SDS. Soluble acrylamide can be removed by dialysis. The proteins are then concentrated. Purified fusion protein is useful as an antigen in generating specific anti-PTSG antibody.

Rabbits can be repeatedly injected, preferably at 14 day intervals with 1–20 $\mu$g, preferably 10 $\mu$g, of purified fusion protein mixed with complete Freund's adjuvant (initial injection) and then given booster injections of the same amount of the fusion protein in incomplete Freund's adjuvant (repeated injections). Complete Freund's adjuvant generally consists of an emulsion of the antigen, in this case the fusion protein, in saline and a mixture of an emulsifying agent, such as for example Arlacel A, in mineral oil with killed mycobacteria. Incomplete Freund's adjuvant is the same except that it does not have the mycobacteria.

The injections are repeated until sufficiently high titer of anti-fusion protein is detected, approximately for two months, to react with both GST and the fusion protein. To enrich for antibodies recognizing only prostate tumor protein determinants, two or more affinity columns can be prepared using a method generally described in Harlow and Lane (Harlow and Lane, *Antibodies, A Laboratory Manual,* Cold Spring Harbor Laboratory, Cold Spring Harbor, N.Y. (1988)). At least one column is coupled with glutathione S transferase (GST) protein and at least one column is loaded with the fusion protein. Both columns are appropriately precycled. Antibody is passed first through the fusion protein-Sepharose column and eluted with glycine buffer of pH 2.3. The eluate is neutralized and passed through the GST column several times to remove antibody specifically directed against GST. The purified anti-prostate tumor suppressor protein is useful for immunoprecipitation or immunostaining, for localization of prostate tumor suppressor protein and will be equally useful for diagnostic identification of PTSG in mammalian and human tissue samples. Thus, the purified proteins also are within the scope of this invention. It can be labeled with a detectable marker such as radioisotopes, dyes, enzymes and biotin.

The above methods can be modified using any standard procedure as shown, for example, in Harlow and Lane (Harlow and Lane, *Antibodies, A Laboratory Manual,* Cold Spring Harbor Laboratory, Cold Spring Harbor, N.Y. (1988)).

The fusion proteins also can be used to generate monoclonal antibodies. Thus, this invention provides a monoclonal antibody directed to an epitope on the prostate tumor suppressor protein or polypeptide. In one embodiment of this invention, the monoclonal antibody is a mouse monoclonal antibody. In another embodiment of this invention, the monoclonal antibody is a human monoclonal antibody.

For the isolation of mouse monoclonal antibodies, eight week old mice can be injected interperitoneally with about 50 micrograms of a purified prostate tumor suppressor polypeptide (prepared as described above) in complete Freund's adjuvant 1:1 volume. Mice are then boosted, at monthly intervals, with the polypeptide, mixed with incomplete Freund's adjuvant, and bled through the tail vein. On days 4, 3 and 2 prior to fusion, mice are boosted intravenously with 50 micrograms of the polypeptide in saline. Splenocytes are fused with non-secreting myeloma cells according to procedures which have been described and are known to those of ordinary skill in the art to which this invention pertains. Some time later, approximately two weeks later, hybridoma supernatant are screened for binding activity against the prostate tumor polypeptide as described hereinafter. Positive clones are isolated and propagated.

In addition, this invention also provides the monoclonal antibody described hereinabove conjugated to a therapeutic agent. For the purposes of this invention, suitable therapeutic agents include, but are not limited to, a therapeutic agent selected from the group consisting of radioisotopes, toxins, toxoids, and chemotherapeutic agents. Also provided by this invention is the monoclonal antibody described hereinabove conjugated to a detectable marker. Suitable detectable markers include, but are not limited to, enzymes, radioisotopes, dyes, and biotin. This invention further provides monoclonal antibodies as described hereinabove conjugated to an imaging agent. Suitable imaging agents include, but are not limited to radioisotopes, such as $^{32}$P, $^{35}$S and $^{131}$I.

Also provided by this invention are pharmaceutical compositions comprising the purified prostate tumor suppressor polypeptide or protein described hereinabove alone, or conjugated to any one of the following: a detectable marker, a therapeutic agent, or an imaging agent, as described hereinabove and a pharmaceutically acceptable carrier. Further provided are pharmaceutical compositions comprising the monoclonal antibody described hereinabove alone, or conjugated to any one of the following: a detectable marker, a therapeutic agent, or an imaging agent. As used herein, the term "pharmaceutically acceptable carrier" encompasses any of the standard pharmaceutical carriers, such as phosphate buffered saline solution, water, emulsions, such as an oil/water emulsion, and various types of wetting agents.

As used herein, "antibody" also encompasses fragments of antibodies. The antibody fragments retain at least some ability to selectively bind with its antigen. Also encompassed by this invention are antibody fragments that have been recombinantly or chemically synthesized that retain the ability to bind the antigen of the corresponding native antibody. The ability to bind with an antigen or hapten is determined by antigen-binding assays known in the art such as antibody capture assays (See, for example, Harlow and Lane, (Harlow and Lane, *Antibodies, A Laboratory Manual,* Cold Spring Harbor Laboratory, Cold Spring Harbor, N.Y. (1988)). Antibody fragments retaining some binding affinity include, but are not limited to: Fab (the fragment which contains a monovalent antigen-binding fragment of an antibody molecule produced by digestion with the enzyme papain to yield an intact light chain and a portion of one heavy chain); Fab' (the fragment of an antibody molecule obtained by treating with pepsin, followed by reduction, to yield an intact light chain and a portion of the heavy chain; two Fab' fragments are obtained per antibody molecule); (Fab')$_2$, the fragment of the antibody that is obtained by treating with the enzyme pepsin without subsequent reduction; F(ab')$_2$ is a dimer of two Fab' fragments held together by two disulfide bonds; Fv and single chain antibodies (SCA). Also within the scope of this invention are CDR grafted and chimeric antibodies retaining the ability to bind prostate tumor suppressor protein.

As used herein the term "chimeric antibody" refers to an antibody in which the variable regions of antibodies derived from one species are combined with the constant regions of antibodies derived from a different species. Chimeric antibodies are constructed by recombinant DNA technology, and are described in Shaw et al., *J. Immun.* 138:4538 (1987), Sun, L. K. et al., *Proc. Natl. Acad. Sci. USA* 84:214–218 (1987); Neuberger, M. S. et al., *Nature* 314:268 (1985), Boulianne, G. L. et al., *Nature* 312:643–646 (1984); and Morrison, S. L. et al., *Proc. Natl. Acad. Sci. USA,* 81:6851–6855 (1984), for example.

As used herein the term "CDR grafted" antibody refers to an antibody having an amino acid sequence in which at least parts of one or more CDR sequences in the light and/or variable domain have been replaced by analogous parts of CDR sequences from an antibody having a different binding specificity for a given hapten or antigen. The analogous CDR sequences are said to be "grafted" onto the substrate or recipient antibody (see European Patent Publication No. 0 239 400). The "donor" antibody is the antibody providing the CDR sequence, and the antibody receiving the substituted sequences is the "substrate" antibody.

A method of detecting the presence or absence, in a sample, of a protein, the absence of which is associated with a neoplasm, is provided by this invention. For detection of protein, the method will include cell staining with polyclonal or monoclonal antibodies raised against the protein. For example, this method comprises the steps of obtaining a suitable sample from a subject. Suitable samples include, but are not limited to: prostate tumor tissue, colon tumor tissue, lymph node tissue and bone marrow cells. The method requires contacting the sample with an agent specifically unique to the tumor suppressor protein under conditions favoring the formation of a complex with the agent then detecting the presence of any complex formed. The absence of complex indicating the absence of a protein, which is associated with a neoplastic state such as prostate adenocarcinoma. Thus, this method is useful to diagnose prostate adenocarcinoma. For the purposes of this invention, suitable labeling agents are radioisotopes such as $^{32}$p, $^{35}$S and $^{131}$I, but also includes, but is not limited to dyes and enzymes.

For use in this method, the agent can be an antibody raised against the protein or a unique subregion of the protein, the absence of which is associated with prostate cancer.

A method of detecting the presence or absence, in a sample, of a tumor suppressor gene or nucleic acid, the absence of which is associated with a neoplasm, is provided by this invention. This method comprises the steps of obtaining a suitable sample from a subject. Detection methods for the presence of nucleic acid in cells include hybridization of a nucleic acid probe with the nucleic acid of a cell. Such techniques are accomplished by methods well-known to those skilled in the art. See, for example, Sambrook et al. (Sambrook et al., "Molecular cloning: a laboratory manual." Cold Spring Harbor Laboratory, Cold Spring Harbor, N.Y. pp. 1.98–1.104 (1989)).

Suitable samples include, but are not limited to: prostate tumor tissue, colon tumor tissue, lymph node tissue and bone marrow cells. The method requires contacting the sample with an agent specifically unique to wild-type or normal tumor suppressor gene under conditions favoring the formation of a complex with the agent then detecting the presence of any complex formed. The absence of complex indicating the absence of a wild-type gene, which is associated with a neoplastic state such as prostate adenocarcinoma. Thus, this method is useful to diagnose prostate adenocarcinoma. For the purposes of this invention, suitable detectable labels include radioisotopes e.g., $^{32}$p, $^{35}$S and $^{131}$I, and includes, but not limited to additional labeling agents, such as dyes and enzymes. The agent can be a nucleic acid molecule corresponding to the tumor suppressor protein or a unique subregion thereof.

A kit for the detection, diagnosis or prognosis of prostate cancer is provided by this invention. The kit includes the reagents useful to carry out the methods described above and instructions for their use in the methods. A kit can be used for the direct genetic detection of pathological alterations in the prostate tumor suppressor gene, and can include oligonucleotides, primers for PCR analysis, reagents for SSCP, or sequencing, for example. The kits, reagents and methods also are useful for prognosis. For example, deletion may be indicative of a less favorable prognosis for recovery.

Also within the scope of this invention are compositions containing, at least, any of the above-references nucleic acids, peptides, or antibodies. These compositions also can contain carriers or diluents such as phosphate buffered saline, emulsions or various wetting agents.

The following embodiments are intended to illustrate, not limit, the subject invention.

A. IDENTIFICATION OF ALLELIC LOSS

1. Tissue Samples

Prostate cancer tissue was obtained from patients undergoing radical prostatectomy for clinically localized prostate cancer between August 1988 and November 1994. None of the patients included in the study had been treated previously with chemotherapy or hormonal therapy. Prostate and seminal vesicle tissue was harvested and frozen at −80° C. as described in Bova, G. S. et al. (Bova, G. S. et al. "Homozygous deletion and frequent allelic loss of chromosome 8p22 loci in human prostate cancer." Cancer Res. 53:3969–3973.(1993)). Briefly, only clinically palpable tumors were eligible for the study, and only tumors palpable after surgical removal were harvested. The mean Gleason score (Meilinger, G. T. et al., (1967)) for the 42 primary tumors included in the study was 7.4±1.1 (SD) with a range of 5–9. Focal or established capsular penetration was seen in all 42 primary tumors studied, and thus all tumors studied fall into the $T_3$ category utilized in the recent tumor-nodes-metastasis classification of prostate cancer (Schroder, F. H. et al., (1992)). Histological evidence of seminal vesicle invasion was seen in association with 16 of 42 (38%) of the primary tumors included in the study. Microscopic lymph node metastases were seen in 11 of 42 (26%) of the cases included in the study.

Harvested primary tumors were mounted and 6 $\mu$m sections were stained with hematoxylin and eosin. Forty-two primary prostate adenocarcinomas which could be trimmed to yield tissue containing greater than 70% tumor nuclei were selected for DNA analysis. Metastatic prostate adenocarcinoma tissue was available in ten cases from patients found to have palpable enlarged pelvic lymph nodes at the time of intended radical prostatectomy. A frozen section taken at the time of surgery revealed metastatic adenocarcinoma and radical prostatectomy was not performed. Nodal tissue not needed for histological diagnosis was snap frozen and −80° C. and used for this study.

Paired noncancerous tissue (seminal vesicle, prostate, or blood lymphocytes) was obtained from each patient. Seminal vesicle or prostate tissue serving as source material for noncancerous DNA was examined every 300 $\mu$m by frozen section, and all tissue containing dysplastic or cancerous epithelia was rejected.

Preoperative serum prostate specific antigen levels were measured by monoclonal immunoradiometric assay (Hybritech, San Diego, Calif.).

2. DNA Preparation

Prostate specific antigen ("PSA") containing greater than 70% prostate cancer nuclei was isolated from surrounding tissue (containing benign prostate epithelia, stroma, lymphocytes, etc.) as much as possible using a cryostat sectioning technique described in Bos, J. L. et al., (1987). All prostate carcinomas studied were of the usual acinar type and were <2 cm in diameter. DNA isolation and quantification were performed as described in Carter, B. S. et al., (1990) and Burton, K., (1968).

3. Southern Analysis

Samples were cleaved with restriction endonucleases (BRL and New England Biolabs) with the buffers recommended by the supplier, using 10 units of enzyme/µg of DNA for MspI digests and 7.5 units/µg for TaqI digests. Samples were electrophoresed in 0.8% agarose gels and transferred to Nytran nylon membranes (Schleicher & Schuell) in 0.4M sodium hydroxide/0.6M sodium chloride after depurination in 0.25N HCl for 10 minutes. After covalent linking of the DNA to the membrane using UV irradiation (Stratagene), membranes were prehybridized in 10 ml 1M NaCl/1% sodium dodecyl sulfate/10% Dextran sulfate at 65° C. for 1 hour. DNA probes KSR2, NF 5.1, and MCT 128.2 were obtained from the American Type Culture Collection. Probes CI8–1, MSR-32 (MSR-macrophage scavenger receptor), CI8–319, and CI8–277 are cosmid probes that have been described in Emi, M. et al., (1993). Probes were labeled using random hexamer priming and incorporation of [$\alpha$-$^{32}$P]dCTP (Amersham) with the Klenow fragment of DNA polymerase I (Amersham). Probes CI8–1, MSR-32, CI8–319, and CI8–277 were boiled with sheared human placental DNA (Sigma), (0.2 mg/ml), cooled briefly on ice, and hybridized at 65° C. overnight. Probes KSR2, NEFL, and MCT 128.2 were boiled with 0.5 ml of 2 mg/ml denatured sonicated salmon sperm DNA, briefly cooled on ice, and hybridized at 65° C. overnight. After hybridization, membranes were washed in 0.1X standard saline-phosphate-EDTA 0.1% sodium dodecyl sulfate for 15 minutes and were subsequently exposed to Kodak XAR-5 film at -80° C. in cassettes with amplifying screens.

Allelic loss was defined as the absence of one allele in prostate tumor DNA compared to the noncancerous paired control DNA. In some cases, when there was residual signal from contaminating normal tissue, densitometry was used for analysis. A sample was scored as having allelic loss if a 60% reduction was present in the diminished allele compared to its normalized retained counterpart.

Allelic multiplication using probe MCT 128.2 was defined as an increase in intensity of greater than 100% of one of two alleles present in tumor samples, or intensity differences of greater than 100% between tumor and normal alleles in homozygous cases when prior probing of the same blots demonstrated equal loading of DNA in tumor and normal lanes.

4. Microsatellite Analysis

Sequences for lipoprotein lipase ("LPL") (GZ 14) and Mfd 199 primer sets were as previously published in Tomfohrde, J. et al., (1992). One of each pair of primers (LPL GZ 14 and Mfd 199R) was end-labeled with [$\gamma$-$^{32}$P]ATP (ICN Biomedicals) using polynucleotide kinase (Boehringer-Mannheim) and 5X kinase buffer [0.25M Tris, (pH 9.0), 50 mM MgCl$_2$, 50 mM dithiothreitol, and 0.25 mg/ml bovine serum albumin]. Six µl primer (10 µM), 2.8 µl 5X kinase buffer, 0.7 µl kinase (9 units/µl), 1.5 µl sterile deionized water, and 3.0 µl [$\gamma$-$^{32}$P]-ATP were combined and incubated at 37° C. for 1 hour. Products were purified using G-25 spin columns (Boehringer-Mannheim). One µl labeled primer was added to 1 µl unlabeled primer (10 µM), 0.5 ml deoxynucleotide triphosphate mix (equal volumes of DATP, dCTP, dGTP, and dTTP each at 10 mM), 5.5 µl sterile deionized water, and 10X Taq DNA polymerase buffer (Perkin-Elmer), 10 µl genomic DNA were added (2.5 ng/µl), and the mixture was heated to 94° C. After addition of Taq DNA polymerase solution (5 units), thermocycling was then performed with 30 cycles of denaturation at 94° C. for 30 seconds, annealing at 62° C. (LPL) or 58° C. (Mfd 199) for 30 seconds, and extension at 72° C. for 30 seconds. This was followed by 72° C. for 7 minutes. Products were then mixed with an equal volume of stop buffer containing 95% formamide, 0.05% xylene cyanol, 0.05% bromophenol blue, and 20 mM EDTA. Samples were heat denatured at 94° C. and 3-µl aliquots of each sample were loaded on 6% acrylamide gels containing 8.0M urea. Gels were dried and exposed to Kodak XAR film. In this study, allelic loss using microsatellite analysis was determined according to criteria similar to those used in Southern analysis described above.

5. Immunohistochemistry for MSR Protein

Sections of primary prostate cancer and adjacent noncancerous prostate (including areas of benign prostatic hypertrophy and normal prostate) were examined in five patients. Liver tissue from a single patient obtained at autopsy served as positive control for MSR staining. Well preserved central and peripheral zone prostate tissue was obtained from the same patient at autopsy and stained for MSR protein. This patient had no evidence of malignancy at autopsy and prostate tissue was normal on gross examination and histologically. Unfixed air-dried 6-µm frozen sections on glass slides were warmed to room temperature and fixed in 2% formaldehyde/10 mM Tris, pH 7.4/150 mM NaCl/2mM CaCl$_2$ solution for 10 minutes and then incubated for 20 minutes at room temperature in 0.3% H$_2$O$_2$/absolute methanol solution. Slides were subsequently rinsed twice with 10 mM Tris, pH 7.4/150 mM NaCl/2 mM CaCl$_2$ and then incubated at 37° C. for 10 minutes in serum blocking solution (Zymed). Rabbit anti-human synthetic scavenger receptor peptide IgG (kindly provided by Dr. Tatsuhiko Kodama, University of Tokyo and is described in Kodama et al. (1988)) was then added (1:50) to each slide and incubated at 37° C. for 30 minutes. The primary antibodies were detected with a biotinylated secondary antibody-streptavidin-peroxidase conjugate (Zymed).

6. Results

Fifty-two (52) prostate cancer specimens were examined for allelic loss using 8 polymorphic probes for the short arm of chromosome 8. Overall, 32 of 51 (63%) informative tumor specimens showed loss of at least one locus on chromosome 8p. The most frequently deleted region is observed at chromosome 8p22–21.2. Loss of one allele is identified in 14 of 23 (61%) tumors at D8S163 (12 of 19 primary tumors and 2 of 4 lymph node metastases) (FIG. 1), in 15 of 32 (47%) tumors at LPL (15 of 30 primary tumors and 0 of 2 metastases), and in 20 of 29 (69%) tumors at MSR (17 of 26 primary tumors and 3 of 3 metastases), all on 8p22. Loss of one allele is identified in 16 of 27 (59%) tumors at D8S220 (12 of 22 primary tumors and 4 of 5 metastases) on 8p21.3–21.2 (FIG. 2; Table 1).

Figure 3:
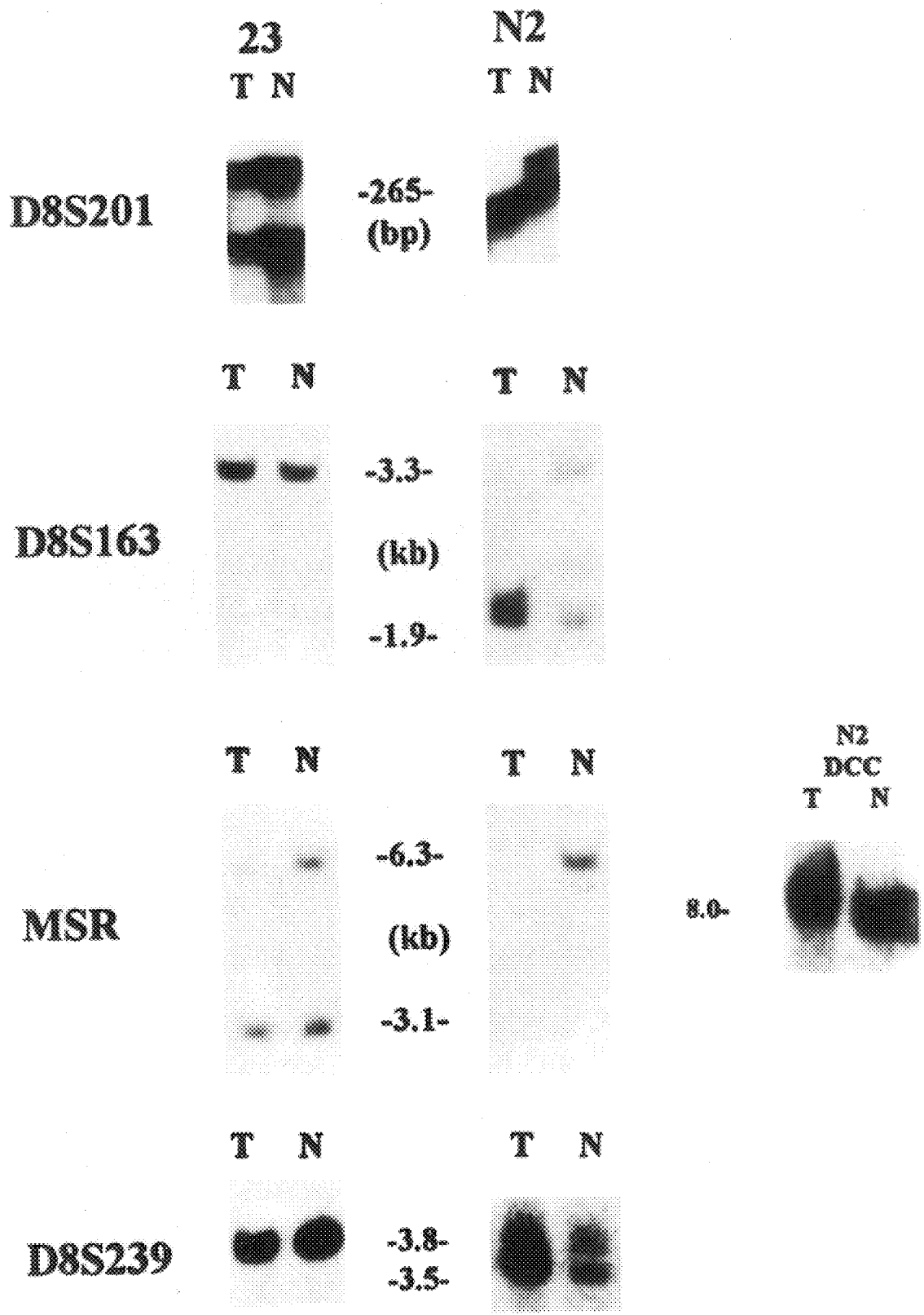
FIG. 3 shows homozygous deletion of MSR in human prostate cancer. Primary tumor 23 has retained both alleles at D8S201, is uninformative at D8S163, has lost the 6.3-kilobase allele at MSR, and is uninformative at D8S39. Metastatic tumor N2 has lost one allele at D8S201 and at D8S163, while demonstrating complete loss of sequences at MSR. Re-probing the same blot with the 15–65 probe for DCC (18q), a strong signal is obtained at 8 kilobases (kb), demonstrating the presence of high molecular weight DNA in the tumor lane. Both D8S39 alleles are present in tumor N2 and the intensity of the lower allele is multiplied 3-fold. Figure legend: bp, base pairs. For definition of T and N, see legend to FIG. 1.

In addition to loss of one allele at the MSR locus in a majority of tumors, one metastatic prostate cancer sample (N2) demonstrated homozygous deletion of MSR sequences. Hybridization of the same blot with the DCC probe 15–65 establishes the presence of intact DNA of equivalent or larger size in the N2 tumor lane (FIG. 3). Repeat digestion of N2 DNA with MspI, TaqI, and EcoRI and probing for MSR has confirmed this finding, but at least one allele is present. The boundary of the homozygous deletion is thus delimited by D8S163 and LPL.

In contrast to 8p22–21.2, loci telomeric and centromeric to this region are largely retained, with loss of one or more loci in only 9 of 48 (19%) of informative cases. Distal loci studied on 8p23 are largely retained, with loss in only 4 of 38 (11%) of informative cases at D8S140 and in only 3 of 22 (14%) of cases at D8S201 (Table 1). Loci studied on 8p11.2 and 8q24 are also infrequently deleted, with loss identified in 3 of 26 (12%) of informative cases at D8S194 and in 2 of 17 (12%) at D8S39.

Evidence of chromosome 8q multiplication was detected in 5 of 32 (16%) tumors probed at D8S39, including cases 4, 20, 21, N1, and N2 (FIG. 3). Signals for one of two D8S39 (8q24) alleles were multiplied 2–3-fold after correction for DNA loading differences. All of the tumors with 8q amplification had loss of 8p in at least one locus.

Figure 4:
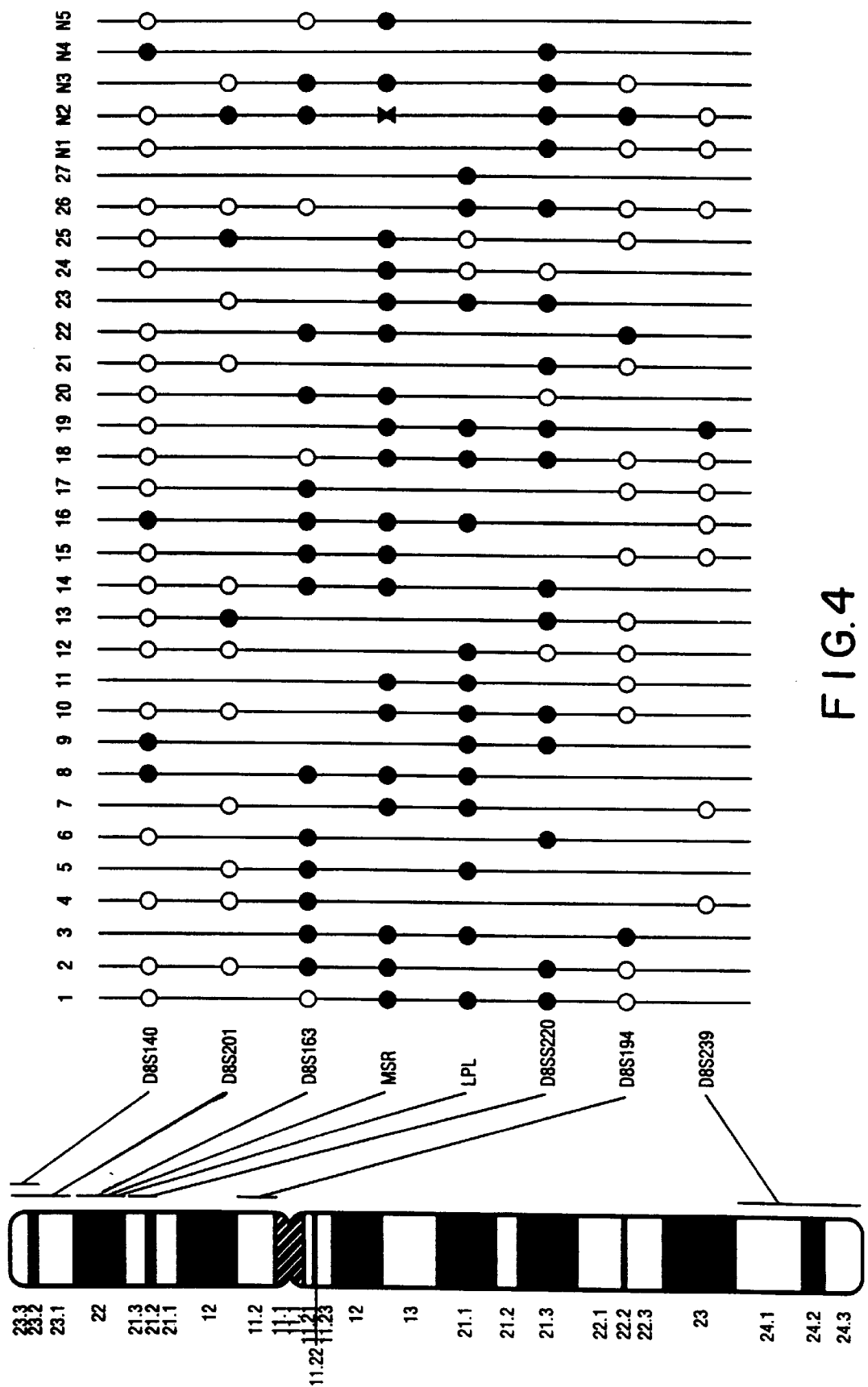
FIG. 4 shows deletion map in human prostate cancer. Only tumors demonstrating chromosome 8p loss are illustrated. Samples 1–27 are primary tumors. Figure legend: N1 through N5 are metastatic prostate cancers. ○, retained alleles, loss of heterozygosity, X, homozygous deletion.

Data from all primary and metastatic prostate cancers with demonstrated loss on chromosome 8p are summarized in FIG. 4. Fifteen of 42 (36%) primary tumors studied and 5 of 10 (50%) metastatic tumors studied demonstrated retention of heterozygosity or were not informative at the 8 loci studied on chromosome 8p and these cases are not illustrated in FIG. 4. All tumors with loss on 8p which are informative for MSR have lost at least one allele at this locus. Tumors 1, 18, 25, and N5 have retained D8S163 (KSR) but lost proximal loci including MSR. Tumors 24 and 25 have retained LPL but lost more distal loci including MSR. Those results confine the smallest region of overlap to the interval between D8S163 and LPL, flanking the MSR locus. Based on the genetic map presented by Emi et al. (1993), this interval spans 14 cM in the male.

The observation of homozygous deletion at the MSR locus prompted us to perform a preliminary assessment of the macrophage scavenger receptor gene as a possible tumor suppressor gene. Prostate tissue was analyzed for expression of MSR protein using a highly specific polyclonal antibody as described by Kodama et al. (1988). Macrophage scavenger receptor protein was not detected among prostate cancer cells or noncancerous prostate epithelia. Scattered cells contained within the stroma of each of the prostate sections stained positively, consistent with staining in macrophages only.

To determine whether allelic loss on chromosome 8p correlates significantly with clinical parameters, preoperative serum PSA levels were reviewed, Gleason scored, and final pathological staging for each patient included in the study. Mean Gleason score did not differ between the two groups, with a mean of 7.3 in patients with 8p loss, and a mean of 7.6 in those with no 8p loss demonstrated. Preoperative PSA levels were available for 34 of 42 patients whose primary prostate cancer tissue was studied. Mean PSA level for the entire group of patients was 11.2 ng/ml (range 1.6–23.6). The mean preoperative PSA level for patients with 8p loss was 12.6 ng/ml, and for patients with no loss on chromosome 8p it was 9.3 ng/ml (analysis of variance, P=0.105). Seminal vesicle invasion was observed in 11 of 27 (41%) patients with 8p loss and in 5 of 15 (33%) patients with no seminal vesicle invasion ($X^2$, P=0.055). Microscopic lymph node metastases were found in 9 of 27 (33%) of patients with 8p loss, and in 3 of 15 (20%) patients without 8p loss ($X^2$, P=0.35). In summary, there is a trend toward higher preoperative PSA levels, more frequent lymph node involvement, and more frequent seminal vesicle involvement in patients with 8p loss demonstrated within their prostate cancers, but these trends are not statistically significant.

B. ISOLATION AND MAPPING OF 8p PROBES

1. Origin of Probes. Primers and Somatic Cell Hybrids

Plasmid probe pABL4–2 detecting D8S21 was obtained from R. White and its preparation is disclosed in Tsui, L. C. et al. (1989). Its insert was partially sequenced by priming from *E. coli* amber suppressor tRNA$^{Tyr}$ using oligonucleotide (SEQ ID NO:1) 5'-GAATCCTTCCCCCAC-3', and two PCR primers were designed to create an STS (Table 2). Lambda phage CRI-R191 detecting D8S26 was obtained from the ATCC. A 4.2 kb EcoRI restriction fragment of this phage was subcloned and partially sequenced, from which an STS was designed (Table 2). Cosmid CI8–487 detecting D8S233 was obtained from the Japanese Cancer Research Resources Bank. A 2.2 kb EcoRI restriction fragment of this cosmid was subcloned and partially sequenced to create an STS (Table 2). New STSs (Table 3) were created by partially sequencing random subclones of purified YAC DNA (see below). YAC end fragments (Table 3) were obtained by the inverse PCR method of Albertsen and Thliveris (Joslyn et al., 1991). PCR products were ligated into TA cloning vector (Invitrogen) and sequenced, from which STSs were made (Table 3). The remaining primer sequences were obtained from sources indicated in Tables 2 and 3. DNA from a human chromosome 8 x CHO somatic cell hybrid mapping panel (Wagner et al., "A hybrid cell mapping panel for regional localization of probes to human chromosome 8." *Genomics* 10:114–125 (1991)) was kindly provided by M. Wagner.

2. Radiation Hybrids

A human x hamster hybrid line, GM10156b, containing human chromosome 8 as its only human component, was obtained from the NIGMS Mutant Cell Repository (Camden, N.J.). The hybrid was exposed to 5000 rads of γ radiation and fused to the APRT- and HPRT-deficient Chinese hamster ovary cell line CHO-ATS-49tg by the method of Cox et al. (Cox et al., *Science* 250:245–250 (1990)). Following HAT selection, a total of 97 hybrid clones were obtained. The presence or absence of six marker loci (D8S26, MSR, D8S233, D8S261, D8S21 and LPL) in radiation hybrid DNA was determined by PCR with relevant primers listed in Table 2. (SEQ ID NOS. 6 through 25, respectively). Distances and orders among these markers were estimated using the Statistical Package for Radiation Hybrid Mapping (Cox et al., "Radiation hybrid mapping: a somatic cell genetic method for constructing high-resolution maps of mammalian chromosome." *Science* 250:245–250.). The TWOPOINT program was used to estimate recombination fractions and retention frequencies. Trial maps were tested for support of order with the FOURPOINT program.

3. YAC Library Screening

A copy of the YAC library (Albertsen et al., *Proc. Natl. Acad. Sci. U.S.A.* 87:4256–4260 (1990)) was obtained from CEPH (Paris, France). The library was screened by PCR with ten loci listed in Table 2 by a heirarchical screening method (Green, E. D. and Olson, M. V. *Proc. Natl. Acad. Sci. U.S.A.* 87:1213–1217 (1990)). DNA pools were made from 4 plates, 8 rows and 12 columns; 58 superpools represented 384 clones each. Clones identified by plate/ row/ column address were streaked onto AHC-agar plates and confirmed by direct PCR of colonies or by PCR of yeast DNA (Ausubel et al., "Current Protocols in Molecular Biology." Greene Publishing Associates/J. Wiley & Sons, Inc., New York, N.Y. (1992)).

4. Embedding of Yeast DNA in Beads

YAC clone stocks were streaked onto AHC-agar plates. Single pink colonies were picked and grown in 5 ml of YPD media at 30° C. overnight, then expanded to 100 ml for an additional 24 hours. Yeast cells were embedded in agarose beads by the method of Overhauser and Radic (Focus 9[3]:8–9, Bethesda Research Laboratories, Inc., Gaithersburg, Md., 1987) as follows: cells were recovered by centrifugation and washed twice in 20 ml of SE (75 mM NaCl, 25 mM Na$_2$EDTA, pH 8.0), then resuspended in 4 ml SE. Cell suspensions were transferred to 125 ml Erlenmeyer flasks and warmed to 45° C. Genome-qualified low melting point agarose (1% in SE) and mineral oil were separately equilibrated to 45° C., and beakers containing 100 ml of ice-cold SE and a stir-bar were placed in ice buckets over magnetic stirrers at medium speed. Five ml of agarose were added to cells in each flask and mixed. Twenty ml of mineral oil were then added and the flask was swirled vigorously for 30 seconds to emulsify the contents, which were then poured immediately into an iced SE beaker. Beads were formed within 5 minutes. The mixture in each flask was transferred to several 50 ml centrifuge tubes and spun at low speed to separate aqueous and oil layers. Excess oil was removed and the contents respun. Residual oil, SE and floating beads were discarded and remaining beads (5–10 ml) were washed three more times with SE. The insides of tubes were wiped to remove trace oil and beads were pooled to one tube. Packed beads were resuspended in 1 volume of SE and cells were digested with 0.5 ml of 2-mercaptoethanol and 10 mg of freshly dissolved yeast lytic enzyme (70,000 U/g, ICN) per 10 ml final volume at 37° C. for 2 hours. Beads were then spun as before, resuspended in 20 ml it (w/v) sarcosyl, 25 mM $Na_2EDTA$, pH 8.0, 50 ug/ml proteinase K, and incubated overnight at 50° C. The supernatant was removed and beads were washed in 20 ml TE with 0.1 mM phenylmethylsulfonyl fluoride (PMSF) followed by two more washes in TE.

5. preparation of YAC DNA by PFGE

A 0.6-cm thick, It agarose gel in 0.5X TBE was poured in a 20 cm wide×14 cm long gel casting unit with 2 or 3 preparative wells. Wells were loaded with low-melt agarose beads containing YAC DNA and sealed with low-melt agarose. Yeast chromosomes were separated on a BioRad CHEF-DR III PFGE apparatus running at 60–120 sec switch times ramped over 24 hours at 6 V/cm at a 120° angle in 0.5X TBE at 14° C. The gel was stained in 1 µg/ml ethidium bromide in 0.5X TBE for 30 minutes and chromosomes visualized by UV irradiation. Slots 5–7 mm wide were cut parallel to and in front of each YAC to be isolated, and the gel was replace on its platform. Excess buffer and gel fragments were blotted away and slots were filled with 1% low-melt agarose (InCert, BioRad) in 0.5X TBE, which was allowed to set. The gel was replaced into the CHEF-DR III and equilibrated to 14° C. PFGE was run at a 180 seconds constant switch time for 4 hours. YAC bands were again visualized by UV illumination and cut out of the low-melt slot.

Gel slices were equilibrated with two changes of 1 X β-agarase buffer (New England Biolabs [NEBI], the buffer was removed, and slices were melted at 65–70° C. for 30 minutes. Melted slices were brought to 40° C. and incubated for 1–2 hours with β-agarase I (NEB) (5 U per gram of agarose), then chilled on ice and spun to remove undigested agarose. Supernatants were loaded onto Centricon 100 filter units (Amicon) with excess TE buffer and spun at 500 x g for 30 minutes to concentrate and purify YAC DNAs. The resulting ~80 µl preps were further concentrated to 50 µl by Speed-Vac with recovery of supernatants as the final products.

YAC DNA (~50 ng) was digested with Bgl II and ligated into BamH I-digested pBluescript (Stratagene) by standard methods (Sambrook et al.. "Molecular Cloning: A Laboratory Manual." Cold Spring Harbor Laboratory, Cold Spring Harbor, N.Y. pp. 1.98–1.104 (1989)). The ligation mix was redigested with BamH I to reduce nonrecombinant background and transformed into E. coliDH10B (GIBCO-BRL) with X-gal and IPTG for blue-white selection per supplier's recommendations. Plasmids derived from white colonies were screened for use as single-copy probes in Hind III-digested human genomic DNA (Sambrook et al., "Molecular cloning: a laboratory manual." Cold Spring Harbor Laboratory, Cold Spring Harbor, N.Y. pp. 1.98–1.104 (1989)), then mapped on somatic cell hybrids and YAC clones as follows.

6. Biotin-Labelling of YAC DNA

Isolated YAC DNA (10–20 µl) was biotin-labelled by random primer extension in the presence of biotinylated DATP (BioPrime kit, BRL) in 50 µl volumes according to kit instructions. Successful labelling was verified by running 5 µl of reaction product on agarose gels and either visualizing a faint smear by ethidium bromide and UV irradiation or by transferring the DNA onto nylon membrane by standard methods. The membrane was blocked as for a Western blot and streptavidin-conjugated alkaline phosphate was added directly without primary or secondary antibodies. The biotin-labelled DNA smear was visualized by the BCIP/NBT substrate reaction.

7. oligonucleotides for Linkers and PCR

Two oligonucleotides were synthesized, (SEQ ID NO:2) 5'-CGATCTAGACCAGCACAATGG-3' (Primer 1) and 5'-CCATTGTGCTGGTCTAGATCGCACA-3' (Primer 2). Primer 2 was 5'-phosphorylated with ATP and T4 kinase (37° C., 30 min), heated to inactivate the enzyme, and annealed to equimolar amounts of Primer 1 to form a linker

```
5'-CGATCTAGACCAGCACAATGG-3'

3'-ACACGCTAGATCTGGTCGTGTTACC-P-5'

Xba I    BstX I
``` that is blunt and phosphorylated on one end, and non-self-sticky on the other. DNA fragments flanked by these linkers are able to be PCR-amplified with Primer I.

8. Creation of Amplifiable Short-Fragment cDNA Libraries

RNA was isolated from tissues and cells using TriReagent (Molecular Research Center, Inc.) per manufacturer's instructions. Poly-A+ RNA was selected from total RNA with biotinylated oligo-dT primers and streptavidin-conjugated paramagnetic particles (PolyATtract kit, Promega). Double-stranded cDNA was made from poly-A+ RNAs and one sample of total RNA per manufacturer's instructions with random primers and M-MLV RT (RiboClone cDNA synthesis kit, Promega). A final step with T4 DNA polymerase yielded blunt-ended cDNAs. CDNA made from total RNA was set aside for later use as a probe for ribosomal DNA (rDNA). Excess linkers (see above) were ligated to the poly-A+-derived cDNAs with T4 DNA ligase. CDNA (1–5 µl) was amplified in 100 µl volumes using ~500 ng of Primer 1 and other PCR constituents at the usual concentrations. Conditions were (95°, 2.5')→(940, 40"; 600, 40"; 72°, 2.5')×20→(72°, 10'). PCR products were purified with Wizard PCR Prep spin columns (Promega) and eluted in 50 µl of 0.5 X TE. DNA was quantitated by DNA Dipstick (Invitrogen); typical yields were 500 ng of purified product per 100 ul reaction. Amplified cDNAs examined by agarose gel electrophoresis and ethidium bromide staining comprised a broad streak with maximal intensity at about 500 bp.

9. Blocking Repetitive Sequences in cDNA

Purified amplified cDNA (1–2 µg) was mixed with equal amounts (w/w) of Cot 1 DNA (GIBCO-BRL) and reaction volumes were adjusted to 80 µg/ml in 120 mM $NaPO_4$ buffer pH 7 (e.g., 50 µl of cDNA was reduced to 21 µl by SpeedVac, to which was added 1 µl Cot 1 DNA and 3 µl of 1M $NaPO_4$ pH 7; the presence of TE was ignored). Reactions were overlaid with mineral oil and heated to 100° C. for 10 minutes to denature, then incubated at 60° C. for 20 hours ($C_0t=20$)

10. Hybridization of CDNA to YACs

The method of Morgan et al. (1992) was adapted with minor modifications. Biotin-labelled YAC DNAs (100 ng or ~10 μl of labelling reaction per hybridization) were heat-denatured and loaded into Centricon 100 filter units with blocked cDNAs (1 μg excluding Cot 1 DNA) and 2 ml of 1 mM NaPO$_4$, pH 7, and spun at 1000 x g for ~25 minutes. The phosphate buffer wash was repeated once, and the retentate (60–80 μl) was collected into microfuge tubes. Volumes were reduced to ~5 μl in the SpeedVac, at which point the hybridization mixes were adjusted to 120 mM NaPO$_4$ pH 7, 1 mM EDTA pH 8, and DNA concentrations (excluding Cot 1) of ~160 μg/ml (e.g., 1.1 μg in 7 μl). Reactions were overlaid with mineral oil, then incubated at 60° C. for 60 hours (Cot=120).

11. Capture. Amplification and Cloning of Selected cDNAs

Streptavidin-conjugated paramagnetic particles (Promega) were prewashed twice with TE+1M NaCl then incubated with completed hybridization reactions in 200 μl of TE+1M NaCl at room temperature for 15 minutes.

Particles were collected magnetically and supernatants were removed. Particles were washed 5 times with 15 minutes incubations in 200 μl of 0.1 X SSC+0.1% SDS, two at room temperature, then three at 60° C., with magnetic collection between each wash. Bound cDNA was eluted from particles with 100 μl of 50 mM NaOH for 15 minutes, neutralized with 100 μl of 1M Tris-HCl pH 7.5, and transferred to clean tubes. Supernatants were desalted and concentrated using NaI and silica matrices (Geneclean kit, Bio 101) per manufacturer's instructions into 20 μl volumes of TE. These cDNAs were re-amplified exactly as for the original libraries (see above) except that 5 μl of templates were used and PCR was carried out for 30 cycles. The resulting products were purified and blocked with Cot 1 DNA exactly as above. Selection with YAC DNA was also carried out a second time as above. Second-round selected cDNAs were captured as above and amplified one more time. Final PCR products were cloned directly into T-vector (Novagen), transformants of which were plated onto Tet+ Amp LB-agar plates with X-gal and IPTG for blue-white selection per kit instructions.

12. Screening Recombinant Clones

White colonies (~75/selection) were picked with wooden toothpicks in duplicate onto two gridded Amp-agar plates, one having an overlaid circular nylon membrane and one without. A uniquely arrayed pattern of short streaks or dotted lines was created so that duplicate colonies on plates could be identified easily. After overnight growth at 37° C., the plain (master) plate was stored and the filter was lifted from the other plate and processed as for filter colony hybridization screening (Sambrook et al.. "Molecular cloning: A Laboratory Manual." Cold Spring Harbor Laboratory, Cold Spring Harbor, N.Y. pp. 1.98–1.104 (1989)) through 10% SDS, denaturation, neutralization, and 2 X SSC. Filters were baked, prewashed (pg. 1.101), prehybridized in 0.05 X BLOTTO, then hybridized either sequentially or simultaneously with nick-translated total human DNA (Alu probe) and random-primed rDNA (ribosomal DNA probe). After washing and autoradiography, hybridization-negative colonies were picked from the master plate for further characterization. Mini-scale DNA preps were prepared and analyzed by BstX I or (HindIII+EcoRI) digestion and agarose gel electrophoresis. Inserts ranged in size from 250–500 bp and were excised from low-melt agarose gels and radiolabelled by random priming. Probes were hybridized to filters containing HindIII-digested DNA from YAC clones and to triplets of human, chromosome 8 human-mouse hybrid, and mouse genomic DNA to identify single-copy probes localized to human chromosome 8.

13. YAC content mapping

About 30 random subclones (Table 6) of YACs 932_e_9, 767_h_8, 802_f_11, 832_a_10, 821_f_7, and 885_c_8 were isolated and mapped to human chromosome 8 by Southern hybridization with human chromosome 8 x mouse hybrid cell line DNA or regional panel thereof (Wagner et al., *Genomics* 10:114–125 (1991)). These probes were mapped within the YAC contig by hybridization to Hind III-digested YAC DNA blots (note: Ele=E1). Three YAC end clones (YE766, YE843 and YE932) were isolated by inverse PCR as described above from YACs 766_a_12, 843_g_3 and 932_e_9 respectively and mapped to chromosome 8 and the YAC contig as above.

The CEPH megabase YAC library (~22,000 clones) was screened by PCR with primers for six simple tandem repeat polymorphisms (STRPs) and four RFLP-containing loci on several independent linkage maps (FIG. 5, Table 2). About 30 YAC clones were identified and confirmed with the initial screens. Additional clone addresses were obtained by searching AluPCR and fingerprinting overlap tables (Cohen et al., *Science* 250:245–250 (1993)). These clones were integrated into the YAC map after being tested for STS content. A set of 31 markers was used to assemble the map, including the ten screening STSs, one additional published STRP (D8S206), two expressed sequence tags (D8S294E and D8S297E) (Adams et al., *Nature* 355:632–634 (1992)), fifteen random YAC subclones and three YAC end clones (Table 3) (SQ ID NOS. 26 through 51 respectively). PCR and Southern blotting methods were used in tandem to minimize the scoring of false positives and negatives. The YAC map was anchored to cytogenetic maps by the chromosomal location of the MSR and LPL (lipoprotein lipase) genes (8p22) (Mattei et al., *Cytogenet. Cell Genet.* 63:45–46 (1993); Emi et al., *J. Biol. Chem.* 268:2120–2125 (1993)) and by placing multiple probes in intervals A or B of the somatic cell hybrid panel described by Wagner et al. (Wagner et al., *Genomics* 10:114–125 (1991)) (Table 3), in which interval A is telomeric to interval B.

A single, large contig was formed from thirty-six YACs (Table 4, FIG. 5). Parsimonious STS content mapping dictated a unique order for all ten of the original screening markers as tel-D8S26-D8S511-D8S549 -MSR-D8S254-D8S233-D8S261-D8S21-LPL-D8S258-cen. Cosmid CI8–245 (D8S335), which comprised a centromeric boundary for one or more allelic loss regions (Ohata et al., *Genes Chronosom. Cancer* 7:85–88 (1993); Emi et al., *Genes Chromosom. Cancer* 7:152–157 (1993); Fujiwara et al., *Cancer Res.* 53:1172–1174 (1994)), was not available from the Japanese Cancer Research Resources Bank and could not be incorporated into our map. It is tightly linked to and apparently centromeric of LPL (Emi et al., *J. Biol. Chem.* 268:2120–2125 (1993a); Emi et al., *Genomics* 15:530–534 (1993)). CTSB (cathepsin B), another RFLP marker which has been mapped to 8p22–p23.1 (Fong a al., *Hum. Genet.* 89:10–12. (1992)), was placed in hybrid interval A (MacGrogan et al., *Genes Chromosom. Cancer* 10:151–159 (1994)) and excluded from the physically mapped region D8S26-D8S258 by its absence from this set of YAC clones (data not shown). Due to lack of sufficient YAC termini, we were unable to uniquely order some accessory markers such as D8S206, D8S294E, and D8S297E. As an incidental finding, probe El, a random subclone of YAC 932_e_9, detected a Hind III RFLP in human DNA with two alleles, 12 kb and (8 kb+4 kb).

YACs are subject to two kinds of rearrangement artifact, chimerism and internal deletion, which potentially can affect various aspects of physical mapping. Chimerism did not influence our STS content mapping and the derived order of loci because all markers were independently mapped to chromosome 8. Reinforcement against the effects of internal deletion was provided by the many interspersed accessory probes and by large contig depth (redundancy). For example, a large internal deletion in YAC 767_h_8 encompassing probes E15, YE766, E1, E3, MSR, and E20 was postulated in order to retain the unity of at least six other YACs. On the other hand, this apparent deletion provided two additional "endpoints" with which to resolve the orders of two marker pairs.

Figure 2:
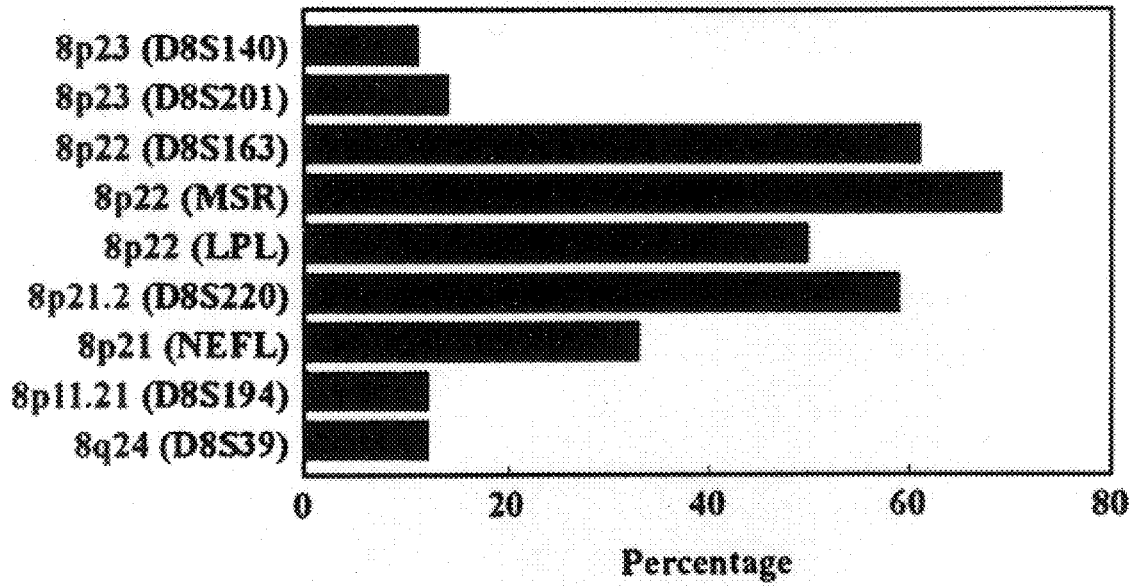
FIG. 2 shows the percentage of prostate cancers with loss at loci studied on chromosome 8.

Of the 97 radiation hybrids isolated, 17 retained one or more of the six genetic markers tested with retention frequencies for individual loci ranging from 0.12 to 0.17. At least one breakpoint was detected in 10 of 17 hybrids. Distance estimates between pairs of loci were generated by the TWOPOINT program (Table 4). The order of markers suggested by YAC mapping was tested by fourpoint analysis of the radiation hybrid data (FIG. 1). Calculated odds against inversion were greater than 1:1000 for all adjacent markers except D8S261 and D8S21, which were separated by only one breakpoint and a calculated theta value of 0.05, or 5 cRay$_{5000}$. Marker orders were therefore consistent among the genetic, YAC and radiation hybrid maps. The distance between D8S26 and LPL was ~9 cM on the genetic map and 90 cR$_{5000}$ on the radiation hybrid map, suggesting a ratio of ~10 cR$_{5000}$ per cM in this region.

B.14. Long range restriction mapping

Figure 8:
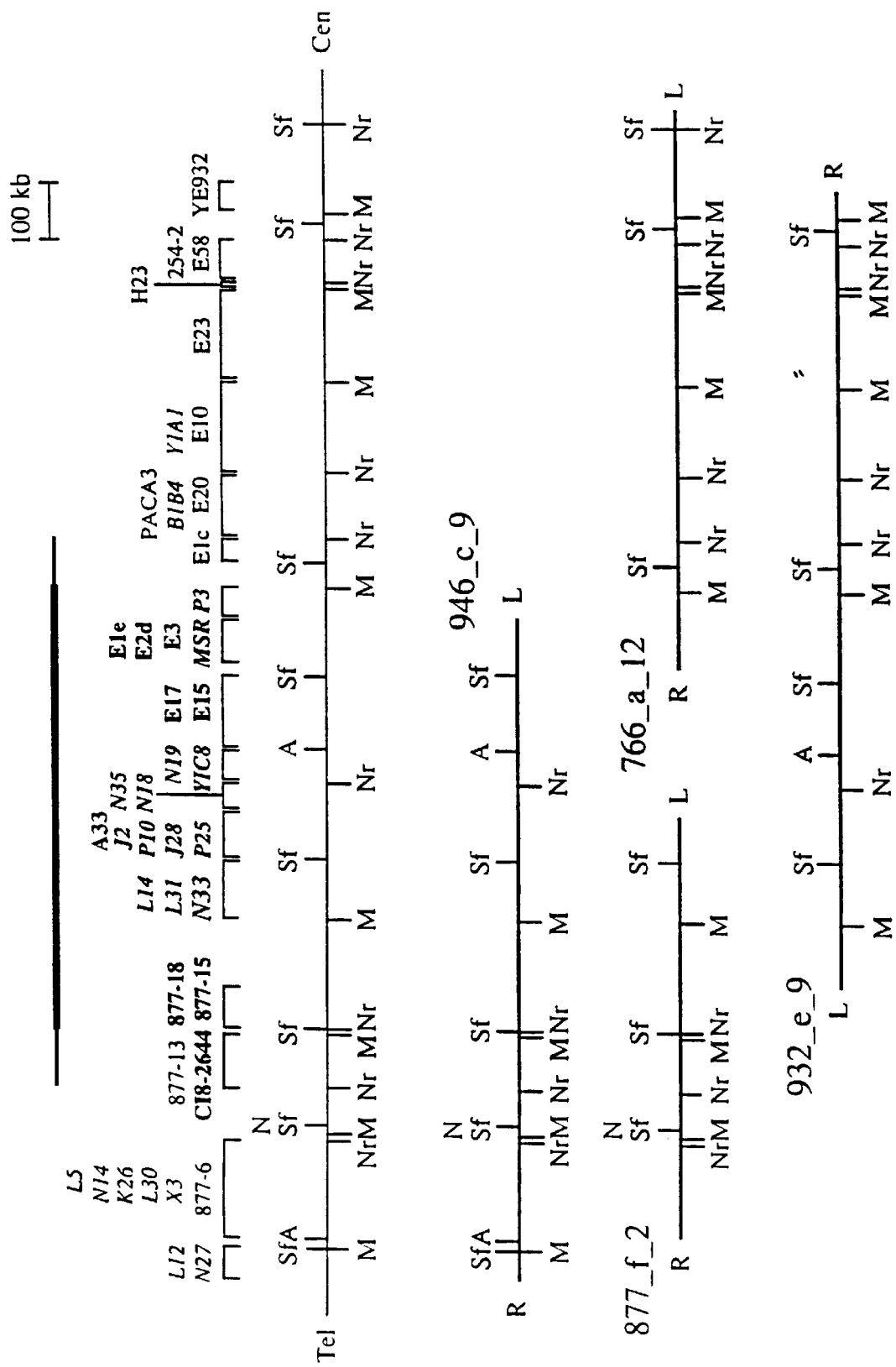
FIG. 8. Long-range restriction map of YACs encompassing markers on chromosome band 8p22. DNA from YACs 946_c_9, 877_f_2, 932_e_9, and 766_a_12 embedded in agarose beads was digested with various rare-cutting restriction enzymes (A: Asc I, M: Mlu I; N: Not I; Nr: Nru I; Sf: Sfi I) and separated by PFGE as described in Methods. Southern blotting with selected cDNA (italic) and genomic DNA roman) probes was performed to identify restriction fragments containing each probe (brackets). Probes found to be homozygously deleted in Tumor N2 (FIGS. 3 and 4) are shown in bold, and the deduced minimal (740 kb; thick line) and maximal (920 kb; thin line) extent of the deletion in this tumor is shown above. The N33 gene is located within the deletion as shown.

Forty selected cDNA fragments (Table 7) have been isolated and mapped onto human chromosome 8 and the YAC panel as above. Selection has been done with YACs 932_e_9, 802_f_11, 821_f_7, 877_f_2, and 946_C_9. A long-range restriction map of part of the 8p22 region was constructed (FIG. 8). The map encompasses at least 25 probes from Tables 6 and 7. YAC DNA was digested with various rare-cutting restriction enzymes Asc I, Mlu I, Not I, Nru I, or Sfi I and separated by PFGE as described above. Southern blotting with was performed to identify restriction fragments containing each probe. The map was assembled based on standard mapping methodologies, including analysis of partial and double-enzyme digests. One important finding to note was that cosmid CI8–2644, obtained from Dr. Y. Nakamura, was located telomeric to the MSR gene rather than centromeric as suggested by Fujiwara et al. (Fujiwara et al., *Genes Chromsom. Cancer* 10:7–14 (1994)).

15. Mapping the homozygous deletion in Tumor DNA from the single metastatic prostate tumor with a homozygous deletion of MSR (Bova et al., *Cancer Res.* 53:3869–3873 (1993)) was examined by Southern blotting analysis with numerous newly isolated genomic and selected cDNA probes in order to map the extent of this deletion. Probes found to be completely deleted in this tumor (boldface, FIG. 8) begin with MSR and extend telomerically through probes 877–15 and cCI8–2644. Markers Elc and 877–13 are the closest retained loci at the centromeric and telomeric ends, respectively. Based on the positions of lost and retained loci within mapped restriction fragments (FIG. 8), the minimum and maximum sizes of the homozygous deletion in this tumor were determined at 740 kb and 920 kb, respectively. The target tumor suppressor gene was presumptively located within this region and was inactivated by this deletion. N33 was located within this region (FIG. 8).

The mapping of cCI8–2644 to a position near the telomeric deletion boundary was significant because it suggests that the common region of allelic loss detected in colorectal, liver, and lung cancers found by Fujiwara et al. (Fujiwara et al., *Genes Chromosom. Cancer* 10:7–14 (1994) overlaps extensively with this region of homozygous deletion. Thus any gene within the homozygous deletion may also be important in these other cancers. Furthermore, the size of the allelic loss region in the latter report must be larger than that stated in the paper (600 kb) and larger than the homozygous deletion in this tumor, ie., the homozygous deletion defines the smallest known critical region containing the putative tumor suppressor gene.

16. Sequence analysis of selected cDNA fragments

Sequencing of selected CDNA probes in Table 7 revealed the following: 1) P3 and P28 are identical to the 5' end of the MSR cDNA sequence, whereas P34 is derived from the 3' untranslated region of MSR. The isolation of fragments of known genes from the region indicated that the method cDNA selection was successful. 2) J28 overlaps P27, L3 and N28 and contains a partial ORF encoding a novel predicted amino acid sequence with no close relatives in GENBANK or PIR. Other parts of his DNA sequence were nearly identical to those deposited in GENBANK by random cDNA sequencing. 3) J12 contains sequences 95% identical to that of human protein phosphatase type 2C alpha subunit, i.e., a known gene that has not yet been localized. The sequence differences were nonconservative and we suspected that J12 represented either a closely related gene or a pseudogene. We then cloned and sequenced the J12 locus at the genomic DNA level and found that it lacked introns and contained a single-base insertion that would destroy the conserved ORF. Thus we tentatively concluded that J12 was a pseudogene for human protein phosphatase type 2C alpha subunit. 4) L21, N21, N33, N36 and P14 overlap among each other and define a partial ORF with highly significant homology to a predicted gene in C. elegans identified by random sequencing of genomic cosmid or cDNA clones (SWISS-PROT P34669; GENBANK M88869, T01933, L17337; PIR S44911). The function of the *C. elegans* gene is unknown.

17. Cloning and sequencing of longer N33 cDNAs.

Based on preliminary expression data (see below), selected cDNA clone N33 was used as a probe to screen a placenta lambda phage cDNA library (Clontech). Clone λN33C was isolated and its 1.3 kb EcoRI-EcoRI insert was subcloned into pBluescript to yield pBS-N33C(7). Sequencing revealed a 1342-bp insert flanked by EcoRI sites (FIGS. 9, 10) and encoding a long ORF (nt 158–1202) (FIG. 11). Oligonucleotide primers N33GEX-f and N33GEX-r were synthesized based on this sequence (FIG. 10) and used to amplify a segment N33 mRNA by RT-PCR of placenta mRNA. Two closely-spaced specific bands of ~950 bp were detected with an abundance ratio of roughly 1:2 (upper band: lower band). In order to further characterize these bands, RT-PCR products were cloned into pGEX-2T (Pharmacia) and two clones, A4 and AS, were isolated. Clone A4 was colinear with pBS-N33C(7) whereas AS lacked nt 1186–1250 (65 bp) compared to the other clones. Consequently, we presume that N33C(7) and A4 clones represent the longer (Form 1) mRNA whereas A5 represents the shorter Form 2 mRNA. The ORFs encoded by the two forms differ over the last ~20 bp and utilize different termination codons (FIGS. 10–14). The two ORFs are identical through residue 343 then encode 4 or 5 different C-terminal amino acids each.

One other sequence feature is that nt 1252 was C in N33C(7) but T in A4 and A5 (FIG. 10). This change does not affect the Form 1 ORF encoded by N33C(7) because it occurs after stop codon 1. It is not known whether this difference represents a natural polymorphism, a cloning artifact, or a mutation in one or more of these clones.

Both N33 predicted polypeptides were highly homologous ($p<e^{-100}$) to the C. elegans predicted cDNA ZK686.3. Alignment was optimized by introducing four gaps into N33, yielding ~42% identical residues between human and C. elegans gene (FIG. 15). Three 12- to 21-residue subregions of N33 (e.g., $^{81}$PRNYSMIVMFTALQP) (residues 81–95 of SEQ ID NO: 56) retain >90% identity with ZK686.3, suggesting highly conserved functional motifs. On the other hand, the C. elegans gene lacks homologous residues of the first 35 amino acids of N33, and N33 internally lacks approximately 16 amino acids compared to ZK686.3 (FIG. 15), suggesting significant evolutionary divergence of the transcription units. N33 was not significantly related to any other sequences in GENBANK, PIR, SWISS-PROT or EMBL.

18. Expression of N33 in tissues, tumors and cultured cells.

Figure 16:
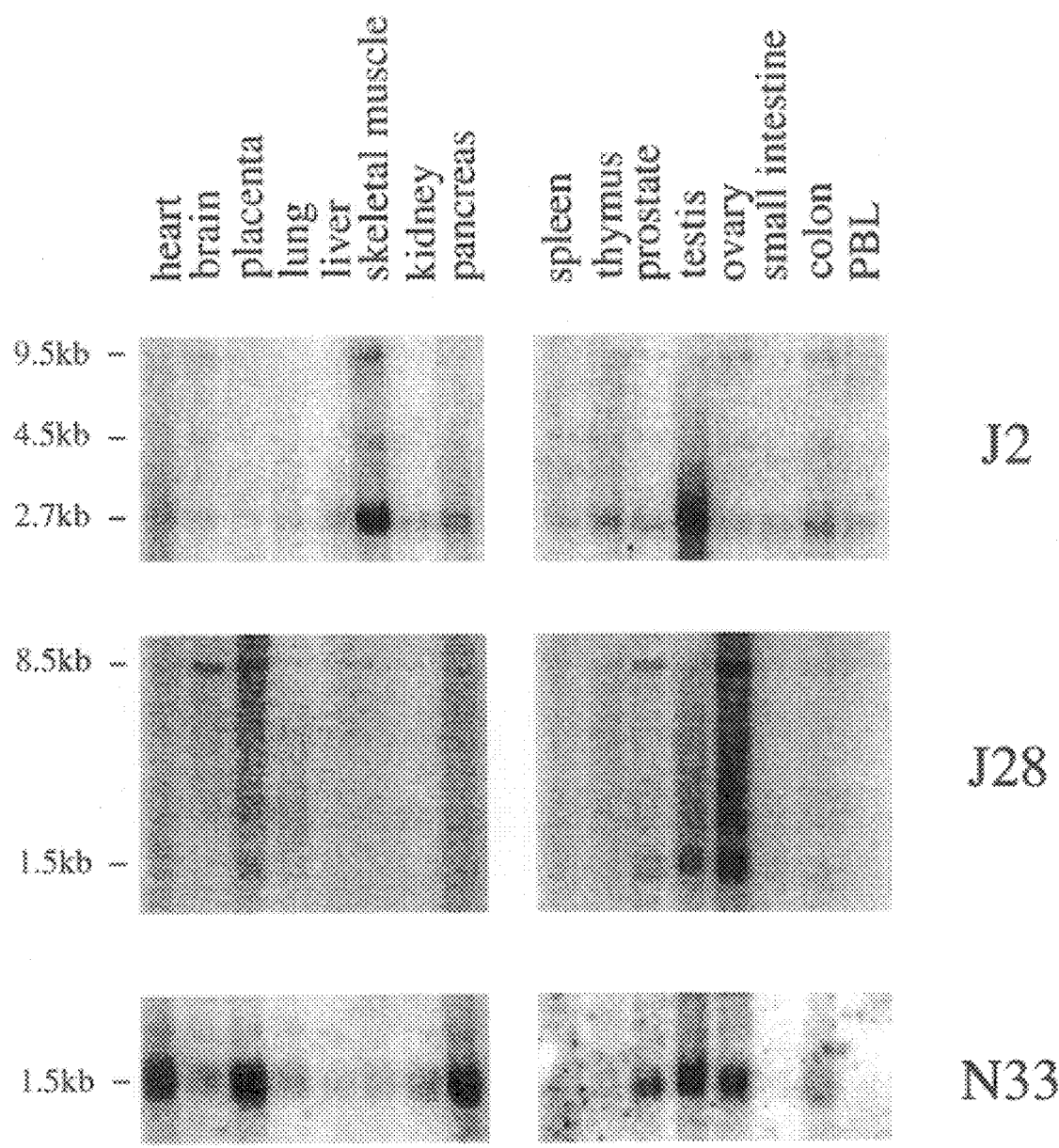
FIG. 16. Northern blot of mRNA from normal human tissues (Clontech) hybridized with selected CDNA probes J2, J28 and N33. N33 mRNA is about 1.5 kb in size and is expressed in most tissues including heart, placenta, lung, liver, pancreas, prostate, testis, ovary and colon. Expression in spleen, thymus, small intestine and peripheral lymphocytes was low.

Various selected cDNA clones were used to probe Northern blots containing mRNA from several normal human tissues, examples of which are shown in FIG. 16. A single mRNA of about 1.5 kb in size was detected with N33 probes in most tissues including heart, placenta, lung, liver, pancreas, prostate, testis, ovary and colon. Expression in spleen, thymus, small intestine and peripheral lymphocytes was low. Expression detected by another clone, J2, was seen mostly in skeletal muscle and testis, whereas two messages detected by clone J28 were found principally in placenta, testis and ovary. Expression of a tumor suppressor gene is expected in the tissues of origin of the target tumor types, so N33 but not J2 or J28 had expression patterns consistent with a suppressor gene for prostatic, colorectal and perhaps other cancers.

Figure 17A:
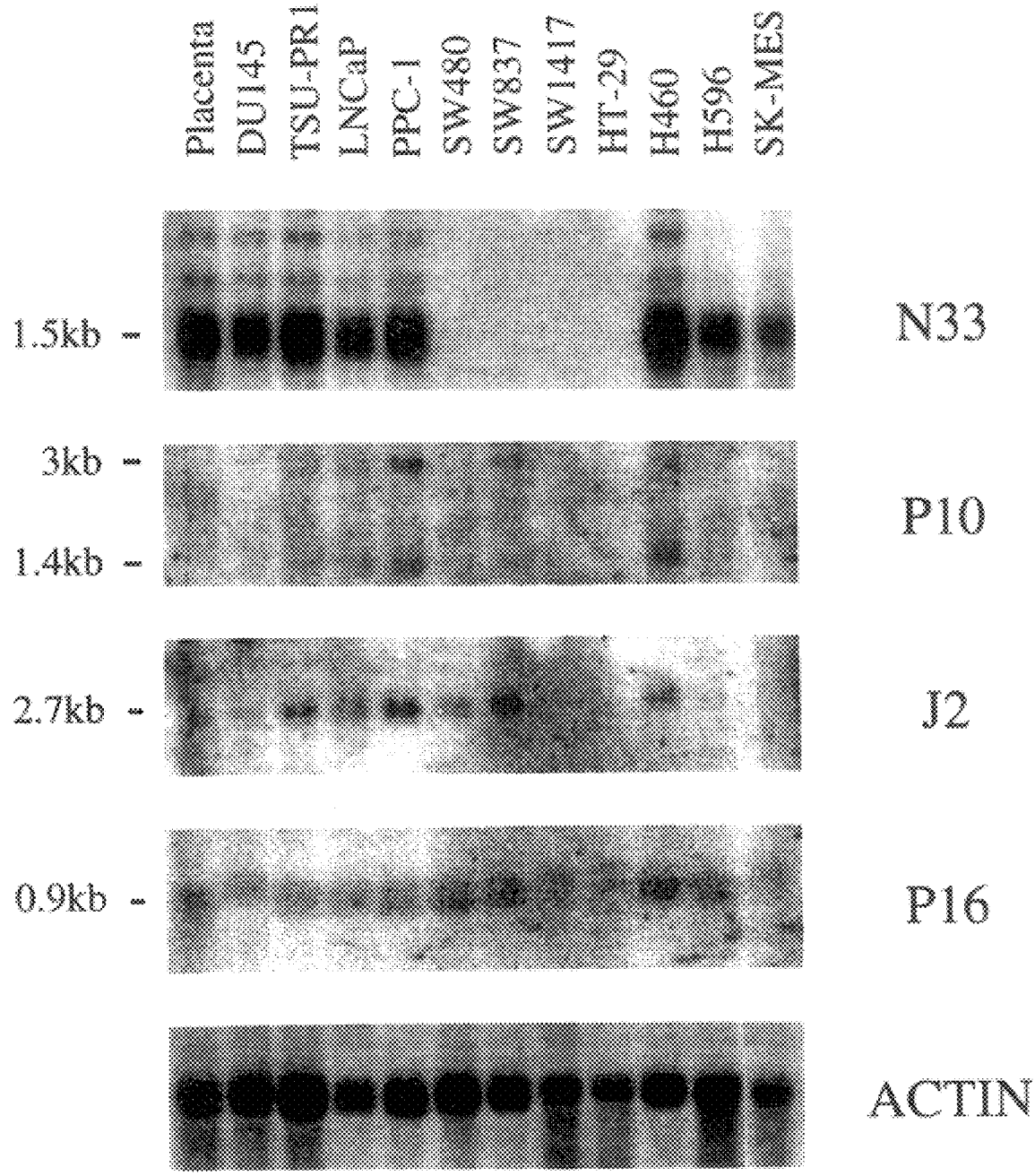
Figure 19A:
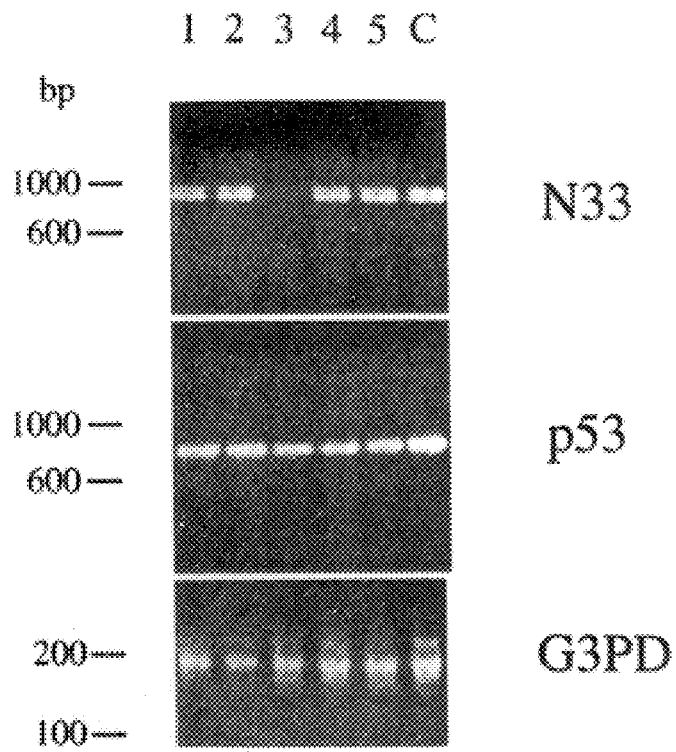
FIGS. 19A–B. RT-PCR assay for N33 expression in RNA from nine prostate cancer specimens (lanes 1–9). C: PCR control. N33 primers were N33GEX-f and -r. Primers for the p53, Rb, and G3PD genes were used as controls for RNA/cDNA quality. N33, Rb and p53 primers span exon boundaries and do not specifically amplify genomic DNA. Markedly decreased N33 expression was seen in cases 3, 6 and 9. In tissues expressing N33, both the upper (form 1) and lower (form 2) mRNAs can be seen.
Figure 19B:
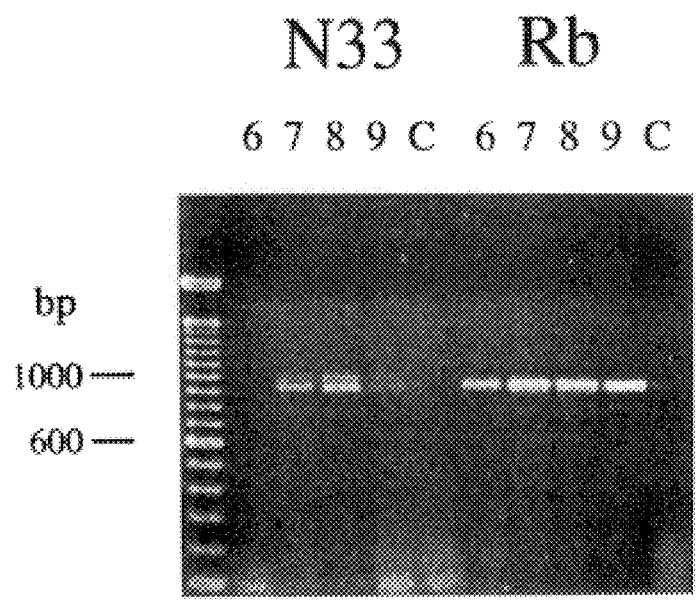

Northern analysis of mRNA from tumor cell lines showed expression of N33 in 3 of 3 prostate lines and 3 of 3 lung lines, but in only 1 out of 14 colorectal cancer cell lines (FIG. 17). In order to further determine the significance of this finding, the mucosa of a colon specimen (precursor tissue for colonic adenocarcinoma) was dissected from the colonic wall and tested for N33 mRNA, and specific expression was observed (FIG. 18, lane 5).

Finally, small amounts of total RNA were extracted from nine fresh prostate cancer samples (7 primary tumors and 2 metastases). Cryomicrotome-directed dissection was employed to reduce the numbers of contaminating nonneoplastic cells in primary specimens, but some level (typically, ~20%) of infiltrating cells was unavoidable. Because of limiting amounts of available RNA, RT-PCR with N33-specific primers was employed to quantitate N33 expression. Primers from Rb, p53 and G3PD were used to control for RNA quality and cDNA synthesis. Markedly decreased expression of N33 was observed in three cases (lanes 3, 6 and 9), where lane 6 RNA was obtained from Tumor N2 to verify the function of this assay. Lane 3 and 9 RNAs were obtained from primary tumors, in which some quantity of N33 message is expected to be contributed by nonneoplastic cells. These findings together with the lack of expression in colorectal cell lines supported the identification of N33 as a candidate prostate and colorectal tumor suppressor gene.

19. Mechanism of loss of N33 expression in tumor cells and tissues.

The basis for the lack of N33 expression in colorectal tumor cells and prostate tumor tissues is unknown, but could be due to somatic mutations (e.g., affecting mRNA expression or stability), methylation changes, or other epigenetic regulatory factors. Whereas one prostatic tumor is known to have a large homozygous deletion in band 8p22, the genetic status of additional primary and metastatic prostate and colorectal tumors are determined by several methods, as follows: 1) Southern blots of tumor DNAs are hybridized with N33 cDNA probes and other 8p22 markers to detect homozygous deletions or genetic rearrangements 2) the structure of the PTSG locus is determined by cloning/sequencing at the genomic DNA level by standard techniques. For example, a P1 clone containing the N33 gene has been isolated and is sequenced with primers from the cDNA sequence, revealing exon/intron boundaries and flanking intronic sequences. PCR primers for amplifying each exon is synthesized. Amplification and sequencing of tumor DNA is then performed to detect the presence of subtle small deletions or point mutations. 3) The presence of LOH is determined by comparing alleles at polymorphic markers in tumor vs. normal DNA from each patient. 4) Specific tests for DNA methylation is performed by comparing the Southern blot patterns of tumor DNAs digested with methylation-sensitive and -insensitive enzymes. For example, MspI- and HpaII-digested DNA is compared. The VHL gene, a tumor suppressor gene for renal cell carcinoma, is known to be somatically inactivated by methylation in some cases (Herman et al., Proc, Natl. Acad. Sci. USA, 91: 9700–9704 (1994)).

20. Improved tools for detecting N33 inactivation.

Detection of N33 expression or lack thereof would be considerably simplified by immunohistochemical assays for the N33 polypeptides in tissue sections. Antibodies reactive to one form of N33 protein was made as follows: a conserved 16-amino acid peptide at the N33 C-terminus (FIG. 20) was coupled to KLH and used to immunize rabbits. After six weeks, serum was harvested and antibodies were affinity-purified against a peptide column. These polyclonal antibodies were tested in a Western blot of recombinant N33 fusion proteins expressed in E. coli. (FIG. 21). As described above, clones A4 and A5 (partial N33 proteins fused to the glutathione-S-transferase gene carried in expression vector pGEX-2T) were obtained representing form 1 and form 2 mRNAs, respectively. Protein expression was induced by IPTG and cell lysates were separated by PAGE and transferred to membrane. The Western blot was incubated with affinity-purified polyclonal anti-N33 peptide antibody, and reactive bands were visualized by an alkaline-phosphatase conjugated secondary antibody and NBT/BCIP substrate. A fusion protein band of ~57 kD was detected in induced cells containing clone A4 but not A5 or other clones.

C. YAC TRANSFER TO MAMMALIAN CELLS

1. Retrofitting YAC Clones With Hycromycin Resistance

The plasmid vector pLUSH containing segments of the telomeric end of the YAC4 vector, a bacterial Kan$^R$ gene, the yeast Lys2 auxotrophy gene, and the mammalian hygromycin$^R$ gene (see map) was kindly provided by D. McElligott (Scripps Research Institute). pLUSH DNA was linearized by Sal I digestion and 5–10 μg was used to transform YAC-containing yeast cells using an alkali cation yeast transformation kit (Bio 101, Inc.) per manufacturer's instructions. Cells were plated on "triple drop-out" media (trp$^-$ ura$^-$ lys$^-$) to select for clones containing both the YAC and the conversion vector. Colonies were picked after 3–4 days and grown overnight in 2 ml of YPD medium. Yeast DNA was prepared and tested for homologous integration of pLUSH by PCR with primers )SEQ ID NOS: 4 and 5): 5'-CTTGAGATCGGGCGTTCGACTCGC-3' and 5'-TGAACGGTGATCCCCACCGGAATTG-3' (Hermanson et al., *Nucl. Acids Res.* 19:4943–4948 (1991). Reactions were carried out in 20 µl volumes with 100 ng of each primer in standard buffers plus 10% DMSO. Reaction conditions were 95° C., 2.5 min, then 35 cycles of 95° C., 40 sec; 60° C., 40 sec; and 72° C., 2 min), followed by 72° C. for 10 min. Homologous integration of the conversion vector results in amplification of a 1855 bp band (FIG. 6). The presence of the hygro$^R$ gene was confirmed by Southern blotting of yeast DNA with a radiolabelled hygro gene probe (FIG. 7).

2. Spheroplast Fusion and Selection of Transformants

A number of methods are available for transfer of YACs to mammalian cells. The spheroplast fusion protocol of Silverman et al., *Mol. Cell. Biol.* 13:5469–5478 (1993) was used. In brief, yeast cells grown by standard methods were pelleted, washed and resuspended in isotonic medium and cell walls digested with yeast lytic enzyme to produce yeast spheroplasts. These were layered on top of pelleted cultured mammalian cells such as NIH 3T3 cells or human tumor cells (50:1 numerical ratio) and incubated in the presence of polyethylene glycol 1500 (Boehringer-Mannheim) for 2 min at RT to induce fusion. Cells were diluted in tissue culture medium and incubated for 48 hr, after which selection with 300 µg/ml hygromycin was begun. Hygro-resistant colonies were apparent at approximately 3 weeks.

3. Genetic Analysis of Transformants

The presence of substantial portions of the YAC of interest was verified by PCR amplification or Southern blot detection of known genetic markers in the YAC (Table 8). For transfer of YACs to human cells, polymorphic markers were used such that allele sizes in the YAC differed from alleles already present in the parental cell. Retention of only part of transferred YACs can also be detected by these methods, and correlation of retained portions of YACs with phenotypic properties can be used to localize a tumor suppressor activity to a subregion of that covered by the YAC.

4. Phenotypic Analysis of Transformants

The phenotype of tumor cells after transfer of tumor suppressor genes can be assessed by a common set of assays regardless of whether transfer method, e.g., microcell transfer, retrovirus-mediated gene transfer, transfection, cell fusion, etc. Growth rate in vitro ($^3$H-thymidine incorporation), growth of transformants in soft agar, and tumorigenicity in nude mice can be compared in modified and parental cells to assess for tumor suppression activity, and thus, insertion of the vector and/or gene.

The preceding examples have been provided only to illustrate, not limit, this invention. It is understood that various modifications and additions can be made to this disclosure without departing from the spirit of this invention. Accordingly, this invention is defined by the following claims.

D. TESTING TUMOR SUPPRESSOR ACTIVITY OF PTSG.

The tumor suppressor activity of PTSG is assessed in both in vitro cell culture conditions and in nude mouse animal models. Any of the 13 N33-colon carcinoma cell lines listed in FIG. 17 (SW480, SW837, SW1417, HT-29, SW403, LS174T, DLD-1, CACO-2, EB, SK-CO-1, RKO, HCT116 and COLO-302) can be used to assess PTSG tumor suppressor activity.

Briefly, the effect of PTSG on the proliferation of the above cell lines is assessed following expression of PTSG using a adenoviral expression vector. ACN is a control adenoviral vector lacking a cDNA insert while AC-PTSG are adenoviral vectors expressing PTSG products under the control of the human CMV promoter.

In Vitro Transcription Translation of PTSG

Plasmid pBS-N33C(7) was tested for the ability to produce a 39 KD protein in the TNT Coupled Reticulocyte Lysate System (Promega, Madison, Wis.).

The T7 promoter in the Bluescript vector (Stratagene) allows for transcription and translation of the PTSG coding sequence by rabbit reticulocytes. One microgram of minilysate DNA is added per TnT Reticulocyte reaction and is incubated for 1 hour at 30 degrees Celsius. Ten microliters of the reaction is mixed with loading buffer and run on a 10 polyacrylamide gel (Novex) for 1½ hour at 165 V. The gel is dried down and exposed to film overnight.

Construction of adenoviral vectors containing PTSG

To construct recombinant adenoviruses, the insert of pBS-N33C(7) was recovered by EcoRI digestion and cloned into the EcoRi site of pcDNA3 (Invitrogen) to yield pcDNA3-N33 clones. The orientation of the insert was tested by Kpn I digestion, and clones in antisense orientation relative to the CMV promoter in pcDNA3 were subsequently used. For construction of the Form 1 adenovirus, pcDNA3-N33 was digested with Xba I-BamH I, and the insert was directionally cloned into the Xba I-BamH I sites of pAdCMVb vector to yield pACN33–1. For construction of the Form 2 adenovirus, pBS-N33C(7) was digested with ava III-EcoR I and the 5' half (nt 1–616) of N33 insert was purified. Clone AS was also digested with Ava III-EcoR I to release the 3' half of the N33 Form 2 insert (nt 617-EcoRI). The two gene halves were ligated and cloned into the EcoR I site of pcDNA3. Orientation of the reconstructed insert was agsin tested by Kpn I digestion and sequencing. An antisense orientation clone was then cut with Xba I and Bam HI and the insert cloned into pAdCMVb as above to yield pACN33–2.

The above plasmids are linearized with Nru I and are co-transfected with the large fragment of a Cla I digested dl309 mutants (Jones and Shenk, Cell, 17:683–689 (1979) which is incorporated herein by reference), using a CaPO$_4$ transfection kit (Stratagene). Viral plaques are isolated and recombinants are identified by both restriction digest analysis and PCR using primers against PTSG cDNA sequence. Recombinant virus is further purified by limiting dilution, and virus particles were purified and titered by standard methods (Graham and van der Erb, Virology, 52:456–457 (1973); Graham and Prevec, Manipulation of Adenovirus Vectors. In: *Methods in Molecular Biology Vol 7: Gene Transfer and Expression Protocols*, Murray E. J. (ed.) The Humana Press Inc., Clifton N.J., 7:109–128 (1991), both of which are incorporated herein by reference).

To ensure that the PTSG vector above expresses a protein of the appropriate size, colon carcinoma cell lines are infected with either the control or the PTSG-containing recombinant adenoviruses for a period of 24 hours at increasing multiplicities of infection (MOI) of plaque forming units of virus/cell. Cells are then washed once with PBS and harvested in lysis buffer (50 mM Tris-Hcl Ph 7.5, 250 Mm NaCl, 0.1% NP40, 50 mM NaF, 5 mM EDTA, 10 ug/ml aprotinin, 10 ug/ml leupeptin, and 1 mM PMSF). Cellular proteins are separated by 10% SDS-PAGE and transferred to nitrocellulose. Membranes are incubated with an anti-PTSG antibody followed by sheep anti-mouse IgG conjugated with horseradish peroxidase. Accurate expression of PTSG protein is visualized by chemiluminescence (ECL kit, Amersham) on Kodak XAR-5 film.

In Vitro.

N33-negative colon cancer cells (selected from the cell lines set out in FIG. 17) are seeded at 1×10⁶ cells per 100 mm plate in Kaighn's F12/DME medium (Irvine Scientific) which is supplemented with 10% FBS and 0.2 IU insulin (Sigma). The plates are incubated overnight at 37° C. in 7% $CO_2$. The following day, the cells are refed with 10 mls of growth medium and are infected with either ACN control viral lysate (MOI 10) or with AC-PTSG viral lysates (MOI 10) and allowed to incubate at 37° C. After 3 days, the medium is removed and the cells are fixed with a 1:5 acetic acid-methanol solution. The cells are stained with a 20% methanol-0.5% crystal violet solution for 30 minutes and are rinsed with tap water to remove excess stain.

Thymidine incorporation is also used to assess the effects of PTSG on cell proliferation. Briefly, approximately 3×10³ cells are plated in each well of a 96-well plate (Costar) and allowed to incubate overnight (37° C., 7% $CO_2$). Serial dilutions of ACN or AC-PTSG are made in DME:F12/15% FBS/1% glutamine, and cells are infected at multiplicity of infection (MOI) of 10 and 100 (4 replicate wells at each MOI) with each adenovirus. One-half of the cell medium volume is changed 24 hours after infection and every 48 hours until harvest. At 18 hours prior to harvest, 1 $\mu$Ci of ³H-thymidine (Amersham) is added to each well. Cells are harvested onto glass-fiber filters 5 days after infection, and ³H-thymidine incorporated into cellular nucleic acid is detected using liquid scintillation (TopCount®, Packard Instruments). Cell proliferation (cpm/well) at each MOI is expressed as a percentage of the average proliferation of untreated control cells.

Ex Vivo Gene Therapy.

To assess the effect of PTSG expression on tumorigenicity, the above tumor cell lines are tested for their ability to produce tumors in nude mouse models. Approximately 2×10⁷ cells are plated into T225 flasks, and cells are treated with sucrose buffer containing ACN or AC-PTSG adenoviruses at MOI of 3 or 30. Following overnight infections, cells are harvested and approximately 10⁷ cells are injected subcutaneously into the left and right flanks of BALB/c nude mice (4/group) that had previously received subcutaneous pellets of 17β-estradiol. One flank is injected with ACN-treated cells, while the contralateral flank is injected with AC-PTSG treated cells, each mouse serving as its own control. Animals receiving bilateral injections of untreated cells serve as an additional control for tumor growth. Tumor dimensions (length, width, height) and body weights are then measured twice per week. Tumor volumes are estimated for each animal assuming a spherical geometry with radius equal to one-half the average of the measured tumor dimensions.

In Vivo Tumor Suppression with PTSG.

Colon cancer cell lines are injected subcutaneously into female BALB/c athymic nude mice. Tumors are allowed to develop for 32 days. At this point, a single injection of either ACN (control) or AC-PTSG adenoviruses are injected into the peritumoral space surrounding the tumor. Tumors are then excised at either Day 2 or Day 7 following the adenovirus injection, and poly-A+ RNA is isolated from each tumor. Reverse transcriptase-PCR using PTSG specific primers, are then used to detect PTSG RNA in the treated tumors. Amplification with actin primers will serve as a control for the RT-PCR reaction while a plasmid containing the recombinant-(PTSG) sequence will serve as a positive control of the recombinant-(PTSG) specific band.

In a separate experiment, cells are injected into the subcutaneous space on the right flank of mice, and tumors are allowed to grow for 2 weeks. Mice receive peritumoral injections of buffer or recombinant virus twice weekly for a total of 8 doses. Tumor growth is monitored throughout treatment in the control animals receiving ACN and buffer and those animals receiving AC-PTSGs. Body weight and survival time is also monitored.

sAlthough the invention has been described with reference to the presently-preferred embodiment, it should be understood that various modifications can be made without departing from the spirit of the invention. Accordingly, the invention is limited only by the following claims.

TABLE 1

CHROMOSOME 8p DELETION MAP IN HUMAN PROSTATE CANCER
Allelic Loss on Chromosome 8 in Prostate Cancer

| Locus | Poly-morphism type | Probe | Enzyme | Location | No. of Cases ? | Allelic losses/ informative cases (all tumors) | Allelic losses/ informative cases (node metastases) |
|---|---|---|---|---|---|---|---|
| D8S140 | RFLP[a] | C18-1 | MspI | 8p23.2–23.3 | 49 | 4/38 (11)[b] | 1/6 (17) |
| D8S201 | Micro-satellite | Mfc199 | — | 8p23 | 30 | 3/22 (14) | 1/2 (50) |
| D8S163 | RFLP | KSR2 | TaqI | 8p22-pier | 50 | 14/23 (61) | 2/4 (50) |
| MSR | RFLP | M8R32 | MspI | 8p22 | 50 | 20/29 (69) | 3/3 (100) |
| LPL | Micro-satellite | GZ14.15 | — | 8p22 | 45 | 15/32 (47) | 0/2 (0) |
| D8S220 | RFLP | C18-319 | TaqI | 8p21.2–21.3 | 51 | 16/27 (59) | 4/5 (80) |
| NEFL | RFLP | NF5.1 | TaqI | 8p21 | 12 | 2/6 (33) | Not studied |
| D8S194 | RFLP | C18-277 | MspI | 8p11.21–11.22 | 51 | 3/20 (12) | 1/4 (25) |
| D8S39 | RFLP | MCT128.2 | TaqI | 8q24 | 43 | 2/17 (12) | 0/3 (0) |

[a]RFLP, restriction fragment length polymorphism.
[b]Numbers in parentheses, percentage.

TABLE 2

| No. | Locus Name | Chromosomal interval | Type | Primer sequences (5'—3') | Product size (bp) | Anneal temp. (° C.) | Reference |
|---|---|---|---|---|---|---|---|
| 1 | D8S26 | A | RFLP | TAGCTCCTTCGAAACCCTCA TGGCAGGAAAAGCTCTCAAT | 124 | 60 | This report* |
| 2 | D8S511 | A | STRP | TTGTCCCTGTTGGCAGA TGATTTTTGTGTCCTGAAACTTA | ~135 | 55 | This report |
| 3* | D8S549 | A | STRP | AAATGAATCTCTGATTAGCCAAC TGAGAGCCAACCTATTTCTACC | ~170 | 55 | This report |
| 4 | MSR | A | RFLP | TTCATCTATTGCATTCC CAAAATTTCAGCATGACAACTG | 102 | 50 | Matsumoto et al. 1990 |
| 5 | D8S254 | B | STRP | TGCCGGACATACATTAGTGA TTGTAAACACCACAAGCAGG | ~70 | 55 | J. Weber, pers. commun. |
| 6 | D8S233 | B | RFLP | TTTGAGTAGCCAGAGTCCAG CGTACCATTTCCATCTGCT | 84 | 55 | This report* |
| 7 | D8S261 | B | STRP | TGCCACTGTCTTGAAAATCC TATGGCCCAGCAATGTGTAT | ~135 | 55 | Weissenbach et al., 1992 |
| 8 | D8S21 | B | RFLP | CACTGAGGAAGAGGTTGAAG ATCCATCACCAGGTTTGG | 86 | 55 | This report* |
| 9 | LPL | B | STRP | ATCTGACCAAGGATAGTGGGAT CCTGGGTAACTGAGCGAGACT | ~130 | 60 | Zuliaru and Hobbs. 1990 |
| 10* | D8S258 | B | STRP | CTGCCAGGAATCAACTGAG TTGACAGGGACCCACG | ~150 | 55 | Weissenbach et al. 1992 |

Polymorphic loci on chromosome arm 8p comprising mapping framework. Chromosomal intervals (A or B) are defined as in Wagner et al. (1991). All loci were used to screen YAC pools
*: Screening performed at Genethon.
+: STS creatd within RFLP probe as described herein.

TABLE 3

| No. | Locus/probe Name | Chromosomal Interval | Type | Primer Sequences (5'—3') | Product Size | Anneal temp (° C.) |
|---|---|---|---|---|---|---|
| 1 | D8S206 | A | STRP | GAAAACCATGGCTGGGTG ACATGCATTAGCACTACCATGC | ~130 | 55 |
| 2 | D8S294E | B | EST | TGACCTGAAATTACAAGGTA AGCAGCTTGACAATCTTAAG | 82 | 55 |
| 3 | D8S297E | B | EST | CGTAGCTGCAGTTGTCCACG CATTCTGACTACTACTTTCAG | 67 | 55 |
| 4 | E1* | A | random subclone | TGACACACTTGCCATTTGAT TTCCATTAGTCCCAGTTGTC | 131 | 55 |
| 5 | E3 | A | random subclone | GCCTGTTTCATCGAACC CCTGGCATTCTTTACCTAGA | 85 | 55 |
| 6 | E15 | A | random subclone | GTTCTTGCCATGTGATGTG GTGGCATCTGCTTCTGG | 86 | 55 |
| 7 | E17 | A | random subclone | CAAGGCATATCACAACTGC GATAATTGAACTGTCACCTCTG | 121 | 55 |
| 8 | E20 | B | random subclone | TGAATTTGCATAGTCTGCAG CAGCTCTAACAAGGCTCCTA | 107 | 55 |
| 9 | E31 | A | random subclone | TCAGGGCCTCTTGCAT TGGGAACTTCAAGCATAGG | 97 | 55 |
| 10 | E56 | B | random subclone | TTTGTTGAGGACAAATACCC TGTCACGATGAGGATTGTTA | 170 | 55 |
| 11 | YE766 | A | YAC end | GACTCTTGCCACCTTGTAAA ATCTCCAAACCTACTTCTCC | 89 | 55 |

TABLE 3-continued

| No. | Locus/probe Name | Chromosomal Interval | Type | Primer Sequences (5'-3') | Product Size | Anneal temp (° C.) |
|---|---|---|---|---|---|---|
| 12 | YE843 | B | YAC end | AGCAAAGTGATGGTGGTAAC GGACTAATTACCTCAGGCCT | 82 | 55 |
| 13 | YE932 | B | YAC end | ATGGAAATGCACGGGA CCATTCTGTCCCAATGATC | 173 | 55 |

Sequence-tagged sites used for physical map refinement. Chromosomal intervals (A or B) are defined as in Wagner et al. (1991). D8S206 (Hudson et al., 1992), D8S294E and D8S297E (Adams et al., 1992) were reported previously; remaining STSs were created by partial sequencing of subcloned probes as described herein.
*Detects Hind III RFLP.
EST: expressed sequence tag.

TABLE 4

| YAC address | STS pS26 | STS S206 | STS pG13 | pG2 | STS S511 | pA37 | pG18 | STS pE31 | pA33 | STS S549 | STS pE17 | STS pE15 | STS YE766 | STS pE1 | STS pE3 | STS MSR | STS pE20 |
|---|---|---|---|---|---|---|---|---|---|---|---|---|---|---|---|---|---|
| 920—c—11 | P | P | NN | NN | N |  |  | N | NN | N | N |  | N |  |  | NN |  |
| 887—a—3 | P | P | PP | NN | N |  |  | N | NN | N | N |  | N |  |  | NN |  |
| 893—a—9 | P | P | PP | NN | N |  |  | NN | NN | N | N |  | N |  |  | NN |  |
| 944—f—2 | P | P | PP | PP | P | NN | NN | NN | NN | N | N | NN | N | N | N | NN |  |
| 885—c—8 | N | N | PP | PP | P | NN | NN | NN | NN | N | N | NN |  |  |  |  |  |
| 917—h—10 | N | N | NN | NN | P | PP | PP | NN | NN | N | N | NN |  |  |  |  |  |
| 937—a—10 | N | N | NN | NN | P | PP | PP | NN | NN | N | N | NN |  |  |  |  |  |
| 958—d—9 | N | N | NN | NN | P | PP | PP | NN | NN | N | N | NN |  |  |  |  |  |
| 821—f—7 | N | N | NN | PP | P | PP | PP | PP | PP | PP | N | NN |  |  |  |  |  |
| 832—a—10 | N | N | NN | PP | P | PP | PP | PP | PP | P | NN | NN | N | NN | NN | NN | NN |
| 840—g—7 | N | N | NN | PP | P | PP | PP | PP | PP | P | NN | NN | N | NN | NN | NN | NN |
| 539—g—4 |  | N | NN | NN | N | NN | NN | P | PP | P | N | NN | N |  | N | N | N |
| 946—c—9 | N | N | NN |  | N | NN | NN | PP | PP | PP | PP | P | P | P | PP | N |  |
| 856—e—11 | N |  | NN |  | N | NN | NN | NN | PP | PP | PP | P | P | P | PP | N |  |
| 802—f—11 | N |  | NN | NN | N | NN | NN | NN | PP | PP | PP | P | P | PP | PP | P |  |
| 767—h—8 |  | N | NN |  | N | NN | NN | NN | P | PP | NN | N | N | NN | NN | NN |  |
| 932—e—9 | N |  | NN |  | N | NN | NN | PP | PP | PP | PP | PP | PP | PP | PP | PP |  |
| 931—a—1 | N |  | NN |  | N | NN | NN | PP | PP | P | PP | PP | PP | P | PP | PP |  |
| 766—a—12 | N | N |  |  | N | NN |  | NN | NN | P | NN | NN | P | PP | PP | PP |  |
| 874—a—6 | N | N | NN |  | N | NN | NN | NN | NN | N | NN | NN | N | P | PP | PP |  |
| 870_a_7 | N | N | NN |  | N |  |  | NN | NN | N | NN | NN | NN | NN | NN | NN |  |
| 857_h_5 | N | N |  |  | N |  |  | NN | NN | N | NN | NN | NN | NN | NN | NN |  |
| 903_h_1 | N | N |  |  | N |  |  | NN | NN | N | NN | NN | NN | NN | NN | NN |  |
| 813_e_4 | N | N |  |  |  | NN | NN | NN | NN | N | NN | NN | NN | NN | NN | NN |  |
| 893_g_12 | N | N |  |  |  | NN | NN | NN | NN | N | NN | NN | NN | NN | NN | NN |  |
| 852_f_10 | N |  |  |  |  | NN |  | NN | NN | N | N | NN | NN | NN | NN | NN |  |
| 812_g_7 | N | N |  |  |  | NN |  | NN | NN | N | N |  | N |  | N | N | NN |
| 843_g_3 | N | N |  |  |  | NN |  | NN | NN | N | NN | NN | NN | NN | NN | NN |  |
| 753_e_4 |  |  |  |  |  |  |  |  |  |  |  |  |  |  |  |  |  |

TABLE 4-continued

| YAC address | STS pE56 | pE23 | pE32 | pE58 | STS S254 | STS YE932 | STS YE843 | STS pS233 | STS S294E | STS S261 | STS pS21 | STS S297E | STS LPL | STS S258 | | |
|---|---|---|---|---|---|---|---|---|---|---|---|---|---|---|---|---|
| 847_f_8 | | | | | | | | | | | | | | | | |
| 847_a_9 | N | N | | | | | NN | N | NN | | N | | N | NN | | |
| 915_d_8 | | N | | | | | NN | N | NN | | N | | N | NN | | |
| 859_a_7 | N | N | | | | NN | NN | N | N | | N | | N | NN | | |
| 936_c_3 | | | | | | | | | | | | | | | | |
| 943_d_12 | N | | | | | | NN | N | N | | N | | | NN | | |
| 948_d_5 | | | | | | | | N | | | | | | | | |
| INTERVAL | A | A | | | A | | | | A | A | | A | A | A | A | B |

| YAC address | STS pE56 | pE23 | pE32 | pE58 | STS S254 | STS YE932 | STS YE843 | STS pS233 | STS S294E | STS S261 | STS pS21 | STS S297E | STS LPL | STS S258 | YAC size (Kb) | Chi-meric |
|---|---|---|---|---|---|---|---|---|---|---|---|---|---|---|---|---|
| 920_c_11 | | NN | | NN | N | | N | NN | N | N | NN | N | | | 1550 | yes |
| 887_a_3 | | NN | NN | NN | N | N | N | NN | N | N | NN | N | N | | 1050 | |
| 893_a_9 | | NN | | NN | N | | N | NN | N | N | NN | N | | | 1150 | |
| 944_f_2 | NN | NN | NN | NN | N | N | N | NN | N | N | NN | N | | | 1700 | |
| 885_c_8 | | NN | NN | NN | | | | | | | | | | | 1200 | |
| 917_h_10 | | NN | NN | NN | | | | | | | | | | | 1410* | |
| 937_a_10 | | NN | NN | NN | | | | | | | | | | | 1740* | |
| 958_d_9 | | NN | NN | NN | | | | | | | | | | | 1060* | |
| 821_f_7 | | NN | NN | NN | | | | | | | | | | | 1400 | |
| 832_a_10 | NN | NN | NN | NN | N | N | N | | N | | N | | | | 1400 | no |
| 840_g_7 | NN | NN | NN | NN | N | N | N | | N | | N | | | | >1600 | yes |
| 539_g_4 | N | NN | NN | NN | N | | | | | | | | | | 620* | no |
| 946_c_9 | N | NN | NN | NN | N | | | | | | | | | | 1200 | |
| 856_e_11 | N | NN | NN | NN | N | | | | | | | | | | 700* | |
| 802_f_11 | P | PP | NN | NN | N | | | | | | | | | | 850 | |
| 767_h_8 | PP | PP | PP | NN | N | N | N | | N | | N | | | | 650 | no |
| 932_e_9 | PP | PP | PP | PP | P | P | N | NN | N | N | NN | N | N | | 1400 | no |
| 931_a_1 | PP | PP | PP | PP | P | P | P | NN | N | N | N | N | N | | >1600 | yes |
| 766_a_12 | PP | PP | PP | PP | P | P | P | NN | N | N | N | N | N | | 1050 | no |
| 874_a_6 | PP | PP | NN | NN | N | N | N | NN | N | N | NN | N | N | | 600 | yes |
| 870_a_7 | NN | PP | PP | PP | P | N | N | NN | N | N | NN | N | N | | 825 | |
| 857_h_5 | NN | PP | PP | PP | P | P | N | NN | N | N | NN | N | N | | 600 | |
| 903_h_1 | NN | NN | PP | PP | P | P | N | NN | N | N | NN | N | N | | 1025 | no |
| 813_e_4 | NN | NN | NN | PP | P | P | P | PP | P | N | N | N | N | N | 1100 | no |
| 893_g_12 | NN | NN | NN | PP | P | P | PP | P | N | N | N | N | N | | 1025 | |
| 852_f_10 | | NN | | NN | P | P | P | P | P | NN | N | N | N | | 1300 | |
| 812_g_7 | | NN | | NN | N | P | PP | P | NN | N | N | N | | | 1150 | |
| 843_g_3 | NN | NN | NN | NN | N | N | P | P | P | NN | N | N | N | | 1150 | |
| 753_e_4 | | | | | N | N | N | N | N | P | P | P | N | N | 1750* | yes |

TABLE 4-continued

| | | | | | | | | | | | | | | | | |
|---|---|---|---|---|---|---|---|---|---|---|---|---|---|---|---|---|
| 847—f—8 | | | | | N | N | N | N | N | N | P | P | P | N | N | 1390* | |
| 847—a—9 | NN | NN | | NN | N | N | N | NN | N | N | P | P | N | N | 1500 | yes |
| 915—d—8 | NN | NN | | NN | N | N | N | NN | N | N | P | P | N | N | 1600 | |
| 859—a—7 | | NN | NN | NN | N | N | N | NN | N | N | P | P | P | N | 1900 | no |
| 936—c—3 | | | | | N | | | | N | N | P | P | | | 1600* | yes |
| 943—d—12 | | NN | | NN | N | N | N | NN | N | N | N | N | P | P | 1390* | no |
| 948—d—5 | | | | | N | | | | N | N | P | P | | | 1740* | no |
| INTERVAL | B | | | | B | B | B | B | B | B | | B | B | B | | |

TABLE 5

Pairwise analysis of six markers in the radiation hybrid panel. Statistics were calculated by the TWOPOINT program. $cR_{5000}$: centiray at 5000 Rad irradiation.

| Marker A | Marker B | Number of clones observed | | | | total | Theta | $cR_{5000}$ | LOD |
|---|---|---|---|---|---|---|---|---|---|
| | | ++ | +− | −+ | −− | | | | |
| D8S26 | MSR | 11 | 5 | 3 | 73 | 92 | 0.3115 | 37 | 7.17 |
| D8S26 | D8S233 | 9 | 6 | 2 | 74 | 91 | 0.3394 | 41 | 5.99 |
| D8S26 | D8S261 | 9 | 7 | 1 | 75 | 92 | 0.3463 | 43 | 6.08 |
| D8S26 | D8S21 | 10 | 6 | 1 | 75 | 92 | 0.2948 | 35 | 7.21 |
| D8S26 | LPL | 10 | 6 | 3 | 73 | 92 | 0.3595 | 45 | 6.08 |
| MSR | D8S233 | 11 | 3 | 1 | 77 | 92 | 0.1741 | 19 | 9.87 |
| MSR | D8S261 | 9 | 6 | 2 | 76 | 93 | 0.3563 | 44 | 6.06 |
| MSR | D8S21 | 10 | 5 | 2 | 76 | 93 | 0.3026 | 36 | 7.20 |
| MSR | LPL | 10 | 5 | 4 | 74 | 93 | 0.3675 | 46 | 6.10 |
| D8S233 | D8S261 | 9 | 3 | 1 | 79 | 92 | 0.1995 | 22 | 8.31 |
| D8S233 | D8S21 | 10 | 2 | 1 | 79 | 92 | 0.1444 | 16 | 9.89 |
| D8S233 | LPL | 9 | 3 | 4 | 76 | 92 | 0.3147 | 38 | 6.45 |
| D8S261 | D8S21 | 11 | 0 | 1 | 81 | 93 | 0.0496 | 5 | 12.91 |
| D8S261 | LPL | 10 | 1 | 4 | 78 | 93 | 0.2305 | 26 | 8.46 |
| D8S21 | LPL | 11 | 1 | 3 | 78 | 93 | 0.1786 | 20 | 9.89 |

TABLE 6

Genomic subclones

| series | Name | Probe fragments, kb (enzyme) | Human chrom, 8 | HindIII fragments detected, kb |
|---|---|---|---|---|
| | | 932E9 | | |
| E | 1c | 1.6 (EcoRI) | Yes | 8 |
| E | 1e | 1.0 (EcoRI) | Yes | [4 + 8], 12** |
| E | 2d | 0.85, 1.0 (EcoRI) | Yes | 7.5 |
| E | 2 | 0.8 (EcoRI) | Yes | 5.5 + 3.8 |
| E | 3 | 0.5, 4, 5 (EcoRI + NotI) | Yes | ~12 |
| E | 6* | 1.2 (EcoRI + NotI) | Yes | 3.8 |
| E | 10* | 0.25, 3.0 (EcoRI + NotI) | Yes | 7 |
| E | 15 | 0.9 (HindIII + SacII) | Yes | 1.2 |
| E | 17* | 0.3, 1.2 (EcoRI + NotI) | Yes | 5 |
| E | 18 | 1.0, 1.8, 4.5 (HindIII) | Yes | 1.0 |
| E | 20* | 1.5, 1.9 (EcoRI + Not) | Yes | 7 |
| E | 23* | 1.6 (EcoRI + NotI) | Yes | 8 |
| E | 31* | 1.9, 2.5, 3 (EcoRI + NotI) | Yes | 3.5 |
| E | 32 | 0.2, 0.5, 1.0, 2.1 (EcoRI) | Yes | ~8 |
| E | 56 | 0.2, 0.4, 1 (EcoRI + StyI) | Yes | 5.6 |
| E | 58 | 0.8, 1.2, 1.8 (Eco + SacII) | Yes | 8.5 |
| | | 767H8 | | |
| H | 23 | 1, 1.3, 2.1 (EcoRI + SacII) | Yes | 6 |
| H | 25 | 0.5, 1.7 (PstI + SacII) | Yes | 1.6 |
| H | 29 | 1.0, 1.5 (EcoRI + SacII) | Yes | 4.2, 2.4, 1.3?? |
| H | 31 | 0.45 (EcoRI + SacII) | Yes | 7 |
| | | 802F11 | | |
| F | 4 | 0.5, 1.6 (EcoRI + SacII) | Yes | 1.6 |
| | | 832A10 | | |
| A | 33 | 0.35 (EcoRI + SacI) | Yes | 1 |
| A | 37 | 1.1, 3.2 (EcoRI + SacII) | Yes | 12 |
| | | 821F7 & 885C8 | | |
| G | 2 | 0.5, 6 (HindIII + SacII) | Yes | ~1.2 |
| G | 4 | 0.4 (SmaI) | Yes | 3.2 + high background |
| G | 10 | 0.25, 6 (EcoRI + SacII) | Yes | ~12 |
| G | 14 | 0.4, 1.6 (EcoRI + SacII) | Yes | ~2 |
| G | 18* | 1.2 (EcoRI + SacII) | Yes | ~10 |
| | | YAC end clones | | |
| YE1-766A12 | | 0.25 (EcoRI) | Yes | 5 |
| YE1-843G3 | | | Yes | |
| YE1-932E9 | | 0.6 (EcoRI) | Yes | 1.8 |
| | | PAC E1c subclones | | |
| PAC A2 | | | Yes | |
| PAC A3 | | | Yes | |
| PAC B3 | | | Yes | |

*Contains no Alu; **polymorphism; fragment without Alu used as probe.

TABLE 7 selected cDNAs

| Series | No. | Probe fragments, bp (enzyme) | Human chrom. 8 | HindIII frag's detected, kb | ID or Hom. |
|---|---|---|---|---|---|
| | | | selected by 802F11 | | |
| J | 2 | ~325 (BstXI) | Yes | 2.5 | |
| J | 10 | ~350 (BstXI) | Yes | 4 | |
| J | 12 | ~350 (BstXI) | Yes** | ~10* + 6** | hom. to PP2Cα |
| J | 28 | ~400 (BstXI) | Yes | 4 (+3, weak) | novel ORF |
| P | 3 | ~350 (BstXI) | Yes | ~12 | MSR (1-280 bp) |
| P | 10 | ~400 (BstXI) | Yes | 2 | |
| P | 14 | ~450 (BstXI) | Yes | 3.5 | |
| P | 16 | 1 band (BstXI) | Yes | 2.2 | |
| P | 25 | ~300 (BstXI) | Yes | 4 | |
| P | 27 | ~450 + 350 (BstXI) | Yes | 4 | seq. overlap with J28 |
| P | 28 | ~400 (BstXI) | Yes | 12 (+5.2) | MSR (1-450 bp) |
| P | 34 | ~250 (BstXI) | Yes | 3.8 | MSR (3' UTR) & HSDHEHC01 |
| W | 17 | ~400 (R1 + HIII) | Yes | 3.5 + background | |
| | | | selected by 821F7 or 877F2 | | |
| K | 26 | ~350 (RI + HIII) | Yes | >12 | |
| K | 27 | ~500 (RI + HIII) | Yes | >12 | |
| K | 36 | ~250 (RI + HIII) | Yes | 2.7 | |
| | | | selected by 946C9 | | |
| L | 3 | ~400 (RI + HIII) | Yes | 4 | overlaps J28 |
| L | 5 | ~325 (RI + HIII) | Yes | 0.5 | |
| L | 12 | ~300 (RI + HIII) | Yes | 3.8 | |
| L | 14 | ~550 (RI + HIII) | Yes | 6 + some background | |
| L | 21 | ~450 (RI + HIII) | Yes | 5.4 + 4 + 3 | |
| L | 30 | (RI + HIII) | Yes | 4.5 + some background | |
| L | 31 | (RI + HIII) | Yes | 7 | |
| N | 1 | (RI + HIII) | Yes | 4.8 + high background | |
| N | 7 | (RI + HIII) | Yes | 3 + background | |
| N | 14 | ~600 (RI + HIII) | Yes | 2.6 | |
| N | 18 | ~250 (RI + HIII) | Yes | >12 | |
| N | 19 | ~600 (RI + HIII) | Yes | 1.6 | |
| N | 21 | ~800 (RI + HIII) | Yes | | overlaps L21 |
| N | 27 | ~500 (RI + HIII) | Yes | 3 + background | |
| N | 28 | ~550 (RI + HIII) | Yes | 4 | overlaps J28 |
| N | 33 | (RI + HIII) | Yes | 12, 11, 4, 3.2, 2 | overlaps L21 |
| N | 35 | (RI + HIII) | Yes | ~12 | |
| N | 36 | (RI + HIII) | Yes | 12, 11, 4, 3, 2 | overlaps N33 |
| X | 3 | ~500 (RI + HIII) | Yes | ~12 | |
| X | 6 | ~500 (RI + HIII) | Yes | 1.8 | |
| | | | selected by 932E9 | | |
| Q | 30 | ~500 (RI + HIII) | Yes | 3.5 | |
| | | | selected by 946C9 and 932E9 | | |
| Y | 1A1 | U & L bands | Yes | | |
| Y | 1A8 | | Yes | | |
| Y | 1C8 | | Yes | | |

*polymorphic; **6 kb band is not on chromosome 8.

We claim:

1. An isolated and purified DNA molecule having the nucleotide sequence of SEQ ID NO: 55.

2. A DNA probe having a sequence complementary to a sequence of at least about 15 contiguous nucleotides of the DNA sequence of claim 1.

3. An RNA probe having a sequence complementary to a sequence of at least about 15 contiguous nucleotides of the DNA sequence of claim 1.

4. An isolated and purified DNA molecule having the nucleotide sequence of SEQ ID NO: 57.

5. A DNA probe having a sequence complementary to a sequence of at least about 15 contiguous nucleotides of the DNA sequence of claim 4.

6. An RNA probe having a sequence complementary to a sequence of at least about 15 contiguous nucleotides of the DNA sequence of claim 4.

7. A recombinant vector containing the isolated, purified DNA of claims 1 or 4.

8. An expression vector comprising said DNA molecule of claims 1 or 4, which expresses the protein encoded by the DNA molecule of claims 1 or 4 in a mammalian host cell.

9. The recombinant vector of claim 7, wherein the vector is a cosmid, plasmid, or is derived from a virus.

10. The expression vector of claim 8, wherein said expression vector is selected from the group consisting of a plasmid and a viral vector.

11. A host-vector system for the production of a polypeptide or protein encoded by a nucleic acid having a nucleotide sequence of SEQ ID NO. 55 or 57 which comprises the vector of claim 8 in a suitable host cell.

12. A composition comprising the vector of claim 8 and a pharmaceutically-acceptable carrier.

13. The expression vector of claim 10, wherein the vector is a viral vector and is selected from the group consisting of a retroviral vector and an adenoviral vector.

14. A composition comprising the vector of claim 10 and a pharmaceutically-acceptable carrier.

15. A host-vector system for the production of a polypeptide or protein encoded by a nucleic acid having a nucleotide sequence of SEQ ID NO. 55 or 57 which comprises the vector of claim 10 in a suitable host cell.

16. The host-vector system of claim 11, wherein the host cell is a prokaryotic cell.

17. The host-vector system of claim 11, wherein the host cell is a eukaryotic cell.

18. The expression vector of claim 13, wherein said expression vector is an adenoviral vector.

19. A host-vector system for the production of a polypeptide or protein encoded by a nucleic acid having a nucleotide sequence of SEQ ID No. 55 or 57 which comprises the vector of claim 13 in a suitable host cell.

20. The host-vector system of claim 15, wherein the host cell is a prokaryotic cell.

21. The host-vector system of claim 15, wherein the host cell is a eukaryotic cell.

22. A host-vector system for the production of a polypeptide or protein encoded by a nucleic acid having a nucleotide sequence of SEQ ID NO. 55 or 57 which comprises the vector of claim 18 in a suitable host cell.

23. The host-vector system of claim 19, wherein the host cell is a prokaryotic cell.

24. The host-vector system of claim 19, wherein the host cell is a eukaryotic cell.

25. The host-vector system of claim 22, wherein the host cell is a prokaryotic cell.

26. The host-vector system of claim 22, wherein the host cell is a eukaryotic cell.

27. A composition comprising an ACPTSG vector and a pharmaceutically acceptable carrier.

\* \* \* \* \*

UNITED STATES PATENT AND TRADEMARK OFFICE
CERTIFICATE OF CORRECTION

PATENT NO.     : 6,043,088

DATED          : March 28, 2000

INVENTOR(S)    : Robert Bookstein *et al.*

It is certified that error appears in the above-identified patent and that said Letters Patent is hereby corrected as shown below:

Please add to the inventorship the names of inventors Donal MacGrogan and G. Steven Bova as follows:

[75] Inventors: Robert Bookstein, La Jolla, Calif.;
William B. Isaacs, Glyndon, Md.;
Donal MacGrogan, New York, NY.;
G. Steven Bova, Baltimore, MD.

Signed and Sealed this

Twenty-second Day of May, 2001

*Attest:*

NICHOLAS P. GODICI

*Attesting Officer*     *Acting Director of the United States Patent and Trademark Office*

SEQUENCE LISTING (1) GENERAL INFORMATION:

(iii) NUMBER OF SEQUENCES: 59

(2) INFORMATION FOR SEQ ID NO:1:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:1:

GAATCCTTCC CCCAC                                                    15

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:2:

CGATCTAGAC CAGCACAATG G                                             21

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:3:

CCATTGTGCT GGTCTAGATC GCACA                                         25

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:4:

CTTGAGATCG GGCGTTCGAC TCGC                                          24

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:5:

TGAACGGTGA TCCCCACCGG AATTG                                         25

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:6:

TAGCTCCTTC GAAACCCTCA                                               20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:7:

TGGCAGGAAA AGCTCTCAAT                                                          20

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:8:

TTGTCCCTGT TGGCAGA                                                             17

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:9:

TGATTTTTGT GTCCTGAAAC TTA                                                      23

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:10:

AAATGAATCT CTGATTAGCC AAC                                                      23

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:11:

TGAGAGCCAA CCTATTTCTA CC                                                       22

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:12:

TTCATCTATT GCATTCC                                                             17

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:13:

CAAAATTTCA GCATGACAAC TG                                                       22

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:14:

TGCCGGACAT ACATTAGTGA                                    20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

TTGTAAACAC CACAAGCAGG                                    20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:16:

TTTGAGTAGC CAGAGTCCAG                                    20

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:17:

CGTACCATTT CCATCTGCT                                     19

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:18:

TGCCACTGTC TTGAAAATCC                                    20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:19:

TATGGCCCAG CAATGTGTAT                                    20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:20:

CACTGAGGAA GAGGTTGAAG                                                           20

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:21:

ATCCATCACC AGGTTTGG                                                             18

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:22:

ATCTGACCAA GGATAGTGGG AT                                                   22

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:23:

CCTGGGTAAC TGAGCGAGAC T                                                    21

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:24:

CTGCCAGGAA TCAACTGAG                                                       19

(2) INFORMATION FOR SEQ ID NO:25:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:25:

TTGACAGGGA CCCACG                                                               16

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:26:

```
GAAAACCATG GCTGGGTG                                        18
```

(2) INFORMATION FOR SEQ ID NO:27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:27:

```
ACATGCATTA GCACTACCAT GC                                   22
```

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:28:

```
TGACCTGAAA TTACAAGGTA                                      20
```

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:29:

```
AGCAGCTTGA CAATCTTAAG                                      20
```

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:30:

```
CGTAGCTGCA GTTGTCCACG                                      20
```

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:31:

```
CATTCTGACT ACTACTTTCA G                                    21
```

(2) INFORMATION FOR SEQ ID NO:32:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:32:

TGACACACTT GCCATTTGAT                                               20

(2) INFORMATION FOR SEQ ID NO:33:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:33:

TTCCATTAGT CCCAGTTGTC                                               20

(2) INFORMATION FOR SEQ ID NO:34:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:34:

GCCTGTTTCA TCGAACC                                                  17

(2) INFORMATION FOR SEQ ID NO:35:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:35:

CCTGGCATTC TTTACCTAGA                                               20

(2) INFORMATION FOR SEQ ID NO:36:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:36:

GTTCTTGCCA TGTGATGTG                                                19

(2) INFORMATION FOR SEQ ID NO:37:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:37:

GTGGCATCTG CTTCTGG                                                  17

(2) INFORMATION FOR SEQ ID NO:38:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:38:

CAAGGCATAT CACAACTGC                                                       19

(2) INFORMATION FOR SEQ ID NO:39:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:39:

GATAATTGAA CTGTCACCTC TG                                                   22

(2) INFORMATION FOR SEQ ID NO:40:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:40:

TGAATTTGCA TAGTCTGCAG                                                      20

(2) INFORMATION FOR SEQ ID NO:41:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:41:

CAGCTCTAAC AAGGCTCCTA                                                      20

(2) INFORMATION FOR SEQ ID NO:42:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:42:

TCAGGGCCTC TTGCAT                                                          16

(2) INFORMATION FOR SEQ ID NO:43:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:43:

TGGGAACTTC AAGCATAGG                                                       19

(2) INFORMATION FOR SEQ ID NO:44:

(i) SEQUENCE CHARACTERISTICS:

(A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:44:

TTTGTTGAGG ACAAATACCC                                              20

(2) INFORMATION FOR SEQ ID NO:45:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:45:

TGTCACGATG AGGATTGTTA                                              20

(2) INFORMATION FOR SEQ ID NO:46:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:46:

GACTCTTGCC ACCTTGTAAA                                              20

(2) INFORMATION FOR SEQ ID NO:47:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:47:

ATCTCCAAAC CTACTTCTCC                                              20

(2) INFORMATION FOR SEQ ID NO:48:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:48:

AGCAAAGTGA TGGTGGTAAC                                              20

(2) INFORMATION FOR SEQ ID NO:49:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:49:

GGACTAATTA CCTCAGGCCT                                              20

(2) INFORMATION FOR SEQ ID NO:50:

(i) SEQUENCE CHARACTERISTICS:
            (A) LENGTH: 16 base pairs (B) TYPE: nucleic acid
(C) STRANDEDNESS: single
(D) TOPOLOGY: linear (xi) SEQUENCE DESCRIPTION: SEQ ID NO:50:

ATGGAAATGC ACGGGA 16

(2) INFORMATION FOR SEQ ID NO:51:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:51:

CCATTCTGTC CCAATGATC 19

(2) INFORMATION FOR SEQ ID NO:52:

(i) SEQUENCE CHARACTERISTICS:
(A) LENGTH: 1342 base pairs
(B) TYPE: nucleic acid
(C) STRANDEDNESS: single
(D) TOPOLOGY: linear (xi) SEQUENCE DESCRIPTION: SEQ ID NO:52:

GAATTCGGGC GGCCGCGGCC CGGGTCCCTC GCAAAGCCGC TGCCATCCCG GAGGGCCCAG 60

CCAGCGGGCT CCCGGAGGCT GGCCGGGCAG GCGTGGTGCG CGGTAGGAGC TGGGCGCGCA 120

CGGCTACCGC GCGTGGAGGA GACACTGCCC TGCCGCGATG GGGGCCCGGG GCGCTCCTTC 180

ACGCCGTAGG CAAGCGGGGC GGCGGCTGCG GTACCTGCCC ACCGGGAGCT TTCCCTTCCT 240

TCTCCTGCTG CTGCTGCTCT GCATCCAGCT CGGGGGAGGA CAGAAGAAAA AGGAGAATCT 300

TTTAGCTGAA AAAGTAGAGC AGCTGATGGA ATGGAGTTCC AGACGCTCAA TCTTCCGAAT 360

GAATGGTGAT AAATTCCGAA AATTTATAAA GGCACCACCT CGAAACTATT CCATGATTGT 420

TATGTTCACT GCTCTTCAGC CTCAGCGGCA GTGTTCTGTG TGCAGGCAAG CTAATGAAGA 480

ATATCAAATA CTGGCGAACT CCTGGCGCTA TTCATCTGCT TTTTGTAACA AGCTCTTCTT 540

CAGTATGGTG GACTATGATG AGGGGACAGA CGTTTTTCAG CAGCTCAACA TGAACTCTGC 600

TCCTACATTC ATGCATTTTC CTCCAAAAGG CAGACCTAAG AGAGCTGATA CTTTTGACCT 660

CCAAAGAATT GGATTTGCAG CTGAGCAACT AGCAAAGTGG ATTGCTGACA GAACGGATGT 720

TCATATTCGG GTTTTCAGAC CACCCAACTA CTCTGGTACC ATTGCTTTGG CCCTGTTAGT 780

GTCGCTTGTT GGAGGTTTGC TTTATTTGAG AAGGAACAAC TTGGAGTTCA TCTATAACAA 840

GACTGGTTGG GCCATGGTGT CTCTGTGTAT AGTCTTTGCT ATGACTTCTG GCCAGATGTG 900

GAACCATATC CGTGGACCTC CATATGCTCA TAAGAACCCA CACAATGGAC AAGTGAGCTA 960

CATTCATGGG AGCAGCCAGG CTCAGTTTGT GGCAGAATCA CACATTATTC TGGTACTGAA 1020

TGCCGCTATC ACCATGGGGA TGGTTCTTCT AAATGAAGCA GCAACTTCGA AAGGCGATGT 1080

TGGAAAAAGA CGGATAATTT GCCTAGTGGG ATTGGGCCTG GTGGTCTTCT TCTTCAGTTT 1140

TCTACTTTCA ATATTTCGTT CCAAGTACCA CGGCTATCCT TATAGTGATC TGGACTTTGA 1200

GTGAGAAGAT GTGATTTGGA CCATGGCACT TAAAAACTCT ATAACCTCAG CCTTTTAATT 1260

AAATGAAGCC AAGTGGGATT TGCATAAAGT GAATGTTTAC CATGAAGATA AACTGTTCCT 1320

GACTTTATAC TATTTTGAAT TC 1342

(2) INFORMATION FOR SEQ ID NO:53:

(i) SEQUENCE CHARACTERISTICS:
(A) LENGTH: 1342 base pairs
(B) TYPE: nucleic acid
(C) STRANDEDNESS: double
(D) TOPOLOGY: linear (xi) SEQUENCE DESCRIPTION: SEQ ID NO:53:

```
GAATTCGGGC GGCCGCGGCC CGGGTCCCTC GCAAAGCCGC TGCCATCCCG GAGGGCCCAG      60

CCAGCGGGCT CCCGGAGGCT GGCCGGGCAG GCGTGGTGCG CGGTAGGAGC TGGGCGCGCA     120

CGGCTACCGC GCGTGGAGGA GACACTGCCC TGCCGCGATG GGGGCCCGGG GCGCTCCTTC     180

ACGCCGTAGG CAAGCGGGGC GGCGGCTGCG GTACCTGCCC ACCGGGAGCT TTCCCTTCCT     240

TCTCCTGCTG CTGCTGCTCT GCATCCAGCT CGGGGGAGGA CAGAAGAAAA AGGAGAATCT     300

TTTAGCTGAA AAAGTAGAGC AGCTGATGGA ATGGAGTTCC AGACGCTCAA TCTTCCGAAT     360

GAATGGTGAT AAATTCCGAA AATTTATAAA GGCACCACCT CGAAACTATT CCATGATTGT     420

TATGTTCACT GCTCTTCAGC CTCAGCGGCA GTGTTCTGTG TGCAGGCAAG CTAATGAAGA     480

ATATCAAATA CTGGCGAACT CCTGGCGCTA TTCATCTGCT TTTTGTAACA AGCTCTTCTT     540

CAGTATGGTG GACTATGATG AGGGGACAGA CGTTTTTCAG CAGCTCAACA TGAACTCTGC     600

TCCTACATTC ATGCATTTTC CTCCAAAAGG CAGACCTAAG AGAGCTGATA CTTTTGACCT     660

CCAAAGAATT GGATTTGCAG CTGAGCAACT AGCAAAGTGG ATTGCTGACA GAACGGATGT     720

TCATATTCGG GTTTTCAGAC CACCCAACTA CTCTGGTACC ATTGCTTTGG CCCTGTTAGT     780

GTCGCTTGTT GGAGGTTTGC TTTATTTGAG AAGGAACAAC TTGGAGTTCA TCTATAACAA     840

GACTGGTTGG CCATGGTGT CTCTGTGTAT AGTCTTTGCT ATGACTTCTG GCCAGATGTG      900

GAACCATATC CGTGGACCTC CATATGCTCA TAAGAACCCA CACAATGGAC AAGTGAGCTA     960

CATTCATGGG AGCAGCCAGG CTCAGTTTGT GGCAGAATCA CACATTATTC TGGTACTGAA    1020

TGCCGCTATC ACCATGGGGA TGGTTCTTCT AAATGAAGCA GCAACTTCGA AAGGCGATGT    1080

TGGAAAAAGA CGGATAATTT GCCTAGTGGG ATTGGGCCTG GTGGTCTTCT TCTTCAGTTT    1140

TCTACTTTCA ATATTTCGTT CCAAGTACCA CGGCTATCCT TATAGTGATC TGGACTTTGA    1200

GTGAGAAGAT GTGATTTGGA CCATGGCACT TAAAAACTCT ATAACCTCAG CTTTTTAATT    1260

AAATGAAGCC AAGTGGGATT TGCATAAAGT GAATGTTTAC CATGAAGATA AACTGTTCCT    1320

GACTTTATAC TATTTTGAAT TC                                            1342
```

(2) INFORMATION FOR SEQ ID NO:54:

(i) SEQUENCE CHARACTERISTICS:
(A) LENGTH: 1342 base pairs
(B) TYPE: nucleic acid
(C) STRANDEDNESS: double
(D) TOPOLOGY: linear (xi) SEQUENCE DESCRIPTION: SEQ ID NO:54:

```
CTTAAGCCCG CCGGCGCCGG GCCCAGGGAG CGTTTCGGCG ACGGTAGGGC CTCCCGGGTC      60

GGTCGCCCGA GGGCCTCCGA CCGGCCCGTC CGCACCACGC GCCATCCTCG ACCCGCGCGT     120

GCCGATGGCG CGCACCTCCT CTGTGACGGG ACGGCGCTAC CCCCGGGCCC CGCGAGGAAG     180

TGCGGCATCC GTTCGCCCCG CCGCCGACGC CATGGACGGG TGGCCCTCGA AAGGGAAGGA     240

AGAGGACGAC GACGACAGAGA CGTAGGTCGA GCCCCCTCCT GTCTTCTTTT TCCTCTTAGA    300

AAATCGACTT TTTCATCTCG TCGACTACCT TACCTCAAGG TCTGCGAGTT AGAAGGCTTA     360
```

-continued

```
CTTACCACTA TTTAAGGCTT TTAAATATTT CCGTGGTGGA GCTTTGATAA GGTACTAACA      420

ATACAAGTGA CGAGAAGTCG GAGTCGCCGT CACAAGACAC ACGTCCGTTC GATTACTTCT      480

TATAGTTTAT GACCGCTTGA GGACCGCGAT AAGTAGACGA AAAACATTGT TCGAGAAGAA      540

GTCATACCAC CTGATACTAC TCCCCTGTCT GCAAAAAGTC GTCGAGTTGT ACTTGAGACG      600

AGGATGTAAG TACGTAAAAG GAGGTTTTCC GTCTGGATTC TCTCGACTAT GAAAACTGGA      660

GGTTTCTTAA CCTAAACGTC GACTCGTTGA TCGTTTCACC TAACGACTGT CTTGCCTACA      720

AGTATAAGCC CAAAAGTCTG GTGGGTTGAT GAGACCATGG TAACGAAACC GGGACAATCA      780

CAGCGAACAA CCTCCAAACG AAATAAACTC TTCCTTGTTG AACCTCAAGT AGATATTGTT      840

CTGACCAACC CGGTACCACA GAGACACATA TCAGAAACGA TACTGAAGAC CGGTCTACAC      900

CTTGGTATAG GCACCTGGAG GTATACGAGT ATTCTTGGGT GTGTTACCTG TTCACTCGAT      960

GTAAGTACCC TCGTCGGTCC GAGTCAAACA CCGTCTTAGT GTGTAATAAG ACCATGACTT     1020

ACGGCGATAG TGGTACCCCT ACCAAGAAGA TTTACTTCGT CGTTGAAGCT TTCCGCTACA     1080

ACCTTTTTCT GCCTATTAAA CGGATCACCC TAACCCGGAC CACCAGAAGA AGAAGTCAAA     1140

AGATGAAAGT TATAAAGCAA GGTTCATGGT GCCGATAGGA ATATCACTAG ACCTGAAACT     1200

CACTCTTCTA CACTAAACCT GGTACCGTGA ATTTTTGAGA TATTGGAGTC GAAAAATTAA     1260

TTTACTTCGG TTCACCCTAA ACGTATTTCA CTTACAAATG GTACTTCTAT TTGACAAGGA     1320

CTGAAATATG ATAAAACTTA AG                                             1342
```

(2) INFORMATION FOR SEQ ID NO:55:

(i) SEQUENCE CHARACTERISTICS:
        (A) LENGTH: 1047 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1045

(xi) SEQUENCE DESCRIPTION: SEQ ID NO:55:

```
ATG GGG GCC CGG GGC GCT CCT TCA CGC CGT AGG CAA GCG GGG CGG CGG        48
Met Gly Ala Arg Gly Ala Pro Ser Arg Arg Arg Gln Ala Gly Arg Arg
 1               5                  10                  15

CTG CGG TAC CTG CCC ACC GGG AGC TTT CCC TTC CTT CTC CTG CTG CTG        96
Leu Arg Tyr Leu Pro Thr Gly Ser Phe Pro Phe Leu Leu Leu Leu Leu
             20                  25                  30

CTG CTC TGC ATC CAG CTC GGG GGA GGA CAG AAG AAA AAG GAG AAT CTT       144
Leu Leu Cys Ile Gln Leu Gly Gly Gly Gln Lys Lys Lys Glu Asn Leu
         35                  40                  45

TTA GCT GAA AAA GTA GAG CAG CTG ATG GAA TGG AGT TCC AGA CGC TCA       192
Leu Ala Glu Lys Val Glu Gln Leu Met Glu Trp Ser Ser Arg Arg Ser
     50                  55                  60

ATC TTC CGA ATG AAT GGT GAT AAA TTC CGA AAA TTT ATA AAG GCA CCA       240
Ile Phe Arg Met Asn Gly Asp Lys Phe Arg Lys Phe Ile Lys Ala Pro
 65                  70                  75                  80

CCT CGA AAC TAT TCC ATG ATT GTT ATG TTC ACT GCT CTT CAG CCT CAG       288
Pro Arg Asn Tyr Ser Met Ile Val Met Phe Thr Ala Leu Gln Pro Gln
                 85                  90                  95

CGG CAG TGT TCT GTG TGC AGG CAA GCT AAT GAA GAA TAT CAA ATA CTG       336
Arg Gln Cys Ser Val Cys Arg Gln Ala Asn Glu Glu Tyr Gln Ile Leu
            100                 105                 110

GCG AAC TCC TGG CGC TAT TCA TCT GCT TTT TGT AAC AAG CTC TTC TTC       384
Ala Asn Ser Trp Arg Tyr Ser Ser Ala Phe Cys Asn Lys Leu Phe Phe
```

-continued

```
              115                 120                 125
AGT ATG GTG GAC TAT GAT GAG GGA ACA GAC GTT TTT CAG CAG CTC AAC         432
Ser Met Val Asp Tyr Asp Glu Gly Thr Asp Val Phe Gln Gln Leu Asn
    130                 135                 140

ATG AAC TCT GCT CCT ACA TTC ATG CAT TTT CCT CCA AAA GGC AGA CCT         480
Met Asn Ser Ala Pro Thr Phe Met His Phe Pro Pro Lys Gly Arg Pro
145                 150                 155                 160

AAG AGA GCT GAT ACT TTT GAC CTC CAA AGA ATT GGA TTT GCA GCT GAG         528
Lys Arg Ala Asp Thr Phe Asp Leu Gln Arg Ile Gly Phe Ala Ala Glu
                165                 170                 175

CAA CTA GCA AAG TGG ATT GCT GAC AGA ACG GAT GTT CAT ATT CGG GTT         576
Gln Leu Ala Lys Trp Ile Ala Asp Arg Thr Asp Val His Ile Arg Val
            180                 185                 190

TTC AGA CCA CCC AAC TAC TCT GGT ACC ATT GCT TTG GCC CTG TTA GTG         624
Phe Arg Pro Pro Asn Tyr Ser Gly Thr Ile Ala Leu Ala Leu Leu Val
        195                 200                 205

TCG CTT GTT GGA GGT TTG CTT TAT TTG AGA AGG AAC AAC TTG GAG TTC         672
Ser Leu Val Gly Gly Leu Leu Tyr Leu Arg Arg Asn Asn Leu Glu Phe
    210                 215                 220

ATC TAT AAC AAG ACT GGT TGG GCC ATG GTG TCT CTG TGT ATA GTC TTT         720
Ile Tyr Asn Lys Thr Gly Trp Ala Met Val Ser Leu Cys Ile Val Phe
225                 230                 235                 240

GCT ATG ACT TCT GGC CAG ATG TGG AAC CAT ATC CGT GGA CCT CCA TAT         768
Ala Met Thr Ser Gly Gln Met Trp Asn His Ile Arg Gly Pro Pro Tyr
                245                 250                 255

GCT CAT AAG AAC CCA CAC AAT GGA CAA GTG AGC TAC ATT CAT GGG AGC         816
Ala His Lys Asn Pro His Asn Gly Gln Val Ser Tyr Ile His Gly Ser
            260                 265                 270

AGC CAG GCT CAG TTT GTG GCA GAA TCA CAC ATT ATT CTG GTA CTG AAT         864
Ser Gln Ala Gln Phe Val Ala Glu Ser His Ile Ile Leu Val Leu Asn
        275                 280                 285

GCC GCT ATC ACC ATG GGG ATG GTT CTT CTA AAT GAA GCA GCA ACT TCG         912
Ala Ala Ile Thr Met Gly Met Val Leu Leu Asn Glu Ala Ala Thr Ser
    290                 295                 300

AAA GGC GAT GTT GGA AAA AGA CGG ATA ATT TGC CTA GTG GGA TTG GGC         960
Lys Gly Asp Val Gly Lys Arg Arg Ile Ile Cys Leu Val Gly Leu Gly
305                 310                 315                 320

CTG GTG GTC TTC TTC TTC AGT TTT CTA CTT TCA ATA TTT CGT TCC AAG        1008
Leu Val Val Phe Phe Phe Ser Phe Leu Leu Ser Ile Phe Arg Ser Lys
                325                 330                 335

TAC CAC GGC TAT CCT TAT AGT GAT CTG GAC TTT GAG T GA                    1047
Tyr His Gly Tyr Pro Tyr Ser Asp Leu Asp Phe Glu
            340                 345
```

(2) INFORMATION FOR SEQ ID NO:56:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:56:

```
Met Gly Ala Arg Gly Ala Pro Ser Arg Arg Gln Ala Gly Arg Arg
 1               5                  10                  15

Leu Arg Tyr Leu Pro Thr Gly Ser Phe Pro Phe Leu Leu Leu Leu
            20                  25                  30

Leu Leu Cys Ile Gln Leu Gly Gly Gly Gln Lys Lys Glu Asn Leu
        35                  40                  45
```

```
Leu Ala Glu Lys Val Glu Gln Leu Met Glu Trp Ser Ser Arg Arg Ser
 50                  55                  60

Ile Phe Arg Met Asn Gly Asp Lys Phe Arg Lys Phe Ile Lys Ala Pro
 65                      70                  75                  80

Pro Arg Asn Tyr Ser Met Ile Val Met Phe Thr Ala Leu Gln Pro Gln
                     85                  90                  95

Arg Gln Cys Ser Val Cys Arg Gln Ala Asn Glu Glu Tyr Gln Ile Leu
                100                 105                 110

Ala Asn Ser Trp Arg Tyr Ser Ser Ala Phe Cys Asn Lys Leu Phe Phe
                115                 120                 125

Ser Met Val Asp Tyr Asp Glu Gly Thr Asp Val Phe Gln Gln Leu Asn
    130                 135                 140

Met Asn Ser Ala Pro Thr Phe Met His Phe Pro Lys Gly Arg Pro
145                 150                 155                 160

Lys Arg Ala Asp Thr Phe Asp Leu Gln Arg Ile Gly Phe Ala Ala Glu
                165                 170                 175

Gln Leu Ala Lys Trp Ile Ala Asp Arg Thr Asp Val His Ile Arg Val
                180                 185                 190

Phe Arg Pro Pro Asn Tyr Ser Gly Thr Ile Ala Leu Ala Leu Leu Val
        195                 200                 205

Ser Leu Val Gly Gly Leu Leu Tyr Leu Arg Arg Asn Asn Leu Glu Phe
    210                 215                 220

Ile Tyr Asn Lys Thr Gly Trp Ala Met Val Ser Leu Cys Ile Val Phe
225                 230                 235                 240

Ala Met Thr Ser Gly Gln Met Trp Asn His Ile Arg Gly Pro Pro Tyr
                245                 250                 255

Ala His Lys Asn Pro His Asn Gly Gln Val Ser Tyr Ile His Gly Ser
                260                 265                 270

Ser Gln Ala Gln Phe Val Ala Glu Ser His Ile Ile Leu Val Leu Asn
    275                 280                 285

Ala Ala Ile Thr Met Gly Met Val Leu Leu Asn Glu Ala Ala Thr Ser
    290                 295                 300

Lys Gly Asp Val Gly Lys Arg Arg Ile Ile Cys Leu Val Gly Leu Gly
305                 310                 315                 320

Leu Val Val Phe Phe Phe Ser Phe Leu Leu Ser Ile Phe Arg Ser Lys
                325                 330                 335

Tyr His Gly Tyr Pro Tyr Ser Asp Leu Asp Phe Glu
                340                 345
```

(2) INFORMATION FOR SEQ ID NO:57:

(i) SEQUENCE CHARACTERISTICS:
        (A) LENGTH: 1044 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1042

(xi) SEQUENCE DESCRIPTION: SEQ ID NO:57:

```
ATG GGG GCC CGG GGC GCT CCT TCA CGC CGT AGG CAA GCG GGG CGG CGG       48
Met Gly Ala Arg Gly Ala Pro Ser Arg Arg Gln Ala Gly Arg Arg
 1               5                  10                  15

CTG CGG TAC CTG CCC ACC GGG AGC TTT CCC TTC CTT CTC CTG CTG CTG       96
Leu Arg Tyr Leu Pro Thr Gly Ser Phe Pro Phe Leu Leu Leu Leu Leu
            20                  25                  30
```

```
CTG CTC TGC ATC CAG CTC GGG GGA GGA CAG AAG AAA AAG GAG AAT CTT      144
Leu Leu Cys Ile Gln Leu Gly Gly Gly Gln Lys Lys Lys Glu Asn Leu
         35                  40                  45

TTA GCT GAA AAA GTA GAG CAG CTG ATG GAA TGG AGT TCC AGA CGC TCA      192
Leu Ala Glu Lys Val Glu Gln Leu Met Glu Trp Ser Ser Arg Arg Ser
 50                  55                  60

ATC TTC CGA ATG AAT GGT GAT AAA TTC CGA AAA TTT ATA AAG GCA CCA      240
Ile Phe Arg Met Asn Gly Asp Lys Phe Arg Lys Phe Ile Lys Ala Pro
 65                  70                  75                  80

CCT CGA AAC TAT TCC ATG ATT GTT ATG TTC ACT GCT CTT CAG CCT CAG      288
Pro Arg Asn Tyr Ser Met Ile Val Met Phe Thr Ala Leu Gln Pro Gln
                 85                  90                  95

CGG CAG TGT TCT GTG TGC AGG CAA GCT AAT GAA GAA TAT CAA ATA CTG      336
Arg Gln Cys Ser Val Cys Arg Gln Ala Asn Glu Glu Tyr Gln Ile Leu
             100                 105                 110

GCG AAC TCC TGG CGC TAT TCA TCT GCT TTT TGT AAC AAG CTC TTC TTC      384
Ala Asn Ser Trp Arg Tyr Ser Ser Ala Phe Cys Asn Lys Leu Phe Phe
         115                 120                 125

AGT ATG GTG GAC TAT GAT GAG GGG ACA GAC GTT TTT CAG CAG CTC AAC      432
Ser Met Val Asp Tyr Asp Glu Gly Thr Asp Val Phe Gln Gln Leu Asn
     130                 135                 140

ATG AAC TCT GCT CCT ACA TTC ATG CAT TTT CCT CCA AAA GGC AGA CCT      480
Met Asn Ser Ala Pro Thr Phe Met His Phe Pro Pro Lys Gly Arg Pro
145                 150                 155                 160

AAG AGA GCT GAT ACT TTT GAC CTC CAA AGA ATT GGA TTT GCA GCT GAG      528
Lys Arg Ala Asp Thr Phe Asp Leu Gln Arg Ile Gly Phe Ala Ala Glu
                 165                 170                 175

CAA CTA GCA AAG TGG ATT GCT GAC AGA ACG GAT GTT CAT ATT CGG GTT      576
Gln Leu Ala Lys Trp Ile Ala Asp Arg Thr Asp Val His Ile Arg Val
             180                 185                 190

TTC AGA CCA CCC AAC TAC TCT GGT ACC ATT GCT TTG GCC CTG TTA GTG      624
Phe Arg Pro Pro Asn Tyr Ser Gly Thr Ile Ala Leu Ala Leu Leu Val
         195                 200                 205

TCG CTT GTT GGA GGT TTG CTT TAT TTG AGA AGG AAC AAC TTG GAG TTC      672
Ser Leu Val Gly Gly Leu Leu Tyr Leu Arg Arg Asn Asn Leu Glu Phe
     210                 215                 220

ATC TAT AAC AAG ACT GGT TGG GCC ATG GTG TCT CTG TGT ATA GTC TTT      720
Ile Tyr Asn Lys Thr Gly Trp Ala Met Val Ser Leu Cys Ile Val Phe
225                 230                 235                 240

GCT ATG ACT TCT GGC CAG ATG TGG AAC CAT ATC CGT GGA CCT CCA TAT      768
Ala Met Thr Ser Gly Gln Met Trp Asn His Ile Arg Gly Pro Pro Tyr
                 245                 250                 255

GCT CAT AAG AAC CCA CAC AAT GGA CAA GTG AGC TAC ATT CAT GGG AGC      816
Ala His Lys Asn Pro His Asn Gly Gln Val Ser Tyr Ile His Gly Ser
             260                 265                 270

AGC CAG GCT CAG TTT GTG GCA GAA TCA CAC ATT ATT CTG GTA CTG AAT      864
Ser Gln Ala Gln Phe Val Ala Glu Ser His Ile Ile Leu Val Leu Asn
         275                 280                 285

GCC GCT ATC ACC ATG GGG ATG GTT CTT CTA AAT GAA GCA GCA ACT TCG      912
Ala Ala Ile Thr Met Gly Met Val Leu Leu Asn Glu Ala Ala Thr Ser
     290                 295                 300

AAA GGC GAT GTT GGA AAA AGA CGG ATA ATT TGC CTA GTG GGA TTG GGC      960
Lys Gly Asp Val Gly Lys Arg Arg Ile Ile Cys Leu Val Gly Leu Gly
305                 310                 315                 320

CTG GTG GTC TTC TTC TTC AGT TTT CTA CTT TCA ATA TTT CGT TCC AAG     1008
Leu Val Val Phe Phe Phe Ser Phe Leu Leu Ser Ile Phe Arg Ser Lys
                 325                 330                 335

TAC CAC GGC TAT CCT TAT AGC TTT TTA ATT AAA T GA                    1044
Tyr His Gly Tyr Pro Tyr Ser Phe Leu Ile Lys
```

(2) INFORMATION FOR SEQ ID NO:58:

(i) SEQUENCE CHARACTERISTICS:
        (A) LENGTH: 347 amino acids
        (B) TYPE: amino acid
        (D) TOPOLOGY: linear (ii) MOLECULE TYPE: protein (xi) SEQUENCE DESCRIPTION: SEQ ID NO:58:

```
Met Gly Ala Arg Gly Ala Pro Ser Arg Arg Gln Ala Gly Arg Arg
 1               5                  10                  15

Leu Arg Tyr Leu Pro Thr Gly Ser Phe Pro Phe Leu Leu Leu Leu
                20                  25                  30

Leu Leu Cys Ile Gln Leu Gly Gly Gln Lys Lys Lys Glu Asn Leu
            35                  40                  45

Leu Ala Glu Lys Val Glu Gln Leu Met Glu Trp Ser Ser Arg Arg Ser
        50                  55                  60

Ile Phe Arg Met Asn Gly Asp Lys Phe Arg Lys Phe Ile Lys Ala Pro
 65                  70                  75                  80

Pro Arg Asn Tyr Ser Met Ile Val Met Phe Thr Ala Leu Gln Pro Gln
                85                  90                  95

Arg Gln Cys Ser Val Cys Arg Gln Ala Asn Glu Glu Tyr Gln Ile Leu
                100                 105                 110

Ala Asn Ser Trp Arg Tyr Ser Ser Ala Phe Cys Asn Lys Leu Phe Phe
                115                 120                 125

Ser Met Val Asp Tyr Asp Glu Gly Thr Asp Val Phe Gln Gln Leu Asn
130                 135                 140

Met Asn Ser Ala Pro Thr Phe Met His Phe Pro Pro Lys Gly Arg Pro
145                 150                 155                 160

Lys Arg Ala Asp Thr Phe Asp Leu Gln Arg Ile Gly Phe Ala Ala Glu
                165                 170                 175

Gln Leu Ala Lys Trp Ile Ala Asp Arg Thr Asp Val His Ile Arg Val
                180                 185                 190

Phe Arg Pro Pro Asn Tyr Ser Gly Thr Ile Ala Leu Ala Leu Leu Val
                195                 200                 205

Ser Leu Val Gly Gly Leu Leu Tyr Leu Arg Arg Asn Asn Leu Glu Phe
210                 215                 220

Ile Tyr Asn Lys Thr Gly Trp Ala Met Val Ser Leu Cys Ile Val Phe
225                 230                 235                 240

Ala Met Thr Ser Gly Gln Met Trp Asn His Ile Arg Gly Pro Pro Tyr
                245                 250                 255

Ala His Lys Asn Pro His Asn Gly Gln Val Ser Tyr Ile His Gly Ser
                260                 265                 270

Ser Gln Ala Gln Phe Val Ala Glu Ser His Ile Ile Leu Val Leu Asn
                275                 280                 285

Ala Ala Ile Thr Met Gly Met Val Leu Leu Asn Glu Ala Ala Thr Ser
                290                 295                 300

Lys Gly Asp Val Gly Lys Arg Arg Ile Ile Cys Leu Val Gly Leu Gly
305                 310                 315                 320

Leu Val Val Phe Phe Phe Ser Phe Leu Leu Ser Ile Phe Arg Ser Lys
                325                 330                 335

Tyr His Gly Tyr Pro Tyr Ser Phe Leu Ile Lys
                340                 345
```

(2) INFORMATION FOR SEQ ID NO:59:

(i) SEQUENCE CHARACTERISTICS:
        (A) LENGTH: 331 amino acids
        (B) TYPE: amino acid
        (D) TOPOLOGY: linear (xi) SEQUENCE DESCRIPTION: SEQ ID NO:59:

```
Met Leu Leu Ala Val Tyr Glu Ser Ala Gln Gln Gln Thr Leu Glu Asp
1               5                   10                  15

Lys Val Gln Asn Leu Val Asp Leu Thr Ser Arg Gln Ser Ile Val Lys
                20                  25                  30

Phe Asn Met Asp Lys Trp Lys Thr Leu Val Arg Met Gln Pro Arg Asn
            35                  40                  45

Tyr Ser Met Ile Val Met Phe Thr Ala Leu Ser Pro Gly Val Gln Cys
        50                  55                  60

Pro Ile Cys Lys Pro Ala Tyr Asp Glu Phe Met Ile Val Ala Asn Ser
65                  70                  75                  80

His Arg Tyr Thr Ser Ser Glu Gly Asp Arg Arg Lys Val Phe Phe Gly
                85                  90                  95

Ile Val Asp Tyr Glu Asp Ala Pro Gln Ile Phe Gln Gln Met Asn Leu
                100                 105                 110

Asn Thr Ala Pro Ile Leu Tyr His Phe Gly Pro Lys Leu Gly Ala Lys
            115                 120                 125

Lys Arg Pro Glu Gln Met Asp Phe Gln Arg Gln Gly Phe Asp Ala Asp
            130                 135                 140

Ala Ile Gly Arg Phe Val Ala Asp Gln Thr Glu Val His Val Arg Val
145                 150                 155                 160

Ile Arg Pro Pro Asn Tyr Thr Ala Pro Val Val Ile Ala Leu Phe Val
                165                 170                 175

Ala Leu Leu Leu Gly Met Leu Tyr Met Lys Arg Asn Ser Leu Asp Phe
                180                 185                 190

Leu Phe Asn Arg Thr Val Trp Gly Phe Val Cys Leu Ala Ile Thr Phe
            195                 200                 205

Ile Phe Met Ser Gly Gln Met Trp Asn His Ile Arg Gly Pro Pro Phe
            210                 215                 220

Met Ile Thr Asn Pro Asn Thr Lys Glu Pro Ser Phe Ile His Gly Ser
225                 230                 235                 240

Thr Gln Phe Gln Leu Ile Ala Glu Thr Tyr Ile Val Gly Leu Leu Tyr
                245                 250                 255

Ala Leu Ile Ala Ile Gly Phe Ile Cys Val Asn Glu Ala Ala Asp Gln
            260                 265                 270

Ser Asn Ser Lys Asp Arg Lys Asn Ala Gly Lys Lys Leu Asn Pro Leu
            275                 280                 285

Ser Leu Leu Asn Ile Pro Thr Asn Thr Leu Ala Ile Ala Gly Leu Val
            290                 295                 300

Cys Ile Cys Val Phe Phe Ser Phe Leu Leu Ser Val Phe Arg Ser Lys
305                 310                 315                 320

Tyr Arg Gly Tyr Pro Tyr Ser Phe Leu Phe Ala
                325                 330
```